United States Patent
Reddy et al.

(10) Patent No.: US 7,932,242 B2
(45) Date of Patent: *Apr. 26, 2011

(54) SUBSTITUTED PHENOXY- AND PHENYLTHIO-DERIVATIVES FOR TREATING PROLIFERATIVE DISORDERS

(75) Inventors: E. Premkumar Reddy, Villanova, PA (US); M. V. Ramana Reddy, Upper Darby, PA (US); Stanley C. Bell, Narberth, PA (US)

(73) Assignees: Temple University - Of The Commonwealth System of Higher Education, Philadelphia, PA (US); Onconova Therapeutics Inc., Newton, PA (US)

(*) Notice: Subject to any disclaimer, the term of this patent is extended or adjusted under 35 U.S.C. 154(b) by 0 days.

This patent is subject to a terminal disclaimer.

(21) Appl. No.: 10/592,604

(22) PCT Filed: Mar. 15, 2005

(86) PCT No.: PCT/US2005/008429
§ 371 (c)(1), (2), (4) Date: Sep. 12, 2006

(87) PCT Pub. No.: WO2005/089269
PCT Pub. Date: Sep. 29, 2005

(65) Prior Publication Data
US 2008/0058290 A1    Mar. 6, 2008

Related U.S. Application Data

(60) Provisional application No. 60/554,008, filed on Mar. 16, 2004.

(51) Int. Cl.
*A01N 57/00* (2006.01)
*A61K 31/66* (2006.01)

(52) U.S. Cl. ............ 514/127; 514/239.3; 514/506; 514/532; 514/601; 514/613; 514/708; 514/709; 530/402; 544/158; 558/177; 558/51; 560/11; 564/123; 564/80; 568/32; 568/37

(58) Field of Classification Search .......... 514/708, 514/710, 709; 568/28
See application file for complete search history.

(56) References Cited

U.S. PATENT DOCUMENTS

| | | | |
|---|---|---|---|
| 3,865,867 A | 2/1975 | Olin et al. | 260/472 |
| 3,975,435 A | 8/1976 | Nikawitz | 260/558 |
| 6,117,364 A | 9/2000 | Vorderbruggen et al. | 252/395 |
| 6,201,154 B1 | 3/2001 | Reddy et al. | 568/28 |
| 6,359,013 B1 | 3/2002 | Reddy et al. | 514/710 |
| 6,376,519 B1 | 4/2002 | Reddy et al. | 514/341 |
| 6,414,034 B1 | 7/2002 | Reddy et al. | 514/710 |
| 6,486,210 B2 * | 11/2002 | Reddy et al. | 514/708 |
| 6,541,475 B2 | 4/2003 | Reddy et al. | 514/252.12 |
| 6,548,553 B2 | 4/2003 | Reddy et al. | 514/710 |
| 6,576,675 B1 | 6/2003 | Reddy et al. | 514/710 |
| 6,599,932 B1 | 7/2003 | Reddy et al. | 514/438 |
| 6,646,009 B2 | 11/2003 | Reddy et al. | 514/604 |
| 6,656,968 B1 | 12/2003 | Reddy et al. | 514/508 |
| 6,656,973 B2 | 12/2003 | Cosenza et al. | 514/710 |
| 6,667,346 B2 * | 12/2003 | Reddy et al. | 514/710 |
| 6,762,207 B1 | 7/2004 | Reddy et al. | 514/709 |
| 6,767,926 B1 * | 7/2004 | Cosenza et al. | 514/710 |
| 6,787,667 B2 | 9/2004 | Reddy et al. | 562/429 |
| 6,833,480 B2 | 12/2004 | Reddy et al. | 568/28 |
| 7,053,123 B2 | 5/2006 | Reddy et al. | 514/710 |
| 7,056,953 B2 | 6/2006 | Reddy et al. | 514/710 |
| 2003/0114538 A1 | 6/2003 | Reddy et al. | 514/709 |
| 2005/0130942 A1 | 6/2005 | Reddy et al. | 514/114 |
| 2006/0167317 A1 | 7/2006 | Reddy et al. | 564/211 |
| 2006/0280746 A1 | 12/2006 | Reddy et al. | 424/155.1 |

FOREIGN PATENT DOCUMENTS
FR    2 559 646    2/1984
* cited by examiner

*Primary Examiner* — Daniel M Sullivan
*Assistant Examiner* — Chukwuma O Nwaonicha
(74) *Attorney, Agent, or Firm* — Drinker Biddle & Reath LLP

(57) ABSTRACT

Substituted phenol derivatives of Formula (I) are useful as antiproliferative agents including, for example, anticancer agents, and as radioprotective and chemoprotective agents.

26 Claims, 1 Drawing Sheet

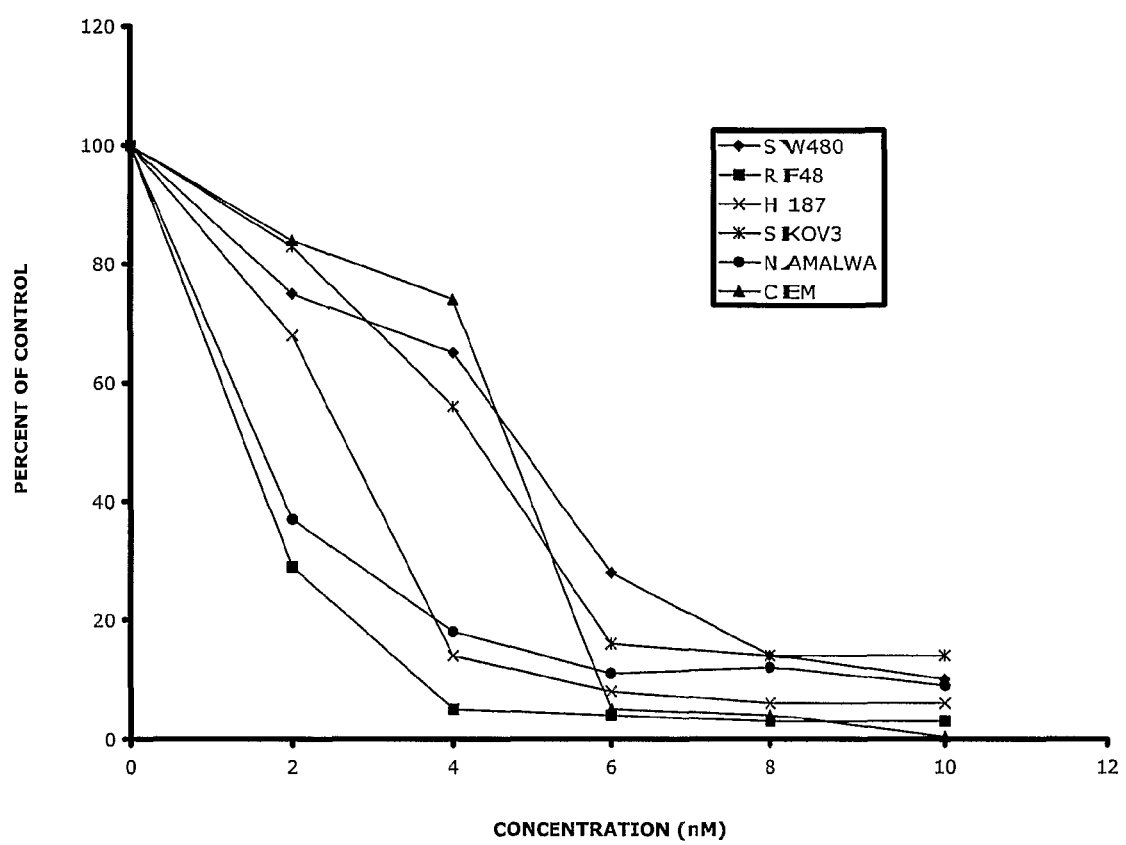

SUBSTITUTED PHENOXY- AND PHENYLTHIO-DERIVATIVES FOR TREATING PROLIFERATIVE DISORDERS

CROSS-REFERENCE TO RELATED APPLICATION

This application claims the benefit of U.S. Provisional Application Ser. No. 60/554,008, filed Mar. 16, 2004, the entire disclosure of which is incorporated herein by reference.

FIELD OF THE INVENTION

The invention relates to compositions and methods for the treatment of proliferative disorders, including but not limited to cancer. The invention further relates to compositions that afford protection from the cytotoxic effects of ionizing radiation and of cytotoxic chemotherapeutic agents.

BACKGROUND OF THE INVENTION

α,β-Unsaturated Sulfone Compounds

Certain α,β-unsaturated sulfones, particularly certain styrylbenzyl sulfones have been shown to posses antiproliferative, radioprotective and chemoprotective activity. The chemoprotective effect was shown to protect normal cells from the cytotoxic side effects of mitotic phase cell cycle inhibitors and topoisomerase inhibitors, used in the treatment of cancer and other proliferative disorders. See, U.S. Pat. Nos. 6,599,932, 6,576,675, 6,548,553, 6,541,475, 6,486,210, 6,414,034, 6,359,013, 6,201,154, 6,665,973, and 6,667,346 the entire disclosures of which are incorporated herein.

α,β-Unsaturated Sulfonamide Compounds

Certain α,β-unsaturated sulfonamides, particularly styrylbenzyl sulfonamides have been shown to posses antiproliferative, radioprotective and chemoprotective (protecting normal cells from the cytotoxic side effects of mitotic phase cell cycle inhibitors and topoisomerase inhibitors) activity. See, U.S. Pat. No. 6,646,009 and PCT publication WO 03072063, the entire disclosures of which are incorporated herein.

Aromatic Propenamide Compounds

Certain aromatic propenamide, particularly N-aromatic cinnamides have been shown to possess antiproliferative, radioprotective and chemoprotective (protecting normal cells from the cytotoxic side effects of mitotic phase cell cycle inhibitors and topoisomerase inhibitors) activity. See PCT publication WO 04037751, the entire disclosure of which is incorporated herein by reference.

Treatment of Proliferative Disorders

Several growth factors have been demonstrated to play a significant role in cell proliferation and differentiation. Proliferative disorders, particularly cancers arise as a result of a progression of events. Such events may include disruption of regulated expression of growth factors or components of their signaling pathways. Tyrosine phosphorylation events initiated by receptor, cytoplasmic and nuclear kinases and regulated by phosphatases are central to these processes. Mutation, hyper-activation, translocation and overexpression of protein tyrosine kinases are all associated with tumorigenesis.

Certain compounds have been shown to be tyrosine kinase inhibitors. Because of their ability to inhibit tyrosine phosphorylation, these compounds may alter cell responses, including unregulated proliferation, to growth factors or other processes associated with tyrosine kinase activity. Inhibition of tyrosine kinases associated with signaling pathways associated with proliferative disorders may be sufficient to switch a cancerous cell from a proliferative cell cycle into programmed cell death, or apoptosis.

Selective inhibition of specific tyrosine kinases offers a method of targeting cancerous cell growth with a high degree of specificity and minimal toxicity to normal cells. Thus, specific inhibitors of tyrosine kinases have great potential as clinical anti-cancer treatments.

Inhibition of tyrosine kinases offers one mechanism by which cell proliferation can be inhibited. One of skill in the art will appreciate that other mechanisms of inhibition may also be involved.

There is a need in the art to identify compounds that inhibit cell proliferation.

Ionizing Radiation Health Risks

Ionizing radiation has an adverse effect on cells and tissues, primarily through cytotoxic effects. In humans, exposure to ionizing radiation occurs primarily through therapeutic techniques (such as anticancer radiotherapy) or through occupational and environmental exposure.

Therapeutic Administration of Radiation

A major source of exposure to ionizing radiation is the administration of therapeutic radiation in the treatment of cancer or other proliferative disorders. Depending on the course of treatment prescribed by the treating physician, multiple doses may be received by an individual over the course of several weeks to several months.

Therapeutic radiation is generally applied to a defined area of the individual's body which contains abnormal proliferative tissue, in order to maximize the dose absorbed by the abnormal tissue and minimize the dose absorbed by the nearby normal tissue. However, it is difficult (if not impossible) to selectively administer therapeutic ionizing radiation to the abnormal tissue. Thus, normal tissue proximate to the abnormal tissue is also exposed to potentially damaging doses of ionizing radiation throughout the course of treatment.

There are also some treatments that require exposure of the individual's entire body to the radiation, in a procedure called "total body irradiation", or "TBI." The efficacy of radiotherapeutic techniques in destroying abnormal proliferative cells is therefore balanced by associated cytotoxic effects on nearby normal cells. Because of this, radiotherapy techniques have an inherently narrow therapeutic index which results in the inadequate treatment of most tumors. Even the best radiotherapeutic techniques may result in incomplete tumor reduction, tumor recurrence, increasing tumor burden, and induction of radiation resistant tumors.

Numerous methods have been designed to reduce normal tissue damage while still delivering effective therapeutic doses of ionizing radiation. These techniques include brachytherapy, fractionated and hyperfractionated dosing, complicated dose scheduling and delivery systems, and high voltage therapy with a linear accelerator. However, such techniques only attempt to strike a balance between the therapeutic and undesirable effects of the radiation, and full efficacy has not been achieved.

For example, one treatment for individuals with metastatic tumors involves harvesting their hematopoietic stem cells and then treating the individual with high doses of ionizing radiation. This treatment is designed to destroy the individual's tumor cells, but has the side effect of also destroying their normal hematopoietic cells. Thus, a portion of the individual's bone marrow (containing the hematopoietic stem cells), is removed prior to radiation therapy. Once the individual has been treated, the autologous hematopoietic stem cells are returned to their body.

However, if tumor cells have metastasized away from the tumor's primary site, there is a high probability that some tumor cells will contaminate the harvested hematopoietic cell population. The harvested hematopoietic cell population may also contain neoplastic cells if the individual suffers from cancers of the bone marrow such as the various French-American-British (FAB) subtypes of acute myelogenous leukemias (AML), chronic myeloid leukemia (CML), or acute lymphocytic leukemia (ALL). Thus, the metastasized tumor cells or resident neoplastic cells must be removed or killed prior to reintroducing the stem cells to the individual. If any living tumorigenic or neoplastic cells are re-introduced into the individual, they can lead to a relapse.

Prior art methods of removing tumorigenic or neoplastic cells from harvested bone marrow are based on a whole-population tumor cell separation or killing strategy, which typically does not kill or remove all of the contaminating malignant cells. Such methods include leukopheresis of mobilized peripheral blood cells, immunoaffinity-based selection or killing of tumor cells, or the use of cytotoxic or photosensitizing agents to selectively kill tumor cells. In the best case, the malignant cell burden may still be at 1 to 10 tumor cells for every 100,000 cells present in the initial harvest (Lazarus et al. *J. of Hematotherapy*, 2(4):457-66, 1993).

Thus, there is needed a purging method designed to selectively destroy the malignant cells present in the bone marrow, while preserving the normal hematopoietic stem cells needed for hematopoietic reconstitution in the transplantation subject.

Occupational/Environmental Radiation Exposure

Exposure to ionizing radiation can also occur in the occupational setting. Occupational doses of ionizing radiation may be received by persons whose job involves exposure (or potential exposure) to radiation, for example in the nuclear power and nuclear weapons industries. Military personnel stationed on vessels powered by nuclear reactors, or soldiers required to operate in areas contaminated by radioactive fallout, risk similar exposure to ionizing radiation. Occupational exposure may also occur in rescue and emergency personnel called in to deal with catastrophic events involving a nuclear reactor or radioactive material. Other sources of occupational exposure may be from machine parts, plastics, and solvents left over from the manufacture of radioactive medical products, smoke alarms, emergency signs, and other consumer goods. Occupational exposure may also occur in persons who serve on nuclear powered vessels, particularly those who tend the nuclear reactors, in military personnel operating in areas contaminated by nuclear weapons fallout, and in emergency personnel who deal with nuclear accidents. Environmental exposure to ionizing radiation may also result from nuclear weapons detonations (either experimental or during wartime), discharges of actinides from nuclear waste storage and processing and reprocessing of nuclear fuel, and from naturally occurring radioactive materials such as radon gas or uranium. There is also increasing concern that the use of ordnance containing depleted uranium results in low-level radioactive contamination of combat areas.

Radiation exposure from any source can be classified as acute (a single large exposure) or chronic (a series of small low-level, or continuous low-level exposures spread over time). Radiation sickness generally results from an acute exposure of a sufficient dose, and presents with a characteristic set of symptoms that appear in an orderly fashion, including hair loss, weakness, vomiting, diarrhea, skin burns and bleeding from the gastrointestinal tract and mucous membranes. Genetic defects, sterility and cancers (particularly bone marrow cancer) often develop over time. Chronic exposure is usually associated with delayed medical problems such as cancer and premature aging. An acute a total body exposure of 125,000 millirem may cause radiation sickness. Localized doses such as are used in radiotherapy may not cause radiation sickness, but may result in the damage or death of exposed normal cells.

For example, an acute total body radiation dose of 100,000-125,000 millirem (equivalent to 1 Gy) received in less than one week would result in observable physiologic effects such as skin burns or rashes, mucosal and GI bleeding, nausea, diarrhea and/or excessive fatigue. Longer term cytotoxic and genetic effects such as hematopoietic and immunocompetent cell destruction, hair loss (alopecia), gastrointestinal, and oral mucosal sloughing, venoocclusive disease of the liver and chronic vascular hyperplasia of cerebral vessels, cataracts, pneumonites, skin changes, and an increased incidence of cancer may also manifest over time. Acute doses of less than 10,000 millirem (equivalent to 0.1 Gy) typically will not result in immediately observable biologic or physiologic effects, although long term cytotoxic or genetic effects may occur.

A sufficiently large acute dose of ionizing radiation, for example 500,000 to over 1 million millirem (equivalent to 5-10 Gy), may kill an individual immediately. Doses in the hundreds of thousands of millirems may kill within 7 to 21 days from a condition called "acute radiation poisoning." Reportedly, some of the Chernobyl firefighters died of acute radiation poisoning, having received acute doses in the range of 200,000-600,000 millirem (equivalent to 2-6 Gy). Acute doses below approximately 200,000 millirem do not result in death, but the exposed individual will likely suffer long-term cytotoxic or genetic effects as discussed above.

Acute occupational exposures usually occur in nuclear power plant workers exposed to accidental releases of radiation, or in fire and rescue personnel who respond to catastrophic events involving nuclear reactors or other sources of radioactive material. Suggested limits for acute occupational exposures in emergency situations were developed by the Brookhaven National Laboratories, and are given in Table 1.

TABLE 1

| Whole Body Conditions for Dose Limit | Activity Required | Conditions for Exposure |
|---|---|---|
| 10,000 millirem* | Protect property | Voluntary, when lower dose not practical |
| 25,000 millirem | Lifesaving Operation; Protect General Public | Voluntary, when lower dose not practical |
| >25,000 millirem | Lifesaving operation; Protect large population | Voluntary, when lower dose not practical, and the risk has been clearly explained |

*100,000 millirem equals one sievert (Sv). For penetrating radiation such as gamma radiation, one Sv equals approximately one Gray (Gy). Thus, the dosage in Gy can be estimated as 1 Gy for every 100,000 millirem.

A chronic dose is a low level (i.e., 100-5000 millirem) incremental or continuous radiation dose received over time. Examples of chronic doses include a whole body dose of ~5000 millirem per year, which is the dose typically received by an adult working at a nuclear power plant. By contrast, the Atomic Energy Commission recommends that members of the general public should not receive more than 100 millirem per year. Chronic doses may cause long-term cytotoxic and genetic effects, for example manifesting as an increased risk of a radiation-induced cancer developing later in life. Recommended limits for chronic exposure to ionizing radiation are given in Table 2.

TABLE 2

| Organ or Subject | Annual Occupational Dose in millirem |
|---|---|
| Whole Body | 5000 |
| Lens of the Eye | 15,000 |
| Hands and wrists | 50,000 |
| Any individual organ | 50,000 |
| Pregnant worker | 500/9 months |
| Minor (16-18) receiving training | 100 |

By way of comparison, Table 3 sets forth the radiation doses from common sources.

TABLE 3

| Sources | Dose In Millirem |
|---|---|
| Television | <1/yr |
| Gamma Rays, Jet Cross Country | 1 |
| Mountain Vacation - 2 week | 3 |
| Atomic Test Fallout | 5 |
| U.S. Water, Food & Air (Average) | 30/yr |
| Wood | 50/yr |
| Concrete | 50/yr |
| Brick | 75/yr |
| Chest X-Ray | 100 |
| Cosmic Radiation (Sea Level) | 40/yr (add 1 millirem/100 ft elev.) |
| Natural Background San Francisco | 120/yr |
| Natural Background Denver | 50/yr |
| Atomic Energy Commission Limit For Workers | 5000/yr |
| Complete Dental X-Ray | 5000 |
| Natural Background at Pocos de Caldras, Brazil | 7000/yr |
| Whole Body Diagnostic X-Ray | 100,000 |
| Cancer Therapy | 500,000 (localized) |
| Radiation Sickness-Nagasaki | 125,000 (single doses) |
| $LD_{50}$ Nagasaki & Hiroshima | 400,000-500,000 (single dose) |

Chronic doses of greater than 5000 millirem per year (0.05 Gy per year) may result in long-term cytotoxic or genetic effects similar to those described for persons receiving acute doses. Some adverse cytotoxic or genetic effects may also occur at chronic doses of significantly less than 5000 millirem per year. For radiation protection purposes, it is assumed that any dose above zero can increase the risk of radiation-induced cancer (i.e., that there is no threshold). Epidemiologic studies have found that the estimated lifetime risk of dying from cancer is greater by about 0.04% per rem of radiation dose to the whole body.

While anti-radiation suits or other protective gear may be effective at reducing radiation exposure, such gear is expensive, unwieldy, and generally not available to public. Moreover, radioprotective gear will not protect normal tissue adjacent a tumor from stray radiation exposure during radiotherapy. What is needed, therefore, is a practical way to protect individuals who are scheduled to incur, or are at risk for incurring, exposure to ionizing radiation. In the context of therapeutic irradiation, it is desirable to enhance protection of normal cells while causing tumor cells to remain vulnerable to the detrimental effects of the radiation. Furthermore, it is desirable to provide systemic protection from anticipated or inadvertent total body irradiation, such as may occur with occupational or environmental exposures, or with certain therapeutic techniques.

Pharmaceutical radioprotectants offer a cost-efficient, effective and easily available alternative to radioprotective gear. However, previous attempts at radioprotection of normal cells with pharmaceutical compositions have not been entirely successful. For example, cytokines directed at mobilizing the peripheral blood progenitor cells confer a myeloprotective effect when given prior to radiation (Neta et al., Semin. Radiat. Oncol. 6:306-320, 1996), but do not confer systemic protection. Other chemical radioprotectors administered alone or in combination with biologic response modifiers have shown minor protective effects in mice, but application of these compounds to large mammals was less successful, and it was questioned whether chemical radioprotection was of any value (Maisin, J. R., Bacq and Alexander Award Lecture. "Chemical radioprotection: past, present, and future prospects", Int J. Radiat Biol. 73:443-50, 1998). Pharmaceutical radiation sensitizers, which are known to preferentially enhance the effects of radiation in cancerous tissues, are clearly unsuited for the general systemic protection of normal tissues from exposure to ionizing radiation.

What are needed are therapeutic agents to protect individuals who have incurred, or are at risk for incurring exposure to ionizing radiation. In the context of therapeutic irradiation, it is desirable to enhance protection of normal cells while causing tumor cells to remain vulnerable to the detrimental effects of the radiation. Furthermore, it is desirable to provide systemic protection from anticipated or inadvertent total body irradiation, such as may occur with occupational or environmental exposures, or with certain therapeutic techniques.

Protection from Toxic Side Effects of Experimental Chemotherapy

Experimental chemotherapy has been the mainstay of treatment offered to patients diagnosed with surgically unresectable advanced cancers, or cancers refractory to standard chemotherapy and radiation therapy. Of the more effective classes of drugs, curative properties are still limited. This is because of their relatively narrow therapeutic index, restricted dosage, delayed treatments and a relatively large proportion of only partial tumor reductions. This state is usually followed by recurrence, increased tumor burden, and drug resistant tumors.

A. Mitotic Cell Phase Inhibitors

Mitotic cell phase inhibitors constitute one class of chemotherapeutic compounds employed in cancer therapy. The usual description of the cell cycle describes the cycle in terms of a series of phases—interphase and M (mitotic) phase—and the subdivision of interphase into the times when DNA synthesis is proceeding, known as the S-phase (for synthesis phase), and the gaps that separate the S-phase from mitosis. G1 is the gap after mitosis but before DNA synthesis starts, and G2 is the gap after DNA synthesis is complete before mitosis and cell division. Interphase is thus composed of successive G1, S and G2 phases, and normally comprises 90% or more of the total cell cycle time. The M phase consists of nuclear division (mitosis) and cytoplasmic division (cytokinesis). During the early part of the M phase, the replicated chromosomes condense from their extended interphase condition. The nuclear envelope breaks down, and each chromosome undergoes movements that result in the separation of pairs of sister chromatids as the nuclear contents are divided. Two new nuclear envelopes then form, and the cytoplasm divides to generate two daughter cells, each with a single nucleus. This process of cytokinesis terminates the M phase and marks the beginning of the interphase of the next cell cycle. The daughter cells resulting from completion of the M phase begin the interphase of a new cycle.

A mitotic phase cell cycle inhibitor is a chemical agent whose mechanism of action includes inhibition of a cell's passage through any portion of the M phase of the cell cycle.

B. Topoisomerase Inhibitors

A topoisomerase inhibitor is a chemical agent whose mechanism of action includes interfering with the function of a topoisomerase.

The topoisomerases constitute a group of enzymes that catalyze the conversion of DNA from one topological form to another by introducing transient breaks in one or both strands of a DNA duplex. Topological isomers are molecules that differ only in their state of supercoiling. Topoisomerases serve to relieve torsional stress during replication and transcription. They alter the DNA structure, but not the sequence.

Three different types of topoisomerases have been reported in human. They are topoisomerase I (91 kDa monomer), and topoisomerase II, which is further subclassified as IIα (170 kDa dimer), and IIβ (180 kDa diner). The three different types are encoded by genes on three separate chromosomes. Simpler organisms possess only topoisomerase I; however, higher organisms have all three types of topoisomerases. While topoisomerase IIα is present in all eukaryotes, IIβ is present only in vertebrates and appears to be more closely associated cell differentiation than proliferation. Topoisomerase IIβ appears to be highly homologous to the type IIα.

Topoisomerases act by catalyzing the breakdown and rejoining reactions in the phosphodiester backbone of the DNA molecules. Topoisomerase I reversibly cleaves a single strand in duplex DNA molecule, whereas topoisomerase II breaks and rejoins both DNA strands. These reactions are believed to proceed via transient reaction intermediates, known as "cleavable complexes," where the enzymes (or enzyme subunits) form covalent bonds involving a tyrosine and the cleaved phosphodiester bond of the DNA substrate backbone.

In recent years, topoisomerases have become important chemotherapeutic targets for cancer treatment. Camptothecin and its derivatives are reported to act specifically at the level of the topoisomerase I-DNA complex and stimulate DNA cleavage. Agents, such as β-lapachone, act by blocking the formation of the topoisomerase I-DNA complex. Several novel compounds have been developed that can target either topoisomerase I or topoisomerase IIα-/IIβ-isoforms, or all three types of topoisomerases. Inhibition of topoisomerase II is considered to be more challenging due to the complexity of interactions. Most inhibitors of topoisomerase II block the ligation step, leading to stabilized "cleavable complexes" between DNA and the enzyme. Most enzyme inhibitors function by docking into the enzyme active site or nearby allosteric site to block the reaction of the normal substrate. Inhibition of the topoisomerase II involves two parts: the aromatic part of the inhibitor molecule intercalates between DNA base pairs and another more polar portion interacts with topoisomerase. Because topoisomerase II inhibitors (e.g., doxorubicin, and etoposide) act as poisons rather than as classical competitive inhibitors, their action is dependent upon the level of the enzyme in cells. Rapidly proliferating cells, which contain relatively higher levels of topoisomerase II, appear to be more sensitive to these agents. On the other hand, differentiated cells have relatively low topoisomerase II levels and are much more resistant to the action of these inhibitors.

C. Cytoprotective Agents

Several cytoprotective agents have been proposed to enhance the therapeutic index of anticancer drugs. For methotrexate toxicity, such agents include asparaginase, leucovorum factor, thymidine, and carbipeptidase. Because of the extensive use of anthracyclines, specific and non-specific cytoprotective agents have been proposed which have varying degrees of efficacy; included are corticosteroids, desrazoxane and staurosporin. The latter is of interest in that it includes a G1/S restriction blockade in normal cells. (Chen et al., *Proc AACR* 39:4436A, 1998).

Cisplatin is widely used and has a small therapeutic index which has spurred investigation and search of cytoprotectants. Among the cytoprotectants for cisplatin with clinical potential are mesna, glutathione, sodium thiosulfate, and amifostine (Griggs, *Leuk. Res.* 22 Suppl 1:S27-33, 1998; List et al., *Semin. Oncol.* 23(4 Suppl 8):58-63, 1996; Taylor et al., *Eur. J. Cancer* 33(10):1693-8, 1997). None of these or other proposed cytoprotectants such as oxonic acid for fluoropyrimidine toxicity, or prosaptide for paclitaxel PC12 cell toxicity, appears to function by a mechanism which renders normal replicating cells into a quiescent state.

What are needed are new effective cytoprotective agents which are effective in protecting animals, inclusive of humans, from the cytotoxic side effects of chemotherapeutic agents.

DEFINITIONS

General

The term "individual" or "subject", includes human beings and non-human animals. With respect to the disclosed radioprotective and cytoprotective methods, these terms refer, unless the context indicates otherwise, to an organism that is scheduled to incur, or is at risk for incurring, or has incurred, exposure to ionizing radiation or exposure to one or more cytotoxic chemotherapeutic agents.

The expression "effective amount" when used to describe therapy to a patient suffering from a proliferative disorder, refers to the amount of a compound according to Formula I, of a conjugate according to Formula I-L-Ab, that inhibits the growth of tumor cells or alternatively induces apoptosis of cancer cells, preferably tumor cells, resulting in a therapeutically useful and selective cytotoxic effect on proliferative cells when administered to a patient suffering from a cancer or other disorder which manifests abnormal cellular proliferation. The term "effective amount" is inclusive of amounts of a compound of the invention that may be metabolized to an active metabolite in an amount that inhibits the growth of tumor cells or induces apoptosis of cancer cells.

The term "antibody" as used herein, refers to a full-length immunoglobulin, or to an immunologically active portion of a full-length immunoglobulin, i.e., a molecule that contains an antigen binding site which immunospecifically binds an antigen of a target of interest, e.g., abnormally proliferating cells, particularly cancer cells. The antibody may be of any type, e.g., IgG, IgE, IgM, IgD, IgA, or IgY; of any class, e.g., IgG1, IgG2, IgG3, IgG4, IgA1 and IgA2, or subclass of immunoglobulin. The antibody may be derived from any species. Preferably, the antibody is human or murine, more preferably, human. Antibodies may include polyclonal, monoclonal, bispecific, human, humanized, chimeric, single chain antibodies, Fv, antibody fragments, e.g., Fab, F(ab'), F(ab)$_2$, and fragments produced by a Fab expression library.

The expression "humanized antibody" refers to an antibody that has its complementary determining regions (CDR's) derived from a non-human species immunoglobulin, and the remainder of the antibody molecule derived from a human immunoglobulin.

The term "chimeric antibody" refers to a monoclonal antibody comprising a variable region, i.e. binding region, from one source or species and at least a portion of a constant region derived from a different source or species.

The expression "humanized chimeric antibody" means a chimeric antibody in which at least the constant region is human-derived.

The expression "monospecific polyclonal antibody" means an antibody preparation comprising multiple antibody species having specificity for a single antigen.

The term "proliferative disorder" means a disorder wherein cells are made by the body at an atypically accelerated rate.

Radioprotection

As used herein, "ionizing radiation" is radiation of sufficient energy that, when absorbed by cells and tissues, induces formation of reactive oxygen species and DNA damage. This type of radiation includes X-Rays, gamma rays, and particle bombardment (e.g., neutron beam, electron beam, protons, mesons and others), and is used for medical testing and treatment, scientific purposes, industrial testing, manufacturing and sterilization, weapons and weapons development, and many other uses. Radiation is typically measured in units of absorbed dose, such as the rad or gray (Gy), wherein 1 rad=0.01 Gy, or in units of dose equivalence, such as the rem or sievert (Sv), wherein 1 rem=0.01 Sv.

The Sv is the Gy dosage multiplied by a factor that includes tissue damage done. For example, penetrating ionizing radiation (e.g., gamma and beta radiation) have a factor of about 1, so 1 Sv=~1 Gy. Alpha rays have a factor of 20, so 1 Gy of alpha radiation=20 Sv.

By "effective amount of ionizing radiation" is meant an amount of ionizing radiation effective in killing, or in reducing the proliferation, of abnormally proliferating cells in an individual. As used with respect to bone marrow purging, "effective amount of ionizing radiation" means an amount of ionizing radiation effective in killing, or in reducing the proliferation, of malignant cells in a bone marrow sample removed from an individual.

By "acute exposure to ionizing radiation" or "acute dose of ionizing radiation" is meant a dose of ionizing radiation absorbed by an individual in less than 24 hours. The acute dose may be localized, as in radiotherapy techniques, or may be absorbed by the individual's entire body. Acute doses are typically above 10,000 millirem (0.1 Gy), but may be lower.

By "chronic exposure to ionizing radiation" or "chronic dose of ionizing radiation" is meant a dose of ionizing radiation absorbed by an individual over a period greater than 24 hours. The dose may be intermittent or continuous, and may be localized or absorbed by the individual's entire body. Chronic doses are typically less than 10,000 millirem (0.1 Gy), but may be higher.

By "at risk of incurring exposure to ionizing radiation" is meant that an individual may intentionally, e.g., by scheduled radiotherapy sessions, or inadvertently be exposed to ionizing radiation in the future. Inadvertent exposure includes accidental or unplanned environmental or occupational exposure.

By "effective amount of a radioprotective compound" is meant an amount of compound according to Formula I effective to reduce or eliminate the toxicity associated with radiation in normal cells of the individual, and also to impart a direct cytotoxic effect to abnormally proliferating cells in the individual. As used with respect to bone marrow purging, "effective amount" of the radioprotective compound according to Formula I means an amount of compound effective to reduce or eliminate the toxicity associated with radiation in bone marrow removed from an individual, and also to impart a direct cytotoxic effect to malignant cells in the bone marrow removed from the individual.

Cytoprotection

By "mitotic phase cell cycle inhibitor" is meant a chemical agent whose mechanism of action includes inhibition of a cell's passage through any portion of the mitotic (M) phase of the cell cycle.

By "effective amount" of a mitotic phase cell cycle inhibitor or topoisomerase inhibitor is meant an amount of said inhibitor effective in killing or reducing the proliferation of cancer cells in a host animal.

By "effective amount" of the cytoprotective compound according to Formula I is meant an amount of compound effective to reduce the toxicity of the mitotic phase cell cycle inhibitor or topoisomerase inhibitor on normal cells of the animal.

The expression "cell cycle" refers to the usual description of cell development in terms of a cycle consisting of a series of phases—interphase and M (mitotic) phase—and the subdivision of interphase into the times when DNA synthesis is proceeding, known as the S-phase (for synthesis phase), and the gaps that separate the S-phase from mitosis. G1 is the gap after mitosis but before DNA synthesis starts, and G2 is the gap after DNA synthesis is complete before mitosis and cell division. Interphase is thus composed of successive G1, s and G2 phases, and normally comprises 90% or more of the total cell cycle time. The M phase consists of nuclear division (mitosis) and cytoplasmic division (cytokinesis). During the early part of the M phase, the replicated chromosomes condense from their extended interphase condition. The nuclear envelope breaks down, and each chromosome undergoes movements that result in the separation of pairs of sister chromatids as the nuclear contents are divided. Two new nuclear envelopes then form, and the cytoplasm divides to generate two daughter cells, each with a single nucleus. This process of cytokinesis terminates the M phase and marks the beginning of the interphase of the next cell cycle. The daughter cells resulting from completion of the M phase begin the interphase of a new cycle.

By "topoisomerase" is meant an enzyme that catalyzes the conversion of DNA from one topological form to another by introducing transient breaks in one or both strands of a DNA duplex.

By "topoisomerase inhibitor" is meant a chemical agent whose mechanism of action includes interfering with the function of a topoisomerase.

"Topological isomers" are molecules that differ only in their state of supercoiling. Type I topoisomerase cuts one strand of DNA and relaxes negatively supercoiled DNA, but does not act on positively supercoiled DNA. Type II topoisomerase cuts both strands of DNA and increases the degree of negative supercoiling in DNA.

Chemical

The term "alkyl", by itself or as part of another substituent, e.g., alkoxy, haloalkyl or aminoalkyl, means, unless otherwise stated, a saturated hydrocarbon radical having the number of carbon atoms designated (i.e. $C_1$-$C_6$ means one, two, three, four, five or six carbons) and includes straight, branched chain, cyclic and polycyclic groups. Examples include: methyl, ethyl, propyl, isopropyl, butyl, isobutyl, tert-butyl, pentyl, neopentyl, hexyl, cyclohexyl, norbornyl and cyclopropylmethyl. Preferred alkyl groups are —($C_1$-$C_6$) alkyl. Most preferred is —($C_1$-$C_3$)alkyl, particularly ethyl, methyl and isopropyl.

"Substituted alkyl" means alkyl, as defined above, substituted by one, two or three substituents preferably independently selected from the group consisting of halogen, —OH, —O($C_1$-$C_4$)alkyl, —$NH_2$, —$N(CH_3)_2$, —$CO_2H$, —$CO_2$($C_1$-$C_4$)alkyl, —$CF_3$, —$CONH_2$, —$SO_2NH_2$, —C(=NH)$NH_2$, —CN and —NO$_2$. More preferably, the substituted alkyl contains one or two substituents independently selected from halogen, —OH, NH$_2$, —N(CH$_3$)$_2$, trifluoromethyl and —CO$_2$H; most preferably, independently selected from halogen and —OH. Examples of substituted alkyls include, but are not limited to, 2,2-difluoropropyl, 2-carboxycyclopentyl and 3-chloropropyl.

The term "alkylene", by itself or as part of another substituent means, unless otherwise stated, a divalent straight, branched or cyclic chain hydrocarbon radical having the designated number of carbons. A substitution of another group on alkylene may be at any substitutable carbon, i.e., the expression —C(=O)(C$_1$-C$_4$ alkylene)R$^w$ would include, for example:

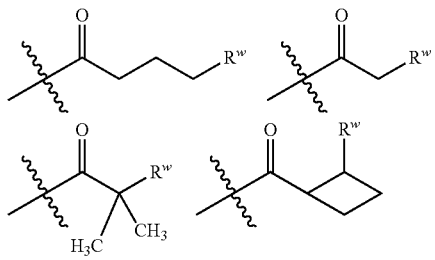

The term "alkoxy" employed alone or in combination with other terms means, unless otherwise stated, an alkyl group having the designated number of carbon atoms, as defined above, connected to the rest of the molecule via an oxygen atom, such as, for example, methoxy, ethoxy, 1-propoxy, 2-propoxy (isopropoxy) and the higher homologs and isomers. Preferred are (C$_1$-C$_3$)alkoxy, particularly ethoxy and methoxy.

The term "amine" or "amino" refers to radicals of the general formula —NRR', wherein R and R' are independently selected from hydrogen or a hydrocarbyl radical, or wherein R and R' combined form a heterocycle, Examples of amino groups include: —NH$_2$, methyl amino, diethyl amino, anilino, benzyl amino, piperidinyl, piperazinyl and indolinyl.

The term "aqueous base," as used for a hydrolysis reaction, refers to a base contained in a solvent medium that may be water or may be a mixture of water and at least one water-miscible organic solvent such as, for example, methanol, ethanol or tetrahydrofuran.

The term "aromatic" refers to a carbocycle or heterocycle having one or more polyunsaturated rings having aromatic character ((4n+2) delocalized π (pi) electrons).

The term "aryl" employed alone or in combination with other terms, means, unless otherwise stated, a carbocyclic aromatic system containing one or more rings (typically one, two or three rings) wherein such rings may be attached together in a pendent manner, such as a biphenyl, or may be fused, such as naphthalene. Examples include phenyl; anthracyl; and naphthyl. Preferred are phenyl and naphthyl, most preferred is phenyl.

The term "aryl-(C$_1$-C$_3$)alkyl" means a radical wherein a one to three carbon alkylene chain is attached to an aryl group, e.g., —CH$_2$CH$_2$-phenyl. Preferred is —(CH$_2$)aryl and —(CH (CH$_3$))aryl. The term "substituted aryl-(C$_1$-C$_3$)alkyl" means an aryl-(C$_1$-C$_3$)alkyl radical in which the aryl group is substituted. Preferred is substituted —(CH$_2$)aryl. Similarly, the term "heteroaryl(C$_1$-C$_3$)alkyl" means a radical wherein a one to three carbon alkylene chain is attached to a heteroaryl group, e.g., —CH$_2$CH$_2$-pyridyl. Preferred is —(CH$_2$)heteroaryl. The term "substituted heteroaryl-(C$_1$-C$_3$)alkyl" means a heteroaryl-(C$_1$-C$_3$)alkyl radical in which the heteroaryl group is substituted. Preferred is substituted —(CH$_2$) heteroaryl.

The term "arylene," by itself or as part of another substituent means, unless otherwise stated, a divalent aryl radical. Preferred are divalent phenyl radicals, particularly 1,4-divalent phenyl radicals.

The term "cycloalkyl" refers to ring-containing alkyl radicals. Examples include cyclohexyl, cyclopentyl, cyclopropyl methyl and norbornyl.

The expression "exocyclic double bond," unless otherwise stated, refers herein to a carbon-carbon double bond external to a chemical ring structure. Specifically, the expression refers to the carbon-carbon double bond in compounds of the invention, which is not contained in either the phenyl ring or the aromatic ring, Q, but rather is the double bond which is alpha to the aromatic ring, Q;

The terms "halo" or "halogen" by themselves or as part of another substituent, e.g., haloalkyl, mean, unless otherwise stated, a fluorine, chlorine, bromine, or iodine atom, preferably, fluorine, chlorine, or bromine, more preferably, fluorine or chlorine.

The term "haloalkyl" means, unless otherwise stated, an alkyl group as defined herein containing at least one halogen substituent and no substituent that is other than halogen. Multiple halogen substituents, up to substitution of all substitutable hydrogens on the alkyl group may be the same or different. Preferred haloalkyl groups include, for example, perfluoro(C$_1$-C$_4$)alkyl, gem-difluoro(C$_1$-C$_4$)alkyl, and chloro(C$_1$-C$_4$)alkyl. More preferred haloalkyl groups include, for example, —CF$_3$, —C$_2$F$_5$, —CH$_2$CF$_3$, —CHF$_2$, —CF$_2$CH$_3$, and —CH$_2$Cl.

The term "heteroalkyl" by itself or in combination with another term means, unless otherwise stated, a stable straight or branched chain radical consisting of the stated number of carbon atoms and one or two heteroatoms selected from the group consisting of O, N, and S, and wherein, in the sulfur heteroatoms may be optionally oxidized and the nitrogen heteroatoms may be optionally quaternized or oxidized. The oxygens bonded to oxidized sulfur or nitrogen may be present in addition to the one or two heteroatoms in the heteroalkyl group. The heteroatom(s) may be placed at any position of the heteroalkyl group, including between the rest of the heteroalkyl group and the fragment to which it is attached, as well as attached to the most distal carbon atom in the heteroalkyl group. Examples include: —O—CH$_2$—CH$_2$—CH$_3$, —CH$_2$—CH$_2$CH$_2$—OH, —CH$_2$—CH$_2$—NH—CH$_3$, —CH$_2$—SO$_2$—NH—CH$_3$, —CH$_2$—S—CH$_2$—CH$_3$, and —CH$_2$CH$_2$—S(=O)—CH$_3$. Up to two heteroatoms may be consecutive, such as, for example, —CH$_2$—NH—OCH$_3$, or —CH$_2$—CH$_2$—S—S—CH$_3$.

The term "heterocycle" or "heterocyclyl" or "heterocyclic" by itself or as part of another substituent means, unless otherwise stated, an unsubstituted or substituted, stable, mono- or multicyclic heterocyclic ring system which consists of carbon atoms and at least one heteroatom selected from the group consisting of N, O, and S, and wherein the nitrogen and sulfur heteroatoms may be optionally oxidized, and the nitrogen atom may be optionally quaternized. The heterocyclic system may be attached, unless otherwise stated, at any heteroatom or carbon atom which affords a stable structure.

The term "heteroaryl" or "heteroaromatic" refers to a heterocycle having aromatic character. A monocyclic heteroaryl group is a 5-, 6-, or 7-membered ring, examples of which are pyrrolyl, furyl, thienyl, pyridyl, pyrimidinyl and pyrazinyl. A polycyclic heteroaryl may comprise multiple aromatic rings or may include one or more rings which are partially saturated. Examples of polycyclic heteroaryl groups containing a partially saturated ring include tetrahydroquinolyl and 2,3-dihydrobenzofuryl. For compounds of Formula I, the attachment point on ring Q is understood to be on an atom which is part of an aromatic monocyclic ring or a ring component of a polycyclic aromatic which is itself an aromatic ring. The attachment point on ring Q may be a ring carbon or a ring nitrogen and includes attachment to form aromatic quaternary ammonium salts such as pyridinium.

Examples of non-aromatic heterocycles include monocyclic groups such as: aziridine, oxirane, thiirane, azetidine, oxetane, thietane, pyrrolidine, pyrroline, imidazoline, pyrazolidine, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin and hexamethyleneoxide.

Examples of heteroaryl groups include: pyridyl, pyrazinyl, pyrimidinyl, particularly 2- and 4-pyrimidyl, pyridazinyl, thienyl, furyl, pyrrolyl, particularly 2-pyrrolyl, imidazolyl, thiazolyl, oxazolyl, pyrazolyl, particularly 3- and 5-pyrazolyl, isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

Examples of polycyclic heterocycles include: indolyl, particularly 3-, 4-, 5-, 6- and 7-indolyl, indolinyl, quinolyl, tetrahydroquinolyl, isoquinolyl, particularly 1- and 5-isoquinolyl, 1,2,3,4-tetrahydroisoquinolyl, cinnolinyl, quinoxalinyl, particularly 2- and 5-quinoxalinyl, quinazolinyl, phthalazinyl, 1,8-naphthyridinyl, 1,4-benzodioxanyl, coumarin, dihydrocoumarin, benzofuryl, particularly 3-, 4-, 1,5-naphthyridinyl, 5-, 6- and 7-benzofuryl, 2,3-dihydrobenzofuryl, 1,2-benzisoxazolyl, benzothienyl, particularly 3-, 4-, 5-, 6-, and 7-benzothienyl, benzoxazolyl, benzthiazolyl, particularly 2-benzothiazolyl and 5-benzothiazolyl, purinyl, benzimidazolyl, particularly 2-benzimidazolyl, benztriazolyl, thioxanthinyl, carbazolyl, carbolinyl, acridinyl, pyrrolizidinyl, and quinolizidinyl.

a ring atom of an aromatic ring component of the polycyclic ring. For example, on the partially saturated heteroaromatic ring, 1,2,3,4-tetrahydroisoquinoline, attachment points are ring atoms at the 5-, 6-, 7- and 8-positions.

The aforementioned listing of heterocyclyl and heteroaryl moieties is intended to be representative, not limiting.

The term "hydrocarbyl" refers to any moiety comprising only hydrogen and carbon atoms. Preferred hydrocarbyl groups are $(C_1-C_{12})$hydrocarbyl, more preferred are $(C_1-C_7)$ hydrocarbyl, most preferred are benzyl and $(C_1-C_6)$alkyl.

The term "hydrocarbylene" by itself or as part of another substituent means, unless otherwise stated, a divalent moiety comprising only hydrogen and carbon atoms. A substitution of another group on hydrocarbylene may be at any substitutable carbon, i.e., the expression —$(C_1-C_6$ hydrocarbylene)$R^w$ would include, for example:

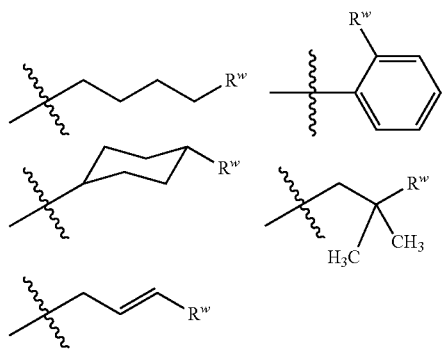

The expression "carboxy terminally-linked peptidyl residue" refers to a peptide radical as a substituent on a molecule of Formula I. The radical is bonded through the carboxyl functionality of a peptidyl residue to form a carboxamide, carboxylic ester or acyl sulfide (—S—C(=O)—). Scheme 1 illustrates how an exemplary peptidyl residue may be carboxy terminally-linked as a substituent in a compound according to Formula I.

Scheme 1

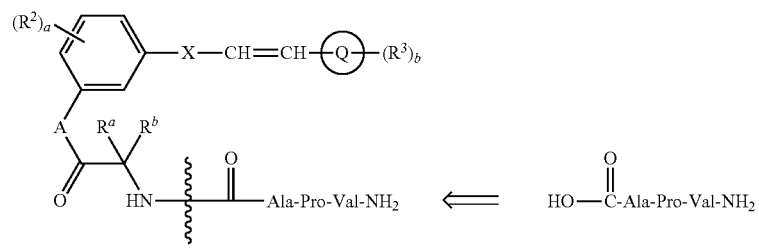

Carboxy terminally-linked peptidyl residue          Peptidyl residue

The term "heteroarylene," by itself or as part of another substituent means, unless otherwise stated, a divalent heteroaryl radical. Preferred are five- or six-membered monocyclic heteroarylene. More preferred are heteroarylene moieties comprising divalent heteroaryl rings selected from pyridine, piperazine, pyrimidine, pyrazine, furan, thiophene, pyrrole, thiazole, imidazole and oxazole.

For compounds of Formula I, when an aromatic or heteroaromatic ring is attached to a position and the ring comprises a polycyclic ring which is partially saturated, the attachment point on the aromatic or heteroaromatic ring is on The amino acid residues comprising the carboxy terminally-linked peptidyl residue may comprise natural or unnatural amino acids or a combination thereof. Unnatural amino acids are amino acids other than the twenty essential amino acids. One example of an unnatural amino acid is a D-amino acid, i.e., an amino acid having a stereochemistry opposite the stereochemistry of natural L-amino acids. Another example of an unnatural amino acid is an amino acid having a side chain that differs from the side chains occurring in the natural amino acids, for example α-ethyl glycine or α-phenyl glycine. A third example is an amino acid having a backbone variation. Examples of amino acid backbone variations include β-alanine and β-turn mimetics such as Freidinger's lactam. See Freidinger et al., Science, 1980, 210, 656, the entire disclosure of which is incorporated herein by reference. A fourth example of an unnatural amino acid is an amino acid having two α-substituents, e.g., α,α-dimethyl glycine.

The amino terminus of the carboxy terminally-linked peptidyl residue may be an unsubstituted amino group, or may be substituted. Substitutions on the amino terminus include mono- and di-($C_1$-$C_6$ alkyl), —C(═O)($C_1$-$C_6$ alkyl), —C(═O)O($C_1$-$C_7$)hydrocarbyl) and commonly employed nitrogen protecting groups such as tert-butoxycarbonyl (BOC), carbobenzyloxy (CBZ), 2,4-dimethoxybenzyl and fluorenylmethoxycarbonyl (FMOC).

The expression "amino terminally-linked peptidyl residue" refers to a peptide radical as a substituent on a compound according to Formula I. The radical is bonded through the terminal amino functionality of the peptidyl residue to form a carboxamide, sulfonamide, urea or thiourea. Scheme 2 illustrates how an exemplary peptidyl residue may be amino terminally-linked as a substituent in a compound according to Formula I.

bon may be any carbon in the chain having at least two substitutable hydrogens, including the terminal —$CH_3$ group and the proximal carbon through which the difluoro($C_x$-$C_y$) alkyl is bonded to the rest of the molecule. Examples include —$CH_2CF_2H$, —$(CH_2)_2$—$CF_2H$ and —$CF_2$—$CH_3$ and 3,3-difluorocyclohexyl.

The term "substituted" means that an atom or group of atoms has replaced hydrogen as the substituent attached to another group. For aryl and heteroaryl groups, the term "substituted" refers to any level of substitution, namely mono-, di-, tri-, tetra-, or penta-substitution, where such substitution is permitted. The substituents are independently selected, and substitution may be at any chemically accessible position.

The expression "isolated optical isomer" means a compound which has been substantially purified from the corresponding optical isomer(s) of the same formula. Preferably, the isolated isomer is at least about 80%, more preferably at least 90% pure, even more preferably at least 98% pure, most preferably at least about 99% pure, by weight.

The naming of compounds disclosed herein was done by employing the structure naming programs included in CHEMDRAW® software packages. The compounds, except for the α,β-unsaturated sulfonamides, were named using the Scheme 2

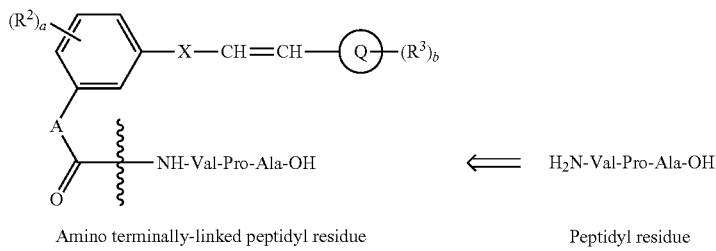

Amino terminally-linked peptidyl residue

Peptidyl residue

The carboxy terminus of the amino terminally-linked peptidyl residue may be a free carboxyl group or a salt thereof, or may be derivatized as an ester or amide. Suitable esters include alkyl, preferably ($C_1$-$C_6$) alkyl; and arylalkyl, preferably benzyl esters. Suitable amides include the primary amide and secondary and tertiary amides comprising one or two substituents on the amide nitrogen independently selected from ($C_1$-$C_3$)alkyl, preferably methyl or ethyl; aryl, preferably phenyl; and aryl($C_1$-$C_3$)alkyl groups, preferably benzyl or substituted benzyl.

As with the carboxy terminally-linked peptidyl residues, the amino acids comprising the amino terminally-linked peptidyl residue may comprise natural or unnatural amino acids or a combination thereof.

The term "($C_x$-$C_y$)perfluoroalkyl," wherein x<y, means an alkyl group with a minimum of x carbon atoms and a maximum of y carbon atoms, wherein all hydrogen atoms are replaced by fluorine atoms. Preferred is —($C_1$-$C_6$)perfluoroalkyl, more preferred is —($C_1$-$C_3$)perfluoroalkyl, most preferred is —$CF_3$.

The term "trifluoro($C_x$-$C_y$)alkyl" means an alkyl group with a minimum of x carbon atoms and a maximum of y carbon atoms, wherein the three hydrogen atoms on a terminal carbon (—$CH_3$) are replaced by fluorine atoms. Examples include —$CH_2CF_3$, —$(CH_2)_2$—$CF_3$ and —$CH(CH_3)$—$CF_3$.

The term "difluoro($C_x$-$C_y$)alkyl" means an alkyl group with a minimum of x carbon atoms and a maximum of y carbon atoms, wherein one carbon atom is geminally substituted with two fluorine atoms. The fluorine-substituted car- "Structure to Name" program within ChemDraw Ultra Version 8.0 (© 1985-2003, CambridgeSoft Corporation, 100 Cambridgepark Drive, Cambridge, Mass. 02140 USA). The structures of the α,β-unsaturated sulfonamides disclosed herein were named using the Nomenclator Plug-in for ChemDraw 7.0.

SUMMARY OF THE INVENTION

It is an object of the invention to provide compounds, conjugates, pharmaceutical compositions and therapeutic methods. The biologically active compounds are in the form of aromatic olefins, structurally linked via an optionally substituted methylene sulfone linker, an optionally substituted methylene sulfoxide linker, an optionally N-substituted sulfonamide linker, or an optionally N-substituted carboxamide linker, to a phenol or thiophenol functionality, or a derivative of such a phenol or thiophenol functionality.

It is an object of the invention to provide compounds, conjugates, compositions and methods for the treatment and/or prevention of cancer and other proliferative disorders.

It is an object of the invention to provide compounds and conjugates which are selective in killing tumor cells at therapeutically useful concentrations.

It is an object of the invention to provide compounds, conjugates, compositions and methods for inducing neoplastic cells to selectively undergo apoptosis.

It is a further object of this invention to provide compounds, conjugates, compositions and methods which enable prophylactic treatment of proliferative disorders.

It is a further object of this invention to provide compounds, compositions and methods for protecting normal cells and tissues from the cytotoxic and genetic effects of exposure to ionizing radiation, in individuals who have incurred, will in the future incur, or are at risk for incurring exposure to ionizing radiation. Exposure to ionizing radiation may occur in controlled doses during the treatment of cancer and other proliferative disorders. Alternatively, exposure to ionizing radiation may occur in uncontrolled doses beyond the norm accepted for the population at large during high risk activities or environmental exposures.

It is an object of the invention to provide compounds, compositions and methods for protecting individuals from the cytotoxic side effects of mitotic phase cell cycle inhibitors and topoisomerase inhibitors, used in the treatment of cancer and other proliferative disorders.

It is an object of the invention to provide a method for treating cancer or other proliferative disorders which reduces or eliminates cytotoxic effects on normal cells.

It is an object of the invention to enhance the effects of mitotic phase cell cycle inhibitors and topoisomerase inhibitors, used for the treatment of cancer or other proliferative disorders.

It is an object of the present invention to provide a therapeutic program for treating cancer or other proliferative disorder which includes administration of a cytoprotective compound prior to administration of a chemotherapeutic agent, which cytoprotective compound induces a reversible cycling quiescent state in non-tumored tissues.

It is an object of the invention to provide a method for safely increasing the dosage of mitotic phase cell cycle inhibitors and topoisomerase inhibitors, used in the treatment of cancer and other proliferative disorders.

I. Compounds According to Formula I

According to one aspect, the invention is directed to novel compounds according to Formula I:

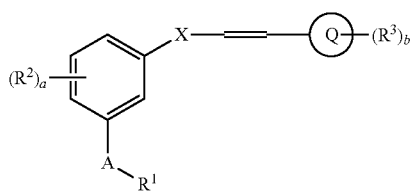

I wherein,

A is —S— or —O—;

$R^1$ is selected from the group consisting of —H; halo($C_1$-$C_6$)alkyl, preferably trifluoro($C_1$-$C_6$)alkyl, difluoro($C_1$-$C_6$)alkyl and chloro($C_1$-$C_6$)alkyl, more preferably trifluoro($C_1$-$C_3$)alkyl, difluoro($C_1$-$C_3$)alkyl and chloro($C_1$-$C_3$)alkyl, most preferably —$CF_3$, —$CHF_2$ and —$CH_2Cl$; —C(=O)$R^w$; —S(=O)$R^w$; —$SO_2R^w$; —($C_1$-$C_6$ hydrocarbylene)$R^z$, preferably —($C_1$-$C_6$)alkylene$R^z$, more preferably —($C_1$-$C_3$)alkylene-$R^z$; —P(=O)(O$R^v$)$_2$; —C($R^a$)($R^v$)—C(=O)—$R^n$; substituted and unsubstituted aryl, preferably substituted and unsubstituted phenyl; substituted and unsubstituted heteroaryl, preferably substituted and unsubstituted monocyclic heteroaryl; —Si[($C_1$-$C_6$)alkyl]$_3$, preferably, —Si($CH_3$)$_2$—C($CH_3$)$_3$; and —$CH_2CH_2$Si[($C_1$-$C_6$)alkyl]$_3$, preferably —$CH_2CH_2$Si($CH_3$)$_2$—C($CH_3$)$_3$ and —$CH_2CH_2$Si($CH_3$)$_3$;

each $R^v$ is independently selected from the group consisting of —H and —($C_1$-$C_7$)hydrocarbyl, preferably benzyl and —($C_1$-$C_6$)alkyl, more preferably benzyl and —($C_1$-$C_3$)alkyl, most preferably —$CH_3$ or —$C_2H_5$;

$R^w$ is selected from the group consisting of —($C_1$-$C_7$) hydrocarbyl, preferably —($C_1$-$C_6$)alkyl, more preferably —($C_1$-$C_3$)alkyl, most preferably —$CH_3$ or —$C_2H_5$; —N$R^v_2$; —O$R^v$; halo($C_1$-$C_3$ alkyl), preferably chloro($C_1$-$C_3$ alkyl) and trifluoro($C_1$-$C_3$ alkyl); —N$R^v$C$R^v$$R^a$—C(=O)—$R^n$; —C$R^v$$R^a$—N($R^v$)—$R^c$; substituted and unsubstituted aryl, preferably substituted and unsubstituted phenyl; substituted and unsubstituted aryl($C_1$-$C_3$)alkyl, preferably substituted and unsubstituted phenyl($C_1$-$C_3$)alkyl; substituted and unsubstituted heteroaryl, preferably substituted and unsubstituted monocyclic heteroaryl; substituted and unsubstituted heteroaryl($C_1$-$C_3$)alkyl, preferably substituted and unsubstituted monocyclic heteroaryl($C_1$-$C_3$)alkyl; substituted and unsubstituted heterocyclyl; substituted and unsubstituted heterocyclyl($C_1$-$C_3$)alkyl; alkylene)P(=O)(O$R^v$)$_2$; —($C_1$-$C_3$) perfluoroalkylene-N($CH_3$)$_2$; —($C_1$-$C_3$)alkylene-N(($C_1$-$C_3$)alkyl)$_2$; —($C_1$-$C_3$)alkylene-$N^+$(($C_1$-$C_3$)alkyl)$_3$; —($C_1$-$C_3$)alkylene-$N^+$($CH_2CH_2OH$)$_3$; —($C_1$-$C_4$alkylene)-C(=O)-halogen; —($C_1$-$C_4$)perfluoroalkylene-$CO_2R^v$; —($C_1$-$C_3$alkylene)C(=O)O$R^v$; and —($C_1$-$C_3$alkylene)OC(=O)—($C_1$-$C_3$ alkylene)C(=O)$R^v$;

$R^y$ is selected from the group consisting of —O$R^v$, —N$R^v_2$ and —($C_1$-$C_6$)alkyl;

$R^z$ is selected from the group consisting of —C(=O)$R^y$; —N$R^v$C$R^v$$R^a$—C(=O)—$R^n$; —N$R^v_2$; —O$R^v$; substituted and unsubstituted aryl, preferably substituted and unsubstituted phenyl; substituted and unsubstituted heteroaryl, preferably substituted and unsubstituted monocyclic heteroaryl; substituted and unsubstituted heterocyclyl($C_1$-$C_3$)alkyl, preferably unsubstituted heterocyclyl($C_1$-$C_3$)alkyl, more preferably unsubstituted 6-membered heterocyclyl($C_1$-$C_3$)alkyl, most preferably piperazin-1-yl($C_1$-$C_3$)alkyl and morpholin-1-yl($C_1$-$C_3$)alkyl; and —C(=O)($C_1$-$C_3$)alkyl;

each $R^a$ is independently selected from the group consisting of —H; —($C_1$-$C_6$)alkyl; —($C_1$-$C_6$)heteroalkyl, particularly —$CH_2SH$, —($CH_2$)$_2$C(=O)—$NH_2$, —$CH_2$—OH, —CH(OH)—$CH_3$, —($CH_2$)$_4$—$NH_2$, and —($CH_2$)$_2$—S—$CH_3$; —($CH_2$)$_3$—NH—C($NH_2$)(=NH); —$CH_2$C(=O)$NH_2$; —$CH_2$COOH; —($CH_2$)$_2$COOH; substituted and unsubstituted aryl, preferably substituted and unsubstituted phenyl; substituted and unsubstituted aryl($C_1$-$C_3$)alkyl, preferably substituted and unsubstituted phenyl($C_1$-$C_3$)alkyl, more preferably substituted and unsubstituted benzyl, particularly 4-hydroxybenzyl; substituted and unsubstituted heterocyclyl, preferably substituted and unsubstituted heteroaryl, more preferably substituted and unsubstituted monocyclic heteroaryl; and substituted and unsubstituted heterocyclyl($C_1$-$C_3$)alkyl, preferably substituted and unsubstituted heteroaryl($C_1$-$C_3$)alkyl, particularly —$CH_2$-(3-indolyl), more preferably substituted and unsubstituted monocyclic heteroaryl($C_1$-$C_3$)alkyl, most preferably substituted and unsubstituted monocyclic heteroaryl-$CH_2$—, particularly —$CH_2$-imidazolyl;

each $R^n$ is independently selected from the group consisting of —O$R^v$, —N$R^v_2$, and an N-terminally linked peptidyl residue containing from 1 to 3 amino acids in which the terminal carboxyl group of the peptidyl residue is present as a functional group selected from the group consisting of —$CO_2R^v$ and —C(=O)N$R^v_2$;

each $R^c$ is independently selected from the group consisting of —H and a carboxy terminally linked peptidyl residue containing from 1 to 3 amino acids in which the terminal amino group of the peptidyl residue is present as a functional group selected from the group consisting of —$NH_2$; —NHC(=O)($C_1$-$C_6$)alkyl; —NH($C_1$-$C_6$)alkyl; —NH($C_1$-$C_6$ alkyl)$_2$; and —NHC(=O)O(C$_1$-C$_7$)hydrocarbyl, preferably —NHC(=O)O(C$_1$-C$_6$)alkyl and —NHC(=O)O-benzyl;

Q is aryl or heteroaryl;

each R$^2$ and R$^3$ is independently selected from the group consisting of halogen; —(C$_1$-C$_7$)hydrocarbyl, preferably —(C$_1$-C$_6$)alkyl, more preferably —(C$_1$-C$_3$)alkyl, most preferably —CH$_3$ and —C$_2$H$_5$; —C(=O)R$^v$; —NR$^v_2$; —NHC(=O)R$^v$; —NHSO$_2$R$^v$; —NHR$^a$; —NHCR$^v$R$^a$C(=O)R$^n$; —NHSO$_2$R$^v$; —C(=O)OR$^v$; —C(=O)NHR$^v$; —NO$_2$; —CN; —OR$^v$; —P(=O)(OR$^v$)$_2$; —C(=NH)NH$_2$, dimethylamino(C$_2$-C$_6$ alkoxy); —NHC(=NR$^v$)NHR$^v$; —(C$_1$-C$_6$)haloalkyl, preferably trifluoro(C$_1$-C$_6$)alkyl and difluoro(C$_1$-C$_6$)alkyl, more preferably trifluoro(C$_1$-C$_3$)alkyl and difluoro(C$_1$-C$_3$)alkyl, most preferably —CF$_3$ and —CHF$_2$; and —(C$_1$-C$_6$)haloalkoxy, preferably trifluoro(C$_1$-C$_6$)alkoxy and difluoro(C$_1$-C$_6$)alkoxy, more preferably trifluoro(C$_1$-C$_3$)alkoxy and difluoro(C$_1$-C$_3$)alkoxy, most preferably —OCF$_3$ and —OCHF$_2$;

the two R$^v$ groups on —P(=O)(OR$^v$)$_2$ and —NR$^v_2$ may optionally together form a five- or six-membered heterocyclic ring, preferably a five-membered ring, which may further optionally be fused to an aryl or carbocyclic ring, preferably an aryl ring, more preferably a phenyl ring;

a is 0, 1, 2 or 3;

b is 0, 1, 2 or 3;

wherein the sum of a and b is preferably at least 1;

the configuration of the substituents on the exocyclic carbon-carbon double bond is either E- or Z-;

X is —C*H(R$^x$)Y— or —NR$^x$—Z—;

Y is —S(=O)— or —SO$_2$—;

Z is —C(=O)— or —SO$_2$—;

R$^x$ is selected from the group consisting of —H; —(C$_1$-C$_6$)alkyl, preferably —(C$_1$-C$_3$)alkyl, more preferably methyl and ethyl; and —C(=O)(C$_1$-C$_6$)alkyl, preferably —C(=O) (C$_1$-C$_3$)alkyl, more preferably acetyl and propionyl; and

* indicates that, when R$^x$ is other than —H, the configuration of the substituents on the designated carbon atom is (R)-, (S)- or any mixture of (R)- and (S)-; or a salt of such a compound, preferably a pharmaceutically acceptable salt of such a compound;

provided that:

(a) when A is —O— and R$^1$ is —H:
b is greater than 0; and
R$^3$ is other than (C$_1$-C$_6$)alkyl, —OH and —NO$_2$.

(b) when X is —NR$^x$—Z— and A is —O—:
R$^z$ is other than —C(=O)R$^y$, —NR$^v_2$ and unsubstituted aryl; and
R$^w$ is other than —(C$_1$-C$_6$)alkyl; and (c) when X is —C*H(R$^x$)Y— and A is —O—:
R$^1$ is other than halo(C$_1$-C$_6$)alkyl;
R$^z$ is other than —NR$^v_2$ and unsubstituted aryl; and
R$^w$ is other than —(C$_1$-C$_7$)hydrocarbyl.

According to one embodiment of the compounds of the invention:

R$^1$ is selected from the group consisting of —H; halo(C$_1$-C$_6$)alkyl, preferably trifluoro(C$_1$-C$_6$)alkyl, difluoro(C$_1$-C$_6$)alkyl and chloro(C$_1$-C$_6$)alkyl, more preferably trifluoro(C$_1$-C$_3$)alkyl, difluoro(C$_1$-C$_3$)alkyl and chloro(C$_1$-C$_3$)alkyl, most preferably —CF$_3$, —CHF$_2$ and —CH$_2$Cl; —C(=O)R$^w$; —S(=O)R$^w$; —SO$_2$R$^w$; —(C$_1$-C$_6$ hydrocarbylene)R$^z$, preferably —(C$_1$-C$_6$)alkyleneR$^z$, more preferably —(C$_1$-C$_6$)alkylene-COR$^y$; —P(=O)(OR$^v$)$_2$; —C(R$^a$)(R$^v$)—C(=O)—R$^n$; substituted and unsubstituted aryl, preferably substituted and unsubstituted phenyl; substituted and unsubstituted heteroaryl, preferably substituted and unsubstituted monocyclic heteroaryl; —Si[(C$_1$-C$_6$)alkyl]$_3$, preferably, —Si(CH$_3$)$_2$—C(CH$_3$)$_3$; and —CH$_2$CH$_2$Si[(C$_1$-C$_6$)alkyl]$_3$, preferably —CH$_2$CH$_2$Si(CH$_3$)$_2$—C(CH$_3$)$_3$ and —CH$_2$CH$_2$Si(CH$_3$)$_3$;

R$^w$ is selected from the group consisting of —(C$_1$-C$_7$) hydrocarbyl, preferably —(C$_1$-C$_6$)alkyl, more preferably —(C$_1$-C$_3$)alkyl, most preferably —CH$_3$ or —C$_2$H$_5$; —NR$^v_2$; —OR$^v$; halo(C$_1$-C$_3$ alkyl), preferably chloro(C$_1$-C$_3$ alkyl) and trifluoro(C$_1$-C$_3$ alkyl); —NR$^v$CR$^v$R$^a$—C(=O)—R$^n$; —CR$^v$R$^a$—N(R$^v$)—R$^c$; substituted and unsubstituted aryl, preferably substituted and unsubstituted phenyl; substituted and unsubstituted aryl(C$_1$-C$_3$)alkyl, preferably substituted and unsubstituted phenyl(C$_1$-C$_3$)alkyl; substituted and unsubstituted heteroaryl, preferably substituted and unsubstituted monocyclic heteroaryl; substituted and unsubstituted heteroaryl(C$_1$-C$_3$)alkyl, preferably substituted and unsubstituted monocyclic heteroaryl(C$_1$-C$_3$)alkyl; substituted and unsubstituted heterocyclyl; substituted and unsubstituted heterocyclyl(C$_1$-C$_3$)alkyl; alkylene)P(=O)(OR$^v$)$_2$; —(C$_1$-C$_3$) perfluoroalkylene-N(CH$_3$)$_2$; —(C$_1$-C$_3$)alkylene-N$^+$((C$_1$-C$_3$) alkyl)$_3$; —(C$_1$-C$_3$)alkylene-N$^+$(CH$_2$CH$_2$OH)$_3$; —(C$_1$-C$_4$alkylene)-C(=O)-halogen; —(C$_1$-C$_4$)perfluoroalkylene-CO$_2$R$^v$; —(C$_1$-C$_3$alkylene)C(=O)OR$^v$; and —(C$_1$-C$_3$alkylene)OC(=O)—(C$_1$-C$_3$ alkylene)C(=O)R$^y$;

R$^z$ is selected from the group consisting of —C(=O)R$^y$; —NR$^v$CR$^v$R$^a$—C(=O)—R$^n$; —NR$^v_2$; —OR$^v$; substituted and unsubstituted aryl, preferably substituted and unsubstituted phenyl; substituted and unsubstituted heteroaryl, preferably substituted and unsubstituted monocyclic heteroaryl; and —C(=O)(C$_1$-C$_3$)alkyl; and each R$^v$ is independently selected from the group consisting of —H and —(C$_1$-C$_7$)hydrocarbyl, preferably —(C$_1$-C$_6$) alkyl, more preferably —(C$_1$-C$_3$)alkyl, most preferably —CH$_3$ or —C$_2$H$_5$; and (c) when X is —C*H(R$^x$)Y— and A is —O—;

R$^1$ is other than halo(C$_1$-C$_6$)alkyl and unsubstituted aryl;

R$^z$ is other than —NR$^v_2$ and unsubstituted aryl; and

R$^w$ is other than —(C$_1$-C$_7$)hydrocarbyl.

According to some embodiments of compounds of Formula I, Q is aryl, preferably phenyl or naphthyl, more preferably phenyl.

According to other embodiments of compounds of Formula I, Q is heteroaryl, preferably monocyclic heteroaryl.

According to some embodiments of compounds of Formula I, there are provided compounds of Formula IE:

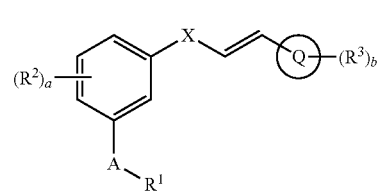

IE wherein the exocyclic carbon-carbon double bond is in the (E)-configuration.

According to other embodiments of compounds of Formula I, there are provided compounds of Formula IZ:

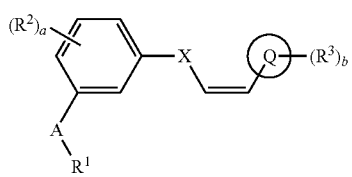

wherein the exocyclic carbon-carbon double bond is in the (Z)-configuration.

According to some embodiments of compounds of Formula I, $R^1$ is —H.

According to other embodiments of compounds of Formula I, $R^1$ is other than —H.

Preferably, when one or more of Q, $R^1$, $R^w$, $R^a$ or $R^z$ is a monocyclic heteroaryl group, the monocyclic heteroaryl group is independently selected from the group consisting of pyridyl, pyrazinyl, pyrimidinyl, pyridazinyl, thienyl, furyl, pyrrolyl, imidazolyl, thiazolyl, oxazolyl, pyrazolyl, isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

More preferably, when one or more of Q, $R^1$, $R^a$, $R^w$ or $R^z$ is a monocyclic heteroaryl group, the monocyclic heteroaryl group is independently selected from the group consisting of pyridyl, thienyl, furyl, pyrrolyl, imidazolyl, thiazolyl, oxazolyl, pyrazolyl, and isothiazolyl.

Most preferably, when one or more of Q, $R^1$, $R^a$, $R^w$ or $R^z$ is a monocyclic heteroaryl group, the monocyclic heteroaryl group is independently selected from the group consisting of pyridyl, thienyl, and furyl.

Preferably, when one or more of Q, $R^1$, $R^a$, $R^w$ or $R^z$ is a heteroaryl group other than a monocycyclic heteroaryl group, the heteroaryl group is selected from the group consisting of indolyl, quinolyl, isoquinolyl, cinnolinyl, quinoxalinyl, quinazolinyl, phthalazinyl, 1,8-naphthyridinyl, 1,4-benzodioxanyl, coumarin, benzofuryl, 1,2-benzisoxazolyl, benzothienyl, benzoxazolyl, benzthiazolyl, purinyl, benzimidazolyl, benztriazolyl, thioxanthinyl, carbazolyl, carbolinyl, acridinyl, pyrrolizidinyl, and quinolizidinyl.

More preferably, when one or more of Q, $R^1$, $R^a$, $R^w$ or $R^z$ is a heteroaryl group other than a monocycyclic heteroaryl group, the heteroaryl group is selected from the group consisting of indolyl, quinolyl, isoquinolyl, benzofuryl, benzothienyl, benzoxazolyl, benzthiazolyl, and benzimidazolyl.

Most preferably, when one or more of Q, $R^1$, $R^a$, $R^w$ or $R^z$ is a heteroaryl group other than a monocycyclic heteroaryl group, the heteroaryl group is selected from the group consisting of indolyl, quinolyl, isoquinolyl, benzofuryl and benzothienyl.

Preferably, substituted aryl and heteroaryl rings in $R^1$, $R^a$, $R^w$ and $R^z$ groups are mono-, di-, or tri-substituted, more preferably mono- or di-substituted by substituents selected from the group consisting of halogen; $(C_1$-$C_7)$hydrocarbyl, preferably benzyl and $(C_1$-$C_6)$alkyl, more preferably benzyl and $(C_1$-$C_3)$alkyl, most preferably benzyl, methyl and ethyl; —$NR^v{}_2$; —$NO_2$; —CN; heterocyclyl, preferably N-methylpiperazinyl, morpholinyl and thiomorpholinyl; —$OR^v$ and —$O(C_1$-$C_7)$hydrocarbyl, preferably —$O(C_1$-$C_6)$alkyl and —O-benzyl, more preferably —$O(C_1$-$C_3)$alkyl, most preferably benzyl, methoxy and ethoxy.

More preferably, substituted aryl and heteroaryl rings in $R^1$, $R^a$, $R^w$ and $R^z$ groups are mono-, di-, or tri-substituted, more preferably mono- or di-substituted by substituents selected from the group consisting of: chloro; fluoro; bromo; —$(C_1$-$C_6)$alkyl, preferably —$(C_1$-$C_3)$alkyl, more preferably methyl and ethyl; —$NH_2$; —$NO_2$; —CN; heterocyclyl, preferably N-methylpiperazinyl, morpholinyl and thiomorpholinyl; —OH; and —$O(C_1$-$C_6)$alkyl, preferably —$O(C_1$-$C_3)$alkyl, more preferably methoxy and ethoxy.

Most preferably, substituted aryl and heteroaryl rings in $R^1$, $R^a$, $R^w$ and $R^z$ groups are mono-, di- or tri-substituted, preferably mono- or di-substituted by substituents selected from the group consisting of chloro, fluoro, bromo, methyl, —$NO_2$, —CN, —OH, and methoxy.

Preferably, substituted heterocyclyl groups contained within $R^z$, $R^a$ and $R^w$ groups are mono-, di- or tri-substituted, more preferably mono- or di-substituted, by substituents selected from the group consisting of —$(C_1$-$C_7)$hydrocarbyl, preferably benzyl and —$(C_1$-$C_6)$alkyl, more preferably methyl, ethyl and benzyl; —C(=O)$(C_1$-$C_6)$alkyl, preferably —C(=O)$(C_1$-$C_3)$alkyl, more preferably acetyl; and —$(C_1$-$C_6)$perfluoroalkyl, preferably —$(C_1$-$C_3)$perfluoroalkyl, more preferably —$CF_3$.

More preferably, substituted heterocyclyl groups contained within $R^z$, $R^a$ and $R^w$ groups are mono- or di-substituted by substituents selected from the group consisting of —$(C_1$-$C_6)$alkyl, preferably methyl and ethyl, and —C(=O)$(C_1$-$C_3)$alkyl, preferably acetyl.

According to some embodiments of the invention, the sum of a and b is at least 2. According to other embodiments of the invention, the sum of a and b is at least 3. According to still other embodiments of the invention, the sum of a and b is at least 4. According to some embodiments of the invention, both a and b are at least 1. According to other embodiments of the invention, a is at least 1 and b is at least 2. According to other embodiments of the invention, b is at least 1 and a is at least 2. According to still other embodiments of the invention, both a and b are at least 2.

According to preferred embodiments of compounds of Formula I:

when b is 1, substitution of $R^3$ groups on Q is at the ortho- or para-position;

when b is 2, substitution of $R^3$ groups on Q is at either ortho- and para-positions, or at both ortho-positions; and when b is 3, substitution of $R^3$ groups on Q is at the para-position and at both ortho-positions.

Preferably, for compounds according to Formula I, Q is aryl; b is 1, 2 or 3; and each $R^2$ is —$OR^v$ or halogen, wherein multiple —$OR^v$ groups or halogens may be the same or different.

More preferably, for compounds according to Formula I, Q is phenyl; b is 2 or 3; and each $R^2$ is —$OR^v$, wherein multiple —$OR^v$ groups may be the same or different. Most preferably, each $R^2$ is —$OCH_3$.

The compounds of the invention further comprise embodiments of Formula I, described below in Formulae II, III, IV, V and VI. It is to be understood that the embodiments and preferred embodiments defined above for compounds according to Formula I are also embodiments and preferred embodiments of the compounds according to Formulae II, III, IV, V and VI, as described below.

II. Compounds According to Formula II

According to a one embodiment of the compounds according to Formula I, there are provided compounds according to Formula II:

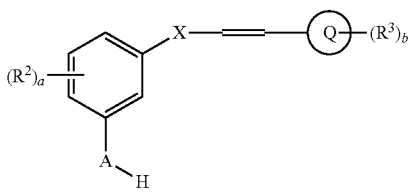

II wherein $R^2$, $R^3$, A, a, b, X and Q are as hereinbefore defined for compounds according to Formula I; or a salt thereof.

A. Compounds According to Formula IIA

According to one embodiment of the compounds according to Formula II, there are provided compounds according to Formula IIA:

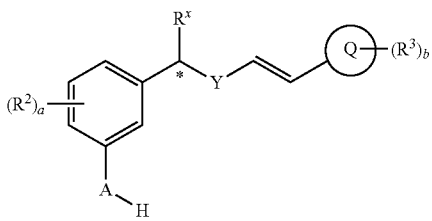

IIA wherein $R^2$, $R^3$, $R^x$, a, b, A, Y, Q and * are as hereinbefore defined for compounds according to Formula I, and the exocyclic carbon-carbon double bond is in the (E)-configuration.

According to some embodiments of compounds according to Formula IIA, $R^x$ is —H.

Preferred compounds according to Formula IIA include, for example: (E)-5-((2,4,6-trimethoxystyrylsulfonyl)methyl)-2-methoxyphenol; (E)-5-((2,4,6-trimethoxystyrylsulfonyl)methyl)-2-methoxybenzenethiol; (E)-5-((2,4,6-trimethoxystyrylsulfinyl)methyl)-2-methoxyphenol; (E)-5-((2,4,6-trimethoxystyrylsulfinyl)methyl)-2-methoxybenzenethiol; and salts thereof.

B. Compounds According to Formula IIB

According to another embodiment of the compounds according to Formula II, there are provided compounds according to Formula IIB:

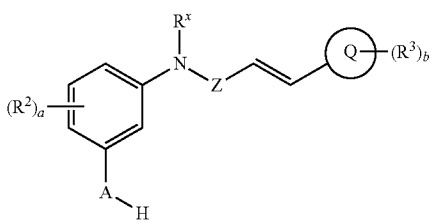

IIB wherein $R^2$, $R^3$, $R^x$, a, b, A, Z and Q are as hereinbefore defined for compounds according to Formula I, and the exocyclic carbon-carbon double bond is in the (E)-configuration.

According to a preferred embodiment of compounds according to Formula IIB, $R^x$ is —H.

Preferred compounds according Formula IIB include, for example: (E)-5-((2,4,6-trimethoxystyryl)sulfonamido)-2-methoxyphenol; (E)-5-((2,4,6-trimethoxystyryl)sulfonamido)-2-methoxybenzenethiol; (E)-N-(3-hydroxy-4-methoxyphenyl)-3-(2,4,6-trimethoxyphenyl)acryl-amide; (E)-N-(3-mercapto-4-methoxyphenyl)-3-(2,4,6-trimethoxyphenyl)-acrylamide; and salts thereof.

II. Compounds According to Formula III

According to another embodiment of the compounds according to Formula I, there are provided compounds according to Formula III:

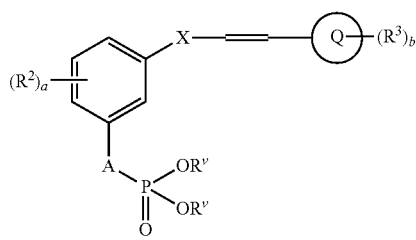

III wherein $R^2$, $R^3$, $R^v$, A, a, b, X and Q are as hereinbefore defined for compounds of Formula I; or a salt thereof.

A. Compounds According to Formula IIIA

According to a one embodiment of the compounds according to Formula III, there are provided compounds according to Formula IIIA:

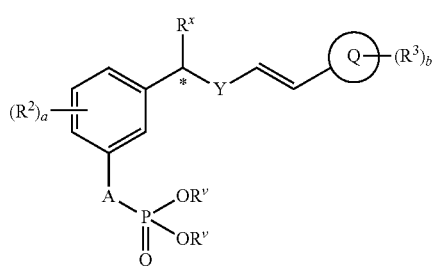

IIIA wherein $R^2$, $R^3$, $R^v$, $R^x$, a, b, A, Y, Q and * are as hereinbefore defined for compounds according to Formula I, and the exocyclic carbon-carbon double bond is in the (E)-configuration.

According to a preferred embodiment of compounds according to Formula IIIA, $R^x$ is —H.

Preferred compounds according to Formula IIIA include, for example: (E)-5-((2,4,6-trimethoxystyrylsulfonyl)methyl)-2-methoxyphenyl dihydrogen phosphate; (E)-5-((2,4,6-trimethoxystyrylsulfonyl)methyl)-2-methoxyphenyl dimethyl phosphate; (E)-5-((2,4,6-trimethoxystyrylsulfonyl)methyl)-2-methoxyphenyl diethyl phosphate; (E)-5-((2,4,6-trimethoxystyrylsulfonyl)-methyl)-2-methoxyphenyl dibenzyl phosphate; (E)-S-5-((2,4,6-trimethoxystyrylsulfonyl)methyl)-2-methoxyphenyl-O,O-dihydrogen phosphorothioate; (E)-S-5-((2,4,6-trimethoxystyrylsulfonyl)methyl)-2-methoxyphenyl-Q O-dimethyl phosphorothioate; (E)-S-5-((2,4,6-trimethoxystyrylsulfonyl)methyl)-2-methoxyphenyl-O,O-diethyl phosphorothioate; (E)-S-5-((2,4,6-trimethoxystyrylsulfonyl)methyl)-2-methoxyphenyl-O,O-dibenzyl phosphorothioate; (E)-5-((2,4,6-trimethoxystyrylsulfinyl)methyl)-2-methoxyphenyl dihydrogen phosphate; (E)-5-((2,4,6-trimethoxystyrylsulfinyl)methyl)-2-methoxyphenyl dimethyl phosphate; (E)-5-((2,4,6-trimethoxystyrylsulfinyl)methyl)-2-methoxyphenyl diethyl phosphate; (E)-5-((2,4,6-trimethoxystyrylsulfinyl)-methyl)-2-methoxyphenyl dibenzyl phosphate; (E)-S-5-((2,4,6-trimethoxystyrylsulfinyl)methyl)-2-methoxyphenyl-O, O-dihydrogen phosphorothioate; (E)-S-5-((2,4,6-trimethoxystyrylsulfinyl)methyl)-2-methoxyphenyl-O,O-dimethyl phosphorothioate; (E)-S-5-((2,4,6-trimethoxy-styrylsulfinyl)methyl)-2-methoxyphenyl-O,O-diethyl phosphorothioate; (E)-S-5-((2,4,6-trimethoxy-styrylsulfinyl)methyl)-2-methoxyphenyl-O,O-dibenzyl phosphorothioate; and salts thereof.

B. Compounds According to Formula IIIB

According to another embodiment of the compounds according to Formula III, there are provided compounds according to Formula IIIB:

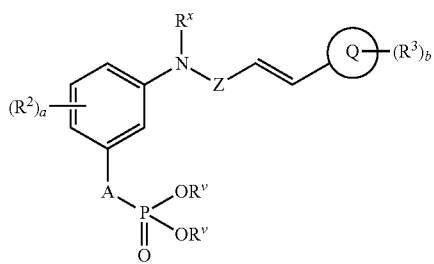

IIIB wherein $R^2$, $R^3$, $R^x$, $R^v$, a, b, A, Z and Q are as hereinbefore defined for compounds according to Formula I, and the exocyclic carbon-carbon double bond is in the (E)-configuration.

According to a preferred embodiment of compounds according to Formula IIIB, $R^x$ is —H.

Preferred compounds according to Formula IIIB include, for example: (E)-5-(2,4,6-trimethoxystyrylsulfonamido)-2-methoxyphenyl dihydrogen phosphate; (E)-5-(2,4,6-trimethoxystyrylsulfonamido)-2-methoxyphenyl dimethyl phosphate; (E)-5-(2,4,6-trimethoxystyrylsulfonamido)-2-methoxyphenyl diethyl phosphate; (E)-5-(2,4,6-trimethoxystyrylsulfonamido)-2-methoxyphenyl dibenzylphosphate; (E)-S-(5-(2,4,6-trimethoxystyryl-sulfonamido)-2-methoxyphenyl)-O,O-dihydrogen phosphorothioate; (E)-S-(5-(2,4,6-trimethoxystyryl-sulfonamido)-2-methoxyphenyl)-O,O-dimethyl phosphorothioate; (E)-S-(5-(2,4,6-trimethoxystyrylsulfonamido)-2-methoxyphenyl)-O,O-diethyl phosphorothioate; (E)-S-(5-(2,4,6-trimethoxystyrylsulfonamido)-2-methoxyphenyl)-O,O-dibenzyl phosphorothioate; 5-((E)-3-(2,4,6-trimethoxyphenyl)acrylamido)-2-methoxyphenyl dihydrogen phosphate; 5-((E)-3-(2,4,6-trimethoxyphenyl)-acrylamido)-2-methoxyphenyl dimethyl phosphate; 5-((E)-3-(2,4,6-trimethoxyphenyl)-acrylamido)-2-methoxyphenyl diethyl phosphate; 5-((E)-3-(2,4,6-trimethoxy-phenyl)acrylamido)-2-methoxyphenyl dibenzyl phosphate; S-5-((E)-3-(2,4,6-trimethoxyphenyl)acrylamido)-2-methoxyphenyl-O,O-dihydrogen phosphorothioate; S-5-((E)-3-(2,4,6-trimethoxyphenyl)acrylamido)-2-methoxyphenyl-O,O-dimethyl phosphorothioate; S-5-((E)-3-(2,4,6-trimethoxyphenyl)-acrylamido)-2-methoxyphenyl-O,O-diethyl phosphorothioate; S-5-((E)-3-(2,4,6-trimethoxyphenyl)acrylamido)-2-methoxyphenyl-O,O-dibenzyl phosphorothioate; and salts thereof.

IV. Compounds According to Formula IV

According to another embodiment of the compounds according to Formula I, there are provided compounds according to Formula IV:

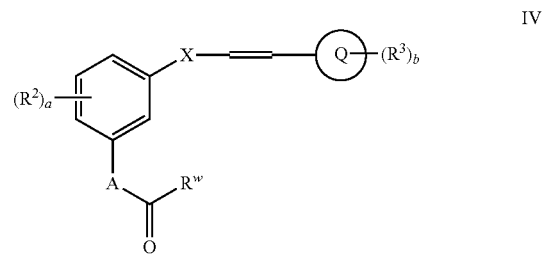

IV wherein $R^2$, $R^3$, $R^w$, A, a, b, X and Q are as hereinbefore defined for compounds according to Formula I; or a salt thereof.

A. Compounds According to Formula IVA

According to one embodiment of the compounds according to Formula IV, there are provided compounds according to Formula IVA:

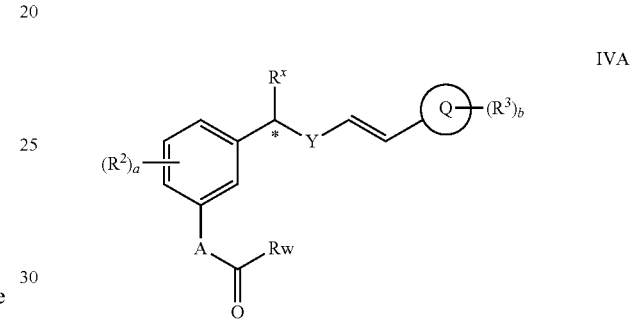

IVA wherein $R^2$, $R^3$, $R^x$, A, $R^w$, a, b, Y, Q and * are as hereinbefore defined for compounds according to Formula I, and the exocyclic carbon-carbon double bond is in the (E)-configuration.

According to a preferred embodiment of compounds according to Formula IVA, $R^x$ is —H.

Preferred compounds according to Formula IVA include, for example: (E)-2-((5-((2,4,6-trimethoxystyrylsulfonyl)methyl)-2-methoxyphenoxy)-carbonyl)acetic acid; (E)-5-((2,4,6-trimethoxystyrylsulfonyl)methyl)-2-methoxyphenyl-3,5-dinitrobenzoate; (E)-5-((2,4,6-trimethoxystyrylsulfonyl)-methyl)-2-methoxyphenyl-3,5-diaminobenzoate; (E)-5-((2,4,6-trimethoxystyrylsulfonyl)methyl)-2-methoxyphenyl-2-chloroacetate; (E)-5-((2,4,6-trimethoxystyrylsulfonyl)methyl)-2-methoxyphenyl-2-(4-methylpiperazin-1-yl)acetate; (E)-5-((2,4,6-trimethoxystyrylsulfonyl)methyl)-2-methoxyphenyl benzoate; (E)-5-((2,4,6-trimethoxystyrylsulfonyl)methyl)-2-methoxyphenyl-4-nitrobenzoate; (E)-5-((2,4,6-trimethoxystyrylsulfonyl)methyl)-2-methoxyphenyl-4-aminobenzoate; (E)-(R)-5-((2,4,6-trimethoxystyrylsulfonyl)methyl)-2-methoxyphenyl-2,6-diaminohexanoate; (E)-(R)-5-((2,4,6-trimethoxystyrylsulfonyl)methyl)-2-methoxyphenyl-2-amino-3-hydroxypropanoate; (E)-(S)-5-((2,4,6-trimethoxystyrylsulfonyl)methyl)-2-methoxyphenyl-2-amino-3-hydroxypropanoate; (E)-5-((2,4,6-trimethoxystyrylsulfonyl)methyl)-2-methoxy-phenyl carbamate; (E)-5-((2,4,6-trimethoxystyrylsulfonyl)methyl)-2-methoxyphenyl-2-(dimethylamino)-acetate; (E)-5-((2,4,6-trimethoxystyrylsulfonyl)methyl)-2-methoxyphenyl-4-(4-methylpiperazin-1-yl)benzoate; (E)-5-((2,4,6-trimethoxystyrylsulfonyl)methyl)-2-methoxyphenyl-2-hydroxyacetate; (E)-5-((2,4,6-trimethoxystyrylsulfonyl)-methyl)-2-methoxyphenyl-2-(pyridinium-1-yl)acetate; (E)-5-((2,4,6- trimethoxystyrylsulfonyl)methyl)-2-methoxyphenyl-2-acetoxyacetate; (E)-5-((2,4,6-trimethoxystyryl-sulfonyl)methyl)-2-methoxyphenyl-2-hydroxypropanoate; (E)-5-((2,4,6-trimethoxystyrylsulfonyl)methyl)-2-methoxyphenyl-2-(triethylammonium)-acetate; (E)-5-((2,4,6-trimethoxystyrylsulfonyl)methyl)-2-methoxyphenyl-2-(tris(2-hydroxyethyl)ammonium)acetate; (E)-5-((2,4,6-trimethoxystyryl-sulfonyl)methyl)-2-methoxyphenyl-2-hydroxy-2-methylpropanoate; (E)-5-((2,4,6-trimethoxystyrylsulfonyl)methyl)-2-methoxyphenyl-2-acetoxy-2-methylpropanoate; (E)-5-((2,4,6-trimethoxystyrylsulfonyl)methyl)-2-methoxy-phenyl-2,2,2-trifluoroacetate; (E)-3-((5-((2,4,6-trimethoxystyrylsulfonyl)-methyl)-2-methoxyphenoxy)-carbonyl)propanoic acid; (E)-5-((2,4,6-trimethoxystyrylsulfonyl)methyl)-2-methoxyphenyl-3-(chlorocarbonyl)-propanoate; (E)-5-((2,4,6-trimethoxystyrylsulfonyl)methyl)-2-methoxyphenyl 2-(3-carboxypropanoic)acetate; (E)-4-((5-((2,4,6-trimethoxystyrylsulfonyl)-methyl)-2-methoxyphenyl)-carbonyl)butanoic acid; (E)-((5-((2,4,6-trimethoxystyrylsulfonyl)methyl)-2-methoxyphenoxy)-carbonyl)methyl dihydrogen phosphate; (E)-5-((2,4,6-trimethoxystyrylsulfonyl)methyl)-2-methoxyphenyl methyl carbonate; (E)-5-((2,4,6-trimethoxystyrylsulfonyl)-methyl)-2-methoxyphenyl-2-acetoxypropanoate; (E)-5-((2,4,6-trimethoxystyrylsulfonyl)methyl)-2-methoxyphenyl methyl succinate; (E)-5-((2,4,6-trimethoxystyrylsulfonyl)methyl)-2-methoxyphenyl ethyl malonate; (E)-5-((2,4,6-trimethoxystyrylsulfonyl)methyl)-2-methoxyphenyl-2,2,3,3,3-pentafluoropropanoate; (E)-1-(5-((2,4,6-trimethoxystyrylsulfonyl)methyl)-2-methoxyphenyl)-3-methyl-2,2-difluoromalonate; (E)-3-((5-((2,4,6-trimethoxystyrylsulfonyl)methyl)-2-methoxyphenoxy)-carbonyl)-2,2,3,3-tetrafluoropropanoic acid; (E)-5-((2,4,6-trimethoxystyrylsulfonyl)methyl)-2-methoxyphenyl 2-aminoacetate; (E)-2-((5-((2,4,6-trimethoxystyrylsulfonyl)-methyl)-2-methoxyphenoxy)carbonyl)-2,2-difluoroacetic acid; (E)-5-((2,4,6-trimethoxystyrylsulfonyl)methyl)-2-methoxyphenyl-2-(dimethylamino)-2,2-difluoroacetate; 5-((2,4,6-trimethoxystyrylsulfonyl)methyl)-2-methoxyphenyl-2-(dimethylamino)acetate; (E)-2-((5-((2,4,6-trimethoxystyrylsulfinyl)methyl)-2-methoxyphenoxy)carbonyl)acetic acid; (E)-5-((2,4,6-trimethoxystyrylsulfinyl)-methyl)-2-methoxyphenyl-3,5-dinitrobenzoate; (E)-5-((2,4,6-trimethoxystyrylsulfinyl)methyl)-2-methoxyphenyl-3,5-diaminobenzoate; (E)-5-((2,4,6-trimethoxystyrylsulfinyl)methyl)-2-methoxyphenyl-2-chloroacetate; (E)-5-((2,4,6-trimethoxystyrylsulfinyl)methyl)-2-methoxyphenyl-2-(4-methylpiperazin-1-yl)acetate; (E)-5-((2,4,6-trimethoxystyrylsulfinyl)methyl)-2-methoxyphenyl benzoate; (E)-5-((2,4,6-trimethoxystyrylsulfinyl)methyl)-2-methoxyphenyl-4-nitrobenzoate; (E)-5-((2,4,6-trimethoxystyrylsulfinyl)methyl)-2-methoxyphenyl-4-aminobenzoate; (E)-(R)-5-((2,4,6-trimethoxystyrylsulfinyl)-methyl)-2-methoxyphenyl 2,6-diaminohexanoate; (E)-(R)-5-((2,4,6-trimethoxystyrylsulfinyl)methyl)-2-methoxyphenyl 2-amino-3-hydroxypropanoate; (E)-(S)-5-((2,4,6-trimethoxystyrylsulfinyl)methyl)-2-methoxyphenyl-2-amino-3-hydroxypropanoate; (E)-5-((2,4,6-trimethoxystyrylsulfinyl)methyl)-2-methoxyphenyl carbamate; (E)-5-((2,4,6-trimethoxystyrylsulfinyl)methyl)-2-methoxyphenyl 2-(dimethylamino)acetate; (E)-5-((2,4,6-trimethoxystyrylsulfinyl)-methyl)-2-methoxyphenyl 4-(4-methylpiperazin-1-yl)benzoate; (E)-5-((2,4,6-trimethoxystyrylsulfinyl)methyl)-2-methoxyphenyl-2-hydroxyacetate; (E)-5-((2,4,6-trimethoxystyrylsulfinyl)methyl)-2-methoxyphenyl-2-(pyridinium-1-yl)-acetate; (E)-5-((2,4,6-trimethoxystyrylsulfinyl)methyl)-2-methoxyphenyl-2-acetoxyacetate; (E)-5-((2,4,6-trimethoxystyrylsulfinyl)methyl)-2-methoxyphenyl-2-hydroxypropanoate; (E)-5-((2,4,6-trimethoxystyrylsulfinyl)-methyl)-2-methoxyphenyl-2-(triethylammonium)acetate; (E)-5-((2,4,6-trimethoxystyrylsulfinyl)methyl)-2-methoxyphenyl 2-(tris(2-hydroxyethyl)-ammonium)acetate; (E)-5-((2,4,6-trimethoxystyrylsulfinyl)methyl)-2-methoxy-phenyl 2-hydroxy-2-methylpropanoate; (E)-5-((2,4,6-trimethoxystyrylsulfinyl)-methyl)-2-methoxy-phenyl-2-acetoxy-2-methylpropanoate; (E)-5-((2,4,6-trimethoxystyrylsulfinyl)-methyl)-2-methoxyphenyl-2,2,2-trifluoroacetate; (E)-3-((5-((2,4,6-trimethoxystyrylsulfinyl)methyl)-2-methoxyphenoxy)-carbonyl)-propanoic acid; (E)-5-((2,4,6-trimethoxystyrylsulfinyl)methyl)-2-methoxy-phenyl-3-(chlorocarbonyl)-propanoate; (E)-5-((2,4,6-trimethoxystyrylsulfinyl)-methyl)-2-methoxyphenyl-2-(3-carboxypropanoic)acetate; (E)-4-((5-((2,4,6-trimethoxystyrylsulfinyl)-methyl)-2-methoxyphenoxy)-carbonyl)butanoic acid; (E)-((5-((2,4,6-trimethoxystyrylsulfinyl)methyl)-2-methoxyphenoxy)-carbonyl)-methyl dihydrogen phosphate; (E)-5-((2,4,6-trimethoxystyrylsulfinyl)methyl)-2-methoxyphenyl methyl carbonate; (E)-5-((2,4,6-trimethoxystyrylsulfinyl)-methyl)-2-methoxyphenyl-2-acetoxypropanoate; (E)-5-((2,4,6-trimethoxystyrylsulfinyl)methyl)-2-methoxyphenyl methyl succinate; (E)-5-((2,4,6-trimethoxystyrylsulfinyl)methyl)-2-methoxyphenyl ethyl malonate; (E)-5-((2,4,6-trimethoxystyrylsulfinyl)methyl)-2-methoxyphenyl-2,2,3,3,3-pentafluoropropanoate; (E)-1-(5-((2,4,6-trimethoxystyrylsulfinyl)methyl)-2-methoxyphenyl)-3-methyl-2,2-difluoromalonate; (E)-3-((5-((2,4,6-trimethoxystyrylsulfinyl)methyl)-2-methoxyphenoxy)-carbonyl)-2,2,3,3-tetrafluoropropanoic acid; (E)-5-((2,4,6-trimethoxystyrylsulfinyl)methyl)-2-methoxyphenyl-2-aminoacetate; (E)-2-((5-((2,4,6-trimethoxystyrylsulfinyl)-methyl)-2-methoxyphenoxy)-carbonyl)-2,2-difluoroacetic acid; (E)-5-((2,4,6-trimethoxystyrylsulfinyl)methyl)-2-methoxyphenyl-2-(dimethylamino)-2,2-difluoroacetate; 5-((2,4,6-trimethoxystyrylsulfinyl)methyl)-2-methoxyphenyl-2-(dimethylamino)acetate; and salts thereof.

B. Compounds According to Formula IVB

According to another embodiment of the compounds according to Formula IV, there are provided compounds according to Formula IVB:

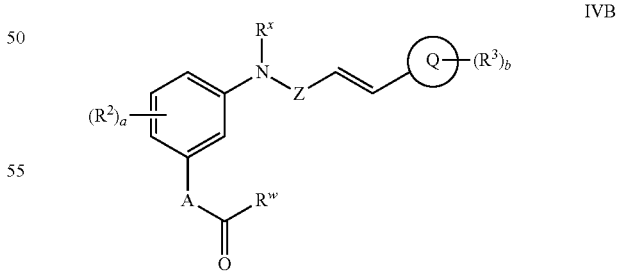

IVB wherein $R^2$, $R^3$, $R^x$, A, $R^w$, a, b, Z and Q are as hereinbefore defined for compounds according to Formula I, and the exocyclic carbon-carbon double bond is in the (E)-configuration.

According to a preferred embodiment of compounds according to Formula IVB, $R^x$ is —H.

Preferred compounds according to Formula IVB include, for example: 2-{[5-({[(1E)-2-(2,4,6-trimethoxyphenyl)vinyl]sulfonyl}amino)-2-methoxyphenyl]oxycarbonyl}acetic acid; 5-({[(1E)-2-(2,4,6-trimethoxyphenyl)-vinyl]sulfonyl}amino)-2-methoxyphenyl-3,5-dinitrobenzoate; 5-({[(1E)-2-(2,4,6-trimethoxyphenyl)vinyl]sulfonyl}amino)-2-methoxyphenyl-3,5-diaminobenzoate; 5-({[(1E)-2-(2,4,6-trimethoxyphenyl)vinyl]sulfonyl}amino)-2-methoxyphenyl-2-chloroacetate; 5-({[(1E)-2-(2,4,6-trimethoxyphenyl)-vinyl]-sulfonyl}amino)-2-methoxyphenyl 2-(4-methylpiperazinyl)acetate; 5-({[(1E)-2-(2,4,6-trimethoxyphenyl)vinyl]sulfonyl}amino)-2-methoxyphenyl benzoate; 5-({[(1E)-2-(2,4,6-trimethoxyphenyl)vinyl]sulfonyl}amino)-2-methoxyphenyl 4-nitrobenzoate; 5-({[(1E)-2-(2,4,6-trimethoxyphenyl)vinyl]-sulfonyl}amino)-2-methoxyphenyl-4-aminobenzoate; 5-({[(1E)-2-(2,4,6-trimethoxyphenyl)vinyl]-sulfonyl}amino)-2-methoxyphenyl-(2R)-2,6-diamino-hexanoate; 5-({[(1E)-2-(2,4,6-trimethoxyphenyl)vinyl]sulfonyl}amino)-2-methoxyphenyl-(2R)-2-amino-3-hydroxypropanoate; 5-({[(1E)-2-(2,4,6-trimethoxyphenyl)vinyl]-sulfonyl}amino)-2-methoxyphenyl-(2S)-2-amino-3-hydroxypropanoate; 5-({[(1E)-2-(2,4,6-trimethoxyphenyl)vinyl]sulfonyl}-amino)-2-methoxyphenyl carbamate; 5-({[(1E)-2-(2,4,6-trimethoxyphenyl)vinyl]sulfonyl}amino)-2-methoxyphenyl-2-(dimethylamino)-acetate; 5-({[(1E)-2-(2,4,6-trimethoxyphenyl)vinyl]sulfonyl}amino)-2-methoxyphenyl-4-(4-methylpiperazinyl)-benzoate; 5-({[(1E)-2-(2,4,6-trimethoxyphenyl)-vinyl]sulfonyl}amino)-2-methoxyphenyl-2-hydroxyacetate; 5-({[(1E)-2-(2,4,6-trimethoxyphenyl)vinyl]-sulfonyl}amino)-2-methoxyphenyl-2-pyrid-1-ylacetate; 5-({[(1E)-2-(2,4,6-trimethoxyphenyl)vinyl]sulfonyl}amino)-2-methoxyphenyl-2-acetyloxyacetate; 5-({[(1E)-2-(2,4,6-trimethoxyphenyl)vinyl]sulfonyl}-amino)-2-methoxyphenyl 2-hydroxypropanoate; 5-({[(1E)-2-(2,4,6-trimethoxy-phenyl)vinyl]sulfonyl}-amino)-2-methoxyphenyl-2-(triethylammonium)acetate; 5-({[(1E)-2-(2,4,6-trimethoxyphenyl)vinyl]sulfonyl}amino)-2-methoxyphenyl-2-[tris(2-hydroxyethyl)ammonium]acetate; 5-({[(1E)-2-(2,4,6-trimethoxy-phenyl)vinyl]-sulfonyl}amino)-2-methoxyphenyl 2-hydroxy-2-methylpropanoate; 5-({[(1E)-2-(2,4,6-trimethoxyphenyl)vinyl]sulfonyl}amino)-2-methoxyphenyl-2-acetyloxy-2-methylpropanoate; 5-({[(1E)-2-(2,4,6-trimethoxyphenyl)vinyl]sulfonyl}-amino)-2-methoxyphenyl-2,2,2-trifluoroacetate; 3-{[5-({[(1E)-2-(2,4,6-trimethoxyphenyl)vinyl]sulfonyl}-amino)-2-methoxyphenyl]oxycarbonyl}-propanoic acid; 5-({[(1E)-2-(2,4,6-trimethoxyphenyl)vinyl]sulfonyl}amino)-2-methoxyphenyl-3-(chlorocarbonyl)-propanoate; 3-[({[5-({[(1E)-2-(2,4,6-trimethoxyphenyl)vinyl]sulfonyl}amino)-2-methoxyphenyl]oxycarbonyl}-methyl)oxycarbonyl]propanoic acid; 4-{[5-({[(1E)-2-(2,4,6-trimethoxyphenyl)-vinyl]sulfonyl}amino)-2-methoxyphenyl]-oxycarbonyl}butanoic acid; 5-({[(1E)-2-(2,4,6-trimethoxyphenyl)vinyl]-sulfonyl}amino)-2-methoxyphenyl-2-(phosphonooxy)acetate; 5-({[(1E)-2-(2,4,6-trimethoxyphenyl)vinyl]sulfonyl}-amino)-2-methoxyphenyl methoxyformate; 5-({[(1E)-2-(2,4,6-trimethoxyphenyl)vinyl]sulfonyl}amino)-2-methoxyphenyl-2-acetyloxypropanoate; 5-({[(1E)-2-(2,4,6-trimethoxyphenyl)-vinyl]sulfonyl}amino)-2-methoxyphenyl methyl butane-1,4-dioate; 5-({[(1E)-2-(2,4,6-trimethoxyphenyl)vinyl]-sulfonyl}amino)-2-methoxyphenyl ethyl propane-1,3-dioate; 5-({[(1E)-2-(2,4,6-trimethoxyphenyl)vinyl]sulfonyl}amino)-2-methoxyphenyl-2,2,3,3,3-pentafluoropropanoate; 5-({[(1E)-2-(2,4,6-trimethoxyphenyl)vinyl]sulfonyl}-amino)-2-methoxyphenyl methyl 2,2-difluoropropane-1,3-dioate; 3-{[5-({[(1E)-2-(2,4,6-trimethoxyphenyl)vinyl]-sulfonyl}amino)-2-methoxyphenyl]-oxycarbonyl}-2,2,3,3,3-tetrafluoropropanoic acid; 5-({[(1E)-2-(2,4,6-trimethoxyphenyl)vinyl]sulfonyl}amino)-2-methoxy-phenyl-2-aminoacetate; 2-{[5-({[(1E)-2-(2,4,6-trimethoxyphenyl)vinyl]-sulfonyl}amino)-2-methoxyphenyl]-oxycarbonyl}-2,2-difluoroacetic acid; 5-({[(1E)-2-(2,4,6-trimethoxyphenyl)-vinyl]sulfonyl}amino)-2-methoxy-phenyl-2-(dimethylamino)-2,2-difluoroacetate; 5-((E)-3-(2,4,6-trimethoxyphenyl)-acrylamido)-2-methoxyphenyl-2-(carboxy)acetate; 5-((E)-3-(2,4,6-trimethoxyphenyl)acrylamido)-2-methoxyphenyl-3,5-dinitrobenzoate; 5-((E)-3-(2,4,6-trimethoxyphenyl)acrylamido)-2-methoxyphenyl-3,5-dinitrobenzoate; 5-((E)-3-(2,4,6-trimethoxyphenyl)acrylamido)-2-methoxyphenyl-2-chloroacetate; 5-((E)-3-(2,4,6-trimethoxyphenyl)-acrylamido)-2-methoxyphenyl-2-(4-methylpiperazin-1-yl)acetate; 5-((E)-3-(2,4,6-trimethoxyphenyl)acrylamido)-2-methoxyphenyl benzoate; 5-((E)-3-(2,4,6-trimethoxyphenyl)acrylamido)-2-methoxyphenyl-4-nitrobenzoate; 5-((E)-3-(2,4,6-trimethoxyphenyl)acrylamido)-2-methoxyphenyl-4-aminobenzoate; (R)-5-((E)-3-(2,4,6-trimethoxyphenyl)acrylamido)-2-methoxyphenyl-2,6-diaminohexanoate; (R)-5-((E)-3-(2,4,6-trimethoxyphenyl)acrylamido)-2-methoxyphenyl-2-amino-3-hydroxypropanoate; (S)-5-((E)-3-(2,4,6-trimethoxyphenyl)-acrylamido)-2-methoxyphenyl-2-amino-3-hydroxypropanoate; 5-((E)-3-(2,4,6-trimethoxyphenyl)acrylamido)-2-methoxyphenyl carbamate; 5-((E)-3-(2,4,6-trimethoxyphenyl)acrylamido)-2-methoxyphenyl-2-(dimethylamino)acetate; 5-((E)-3-(2,4,6-trimethoxyphenyl)acrylamido)-2-methoxyphenyl-4-(4-methylpiperazin-1-yl)benzoate; 5-((E)-3-(2,4,6-trimethoxyphenyl)acrylamido)-2-methoxyphenyl-2-hydroxyacetate; 5-((E)-3-(2,4,6-trimethoxyphenyl)-acrylamido)-2-methoxyphenyl 2-(pyridin-1-yl)acetate; 5-((E)-3-(2,4,6-trimethoxyphenyl)acrylamido)-2-methoxyphenyl-2-acetyloxyacetate; 5-((E)-3-(2,4,6-trimethoxyphenyl)acrylamido)-2-methoxyphenyl-2-hydroxypropanoate; 5-((E)-3-(2,4,6-trimethoxyphenyl)acrylamido)-2-methoxyphenyl-2-(N,N,N-triethylamino)acetate; 5-((E)-3-(2,4,6-trimethoxyphenyl)acrylamido)-2-methoxyphenyl-2-(N,N,N-tri-(2-hydroxyethyl)amino)acetate; 5-((E)-3-(2,4,6-trimethoxyphenyl)acrylamido)-2-methoxyphenyl-2-hydroxy-2-methyl-propanoate; 5-((E)-3-(2,4,6-trimethoxyphenyl)acrylamido)-2-methoxyphenyl-2-acetoxy-2-methyl-propanoate; 5-((E)-3-(2,4,6-trimethoxyphenyl)acrylamido)-2-methoxyphenyl-2,2,2-trifluoroacetate; 5-((E)-3-(2,4,6-trimethoxyphenyl)-acrylamido)-2-methoxyphenyl-3-carboxypropanoate; 5-((E)-3-(2,4,6-trimethoxyphenyl)acrylamido)-2-methoxyphenyl-3-(chlorocarbonyl)propanoate; 5-((E)-3-(2,4,6-trimethoxyphenyl)acrylamido)-2-methoxyphenyl-2-(3-carboxypropanoic)acetate; 5-((E)-3-(2,4,6-trimethoxyphenyl)acrylamido)-2-methoxyphenyl-(4-carboxybutyrate); 5-((E)-3-(2,4,6-trimethoxy-phenyl)acrylamido)-2-methoxyphenoxy)-carbonyl)methyl dihydrogen phosphate; 5-((E)-3-(2,4,6-trimethoxyphenyl)-acrylamido)-2-methoxyphenyl methyl carbonate; 5-((E)-3-(2,4,6-trimethoxyphenyl)acrylamido)-2-methoxyphenyl-2-acetoxypropanoate; 5-((E)-3-(2,4,6-trimethoxyphenyl)-acrylamido)-2-methoxyphenyl methyl succinate; 5-((E)-3-(2,4,6-trimethoxyphenyl)acrylamido)-2-methoxyphenyl ethyl malonate; 5-((E)-3-(2,4,6-trimethoxyphenyl)acrylamido)-2-methoxyphenyl-2,2,3,3,3-pentafluoropropanoate; 1-(5-((E)-3-(2,4,6-trimethoxyphenyl)acrylamido)-2-methoxyphenyl) 3-methyl-2,2-difluoromalonate; 5-((E)-3-(2,4,6-trimethoxyphenyl)acryl-amido)-2-methoxyphenyl-(3-carboxy-2,2,3,3-tetrafluorobutyrate); 5-((E)-3-(2,4,6-trimethoxyphenyl)

acrylamido)-2-methoxyphenyl-2-aminoacetate; 5-((E)-3-(2,4,6-trimethoxyphenyl)acrylamido)-2-methoxyphenyl-(2-carboxy-2,2-difluoroacetate); 5-((E)-3-(2,4,6-trimethoxyphenyl)acrylamido)-2-methoxyphenyl-2-(dimethylamino)-2,2-difluoroacetate; 5-((E)-3-(2,4,6-trimethoxyphenyl)acrylamido)-2-methoxyphenyl acetate; 5-({[(1E)-2-(2,4,6-trimethoxyphenyl)vinyl]sulfonyl}amino)-2-methoxyphenyl-2-(dimethylamino)-acetate; 5-((2,4,6-trimethoxystyrylsulfonyl)amino)-2-methoxyphenyl-2-(dimethylamino)acetate; and salts thereof.

V. Compounds According to Formula V

According to another embodiment of the compounds according to Formula I, there are provided compounds according to Formula V:

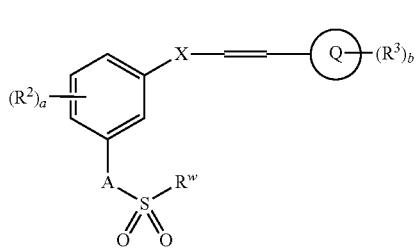

V wherein $R^2$, $R^3$, $R^w$, A, a, b, X and Q are as hereinbefore defined for compounds of Formula I; and salts thereof.

A. Compounds According to Formula VA

According to one embodiment of the compounds according to Formula V, there are provided compounds according to Formula VA:

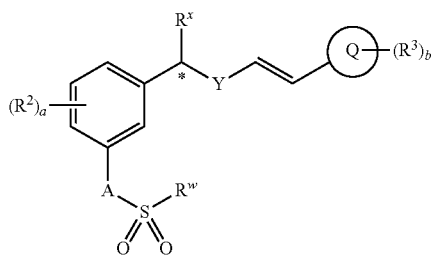

VA wherein $R^2$, $R^3$, $R^x$, $R^w$, A, a, b, Q and * are as hereinbefore defined for compounds according to Formula I, and the exocyclic carbon-carbon double bond is in the (E)-configuration.

According to a preferred embodiment of compounds according to Formula VA, $R^x$ is —H.

Preferred compounds according to Formula VA include, for example: (E)-5-((2,4,6-trimethoxystyrylsulfonyl)methyl)-2-methoxyphenyl carboxymethanesulfonate; (E)-5-((2,4,6-trimethoxystyrylsulfonyl)methyl)-2-methoxyphenyl-2,4-dinitrobenzenesulfonate; (E)-5-((2,4,6-trimethoxystyrylsulfonyl)-methyl)-2-methoxyphenyl-2,4-diaminobenzenesulfonate; (E)-5-((2,4,6-trimethoxystyrylsulfonyl)methyl)-2-methoxyphenyl trifluoromethanesulfonate; (E)-5-((2,4,6-trimethoxystyrylsulfonyl)methyl)-2-methoxyphenyl-4-methoxybenzenesulfonate; (E)-5-((2,4,6-trimethoxystyrylsulfinyl)methyl)-2-methoxyphenyl carboxymethanesulfonate; (E)-5-((2,4,6-trimethoxystyrylsulfinyl)-methyl)-2-methoxyphenyl-2,4-dinitrobenzenesulfonate; (E)-5-((2,4,6-trimethoxystyrylsulfinyl)methyl)-2-methoxyphenyl-2,4-diaminobenzenesulfonate; (E)-5-((2,4,6-trimethoxystyrylsulfinyl)methyl)-2-methoxyphenyl trifluoromethanesulfonate; (E)-5-((2,4,6-trimethoxystyrylsulfinyl)methyl)-2-methoxyphenyl-4-methoxybenzenesulfonate; (E)-5-((2,4,6-trimethoxystyrylsulfinyl)methyl)-2-methoxyphenyl-4-methylbenzenesulfonate; (E)-5-((2,4,6-trimethoxystyrylsulfinyl)methyl)-2-methoxyphenyl-4-methylbenzenesulfonate; and salts thereof.

B. Compounds According to Formula VB

According to another embodiment of the compounds according to Formula V, there are provided compounds according to Formula VB:

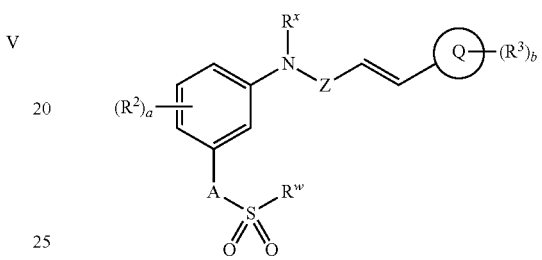

VB wherein $R^2$, $R^3$, $R^w$, $R^x$, a, b, A, Z and Q are as hereinbefore defined for compounds according to Formula I, and the exocyclic carbon-carbon double bond is in the (E)-configuration.

According to a preferred embodiment of compounds according to Formula VB, $R^x$ is —H.

Preferred compounds according to Formula VB include, for example: 2-{[5-({[(1E)-2-(2,4,6-trimethoxyphenyl)vinyl]sulfonyl}amino)-2-methoxyphenyl]oxysulfonyl}acetic acid; 5-({[(1E)-2-(2,4,6-trimethoxy-phenyl)vinyl]sulfonyl}amino)-2-methoxyphenyl-2,4-dinitrobenzenesulfonate; 5-({[(1E)-2-(2,4,6-trimethoxyphenyl)vinyl]sulfonyl}amino)-2-methoxyphenyl-2,4-diaminobenzenesulfonate; 5-({[(1E)-2-(2,4,6-trimethoxyphenyl)vinyl]-sulfonyl}amino)-2-methoxyphenyl-(trifluoromethyl)sulfonate; 5-({[(1E)-2-(2,4,6-trimethoxyphenyl)vinyl]sulfonyl}amino)-2-methoxyphenyl-4-methoxy-benzenesulfonate; 5-((E)-3-(2,4,6-trimethoxyphenyl)acrylamido)-2-methoxyphenylcarboxymethanesulfonate; 5-((E)-3-(2,4,6-trimethoxyphenyl)-acrylamido)-2-methoxyphenyltrifluoromethanesulfonate; 5-((E)-3-(2,4,6-trimethoxyphenyl)acrylamido)-2-methoxyphenyl-2,4-dinitrobenzenesulfonate; 5-((E)-3-(2,4,6-trimethoxyphenyl)acrylamido)-2-methoxyphenyl-2,4-diaminobenzenesulfonate; 5-((E)-3-(2,4,6-trimethoxyphenyl)acrylamido)-2-methoxyphenyl-4-methoxy-benzenesulfonate; 5-((E)-3-(2,4,6-trimethoxyphenyl)acrylamido)-2-methoxyphenyl-4-methylbenzenesulfonate; (E)-5-((2,4,6-trimethoxystyrylsulfonyl)-amino)-2-methoxyphenyl-4-methylbenzenesulfonate; and salts thereof.

VI. Compounds According to Formula VI

According to another embodiment of the compounds according to Formula I, there are provided compounds according to Formula VI:

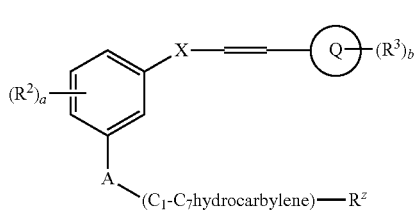

wherein $R^2$, $R^3$, $R^z$, A, a, b, X and Q are as hereinbefore defined for compounds of Formula I; or a salt thereof.

A. Compounds of Formula VIA

According to one embodiment of the compounds according to Formula VI, there are provided compounds according to Formula VIA:

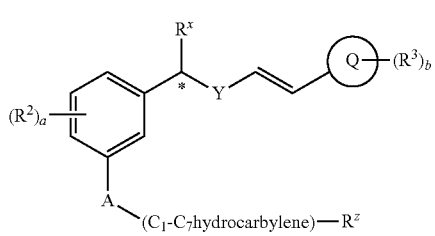

wherein $R^2$, $R^3$, $R^x$, $R^z$, a, b, A, Y, Q and * are as hereinbefore defined for compounds according to Formula I, and the exocyclic carbon-carbon double bond is in the (E)-configuration.

According to a preferred embodiment of compounds according to Formula VIA, $R^x$ is —H.

Preferred compounds according to Formula VIA include, for example: (E)-2-(5-((2,4,6-trimethoxystyrylsulfonyl)methyl)-2-methoxyphenoxy)-acetic acid; (E)-2-(5-((2,4,6-trimethoxystyrylsulfonyl)methyl)-2-methoxyphenoxy)-propanoic acid; (E)-4-(5-((2,4,6-trimethoxystyrylsulfonyl)-methyl)-2-methoxyphenoxy)-butanoic acid; (E)-3-(5-((2,4,6-trimethoxystyryl-sulfonyl)methyl)-2-methoxyphenoxy)-propanoic acid; (E)-2-(5-((2,4,6-trimethoxystyrylsulfinyl)-methyl)-2-methoxyphenoxy)-acetic acid; (E)-2-(5-((2,4,6-trimethoxystyrylsulfinyl)methyl)-2-methoxyphenoxy)-propanoic acid; (E)-4-(5-((2,4,6-trimethoxystyrylsulfinyl)methyl)-2-methoxyphenoxy)-butanoic acid; (E)-3-(5-((2,4,6-trimethoxystyrylsulfinyl)methyl)-2-methoxyphenoxy)-propanoic acid; (E)-4-(2-(5-((2,4,6-trimethoxystyrylsulfonyl)methyl)-2-methoxyphenoxy)ethyl)-morpholine; (E)-4-(2-(5-((2,4,6-trimethoxystyrylsulfinyl)methyl)-2-methoxyphenoxy)ethyl)morpholine; and salts thereof.

B. Compounds According to Formula VIB

According to another embodiment of the compounds according to Formula VI, there are provided compounds according to Formula VIB:

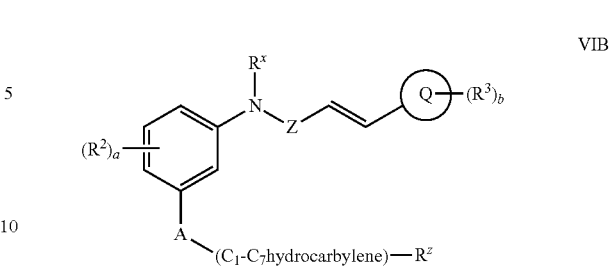

wherein $R^2$, $R^3$, $R^x$, $R^z$, a, b, A, Z and Q are as hereinbefore defined, and the exocyclic carbon-carbon double bond is in the (E)-configuration.

According to a preferred embodiment of compounds according to Formula VIB, $R^x$ is —H.

Preferred compounds according to Formula VIB include, for example: 2-[5-({[(1E)-2-(2,4,6-trimethoxyphenyl)vinyl]sulfonyl}amino)-2-methoxyphenoxy]acetic acid; 2-[5-({[(1E)-2-(2,4,6-trimethoxyphenyl)vinyl]sulfonyl}-amino)-2-methoxyphenoxy]propanoic acid; 4-[5-({[(1E)-2-(2,4,6-trimethoxyphenyl)vinyl]-sulfonyl}amino)-2-methoxyphenoxy]butanoic acid; 3-[5-({[(1E)-2-(2,4,6-trimethoxyphenyl)vinyl]sulfonyl}amino)-2-methoxyphenoxy]-propanoic acid; (E)-N-(3-(carboxymethoxy)-4-methoxyphenyl)-3-(2,4,6-trimethoxyphenyl)acrylamide; (E)-N-(3-(1-carboxyethoxy)-4-methoxyphenyl)-3-(2,4,6-trimethoxyphenyl)-acrylamide; (E)-N-(3-(3-carboxypropoxy)-4-methoxyphenyl)-3-(2,4,6-trimethoxyphenyl)acrylamide; (E)-N-(3-(2-carboxyethoxy)-4-methoxyphenyl)-3-(2,4,6-trimethoxyphenyl)acrylamide; (E)-N-(3-(2-morpholinoethoxy)-4-methoxyphenyl)-3-(2,4,6-trimethoxyphenyl)acrylamide; (E)-4-(2-(5-((2,4,6-trimethoxystyrylsulfonyl)amino)-2-methoxyphenoxy)ethyl)-morpholine; and salts thereof.

VII. Novel Synthetic Intermediates

The invention is also directed to intermediates, useful in the preparation of certain compounds of Formula I.

A. Intermediates in the Preparation of Formula IE Compounds Wherein X is —C*$R^x$Y—

According to some embodiments of the invention, there are provided synthetic intermediates useful in the preparation of compounds of Formula IE:

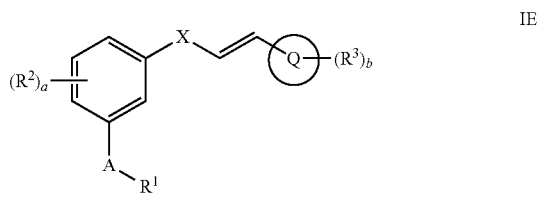

The synthetic intermediate compounds have the Formula VII:

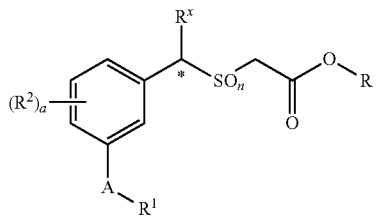

or a salt of such a compound,
wherein:
R$^1$, R$^2$, R$^x$, A, a and * are as defined herein for compounds of Formula I; n is 0, 1 or 2; and R is —H or —(C$_1$-C$_6$)alkyl; or a salt thereof;
provided that:
R$^1$ is other than halo(C$_1$-C$_6$)alkyl;
R$^z$ is other than —NR$^v_2$ and unsubstituted aryl; and
R$^w$ is other than —(C$_1$-C$_7$)hydrocarbyl.

According to one embodiment of compounds of Formula VII, A is —O—. According to another embodiment of compounds of Formula VII, R$^x$ is —H.

Compounds according to Formula VII, wherein n is 1, include, for example:
2-(3-hydroxy-4-methoxybenzylsulfinyl)acetic acid; 2-(3-mercapto-4-methoxybenzylsulfinyl)acetic acid; 2-(3-tert-butyldimethylsilyloxy-4-methoxybenzylsulfinyl)acetic acid; 2-(3-((tert-butyldimethylsilyl)sulfanyl)-4-methoxybenzylsulfinyl)acetic acid; O-2-methoxy-5-(carboxymethylsulfinylmethyl)phenyl dihydrogen phosphate; O-2-methoxy-5-(carboxymethylsulfinylmethyl)phenyl dimethyl phosphate; O-2-methoxy-5-(carboxymethylsulfinylmethyl)phenyl diethyl phosphate; O-2-methoxy-5-(carboxymethylsulfinylmethyl)phenyl dibenzyl phosphate; S-2-methoxy-5-(carboxymethylsulfinylmethyl)phenyl-O,O-dihydrogen phosphorothioate; S-2-methoxy-5-(carboxymethylsulfinylmethyl)phenyl-O,O-dimethyl phosphorothioate; S-2-methoxy-5-(carboxymethylsulfinylmethyl)phenyl-O,O-diethyl phosphorothioate; S-2-methoxy-5-(carboxymethylsulfinylmethyl)phenyl-O,O-dibenzyl phosphorothioate; and salts thereof.

Compounds according to Formula VII, wherein n is 2, include, for example:
2-(3-hydroxy-4-methoxybenzylsulfonyl)acetic acid; 2-(3-mercapto-4-methoxybenzylsulfonyl)acetic acid; 2-(3-tert-butyldimethylsilyloxy-4-methoxybenzylsulfonyl)acetic acid; 2-(3-((tert-butyldimethylsilyl)sulfanyl)-4-methoxybenzylsulfonyl)acetic acid; O-2-methoxy-5-(carboxymethylsulfonyl-methyl)-phenyl dihydrogen phosphate; O-2-methoxy-5-(carboxymethyl-sulfonylmethyl)phenyl dimethyl phosphate; O-2-methoxy-5-(carboxymethylsulfonylmethyl)phenyl diethyl phosphate; O-2-methoxy-5-(carboxymethylsulfonylmethyl)phenyl dibenzyl phosphate; S-2-methoxy-5-(carboxymethylsulfonylmethyl)phenyl-O,O-dihydrogen phosphorothioate; S-2-methoxy-5-(carboxymethylsulfonylmethyl)phenyl-O,O-dimethyl phosphorothioate; S-2-methoxy-5-(carboxymethylsulfonylmethyl)phenyl-O,O-diethyl phosphorothioate; S-2-methoxy-5-(carboxymethylsulfonylmethyl)phenyl-O,O-dibenzyl phosphorothioate; and salts thereof.

Compounds of Formula VII, wherein n is 1 or 2, and R is —(C$_1$-C$_6$)alkyl include, for example, methyl and ethyl esters of the exemplary compounds of Formula VII listed above.

Compounds of Formula VII, wherein R is —H, may be prepared, for example, by: (1) reacting the compound according to Formula VII, wherein R is —(C$_1$-C$_6$)alkyl, under conditions capable of hydrolyzing a carboxylic acid ester to the corresponding carboxylic acid, preferably in an aqueous base such as, for example aqueous lithium hydroxide, aqueous sodium hydroxide or aqueous potassium hydroxide; and (2) isolating a compound according to Formula VII, wherein R is —H, from the reaction mixture.

Compounds of Formula VII, wherein n is 1 and A is —O—, may be prepared, for example, by: (1) reacting an intermediate of Formula VII, wherein n is 0 and A is —O—, or a salt thereof, with an oxidizing agent capable of oxidizing a sulfide to a sulfoxide; and (2) isolating a compound according to Formula VII, wherein n is 1, from the reaction products.

Compounds of Formula VII, wherein n is 2 and A is —O— may be prepared, for example, by (1) reacting either (a) an intermediate of Formula VII, wherein n is 0 and A is —O—, with an oxidizing agent capable of oxidizing a sulfide to a sulfone; or (b) an intermediate of Formula VII, wherein n is 1 and A is —O—, with an oxidizing agent capable of oxidizing a sulfoxide to a sulfone; and (2) isolating a compound according to Formula VII, wherein n is 2, from the reaction products.

Compounds according to Formula VII, wherein n is 0, include, for example: 2-(3-hydroxy-4-methoxybenzylsulfanyl)acetic acid; 2-(3-tert-butyldimethylsilyloxy-4-methoxybenzylsulfanyl)acetic acid; O-2-methoxy-5-(carboxymethylsulfanylmethyl)phenyl dihydrogen phosphate; O-2-methoxy-5-(carboxymethylsulfanylmethyl)phenyl dimethyl phosphate; O-2-methoxy-5-(carboxymethylsulfanylmethyl)phenyl diethyl phosphate; O-2-methoxy-5-(carboxymethylsulfanylmethyl)phenyl dibenzyl phosphate; and salts thereof.

Compounds of Formula VII, wherein n is 0, and R is —(C$_1$-C$_6$)alkyl include, for example, methyl and ethyl esters of the exemplary compounds of Formula VII listed above.

Compounds of Formula VII, wherein n is 1 or 2 and A is —S— or —O—, or salts thereof, may be prepared, for example, by
(a) reacting a compound according to Formula IX:

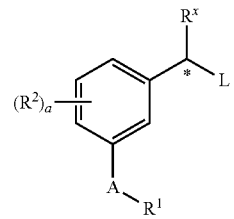

wherein:
R$^1$, R$^2$, R$^x$, A, a and * are as defined for compounds of Formula VII, provided that R$^1$ is other than —H; and L is a leaving group, preferably selected from the group consisting of halogen, tosyl, nosyl, trifyl, and mesyl;
with a compound according to Formula X:

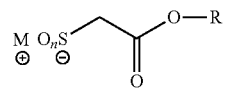

wherein:

R is —(C$_1$-C$_6$)alkyl, preferably methyl or ethyl; n is 1 or 2; and M$^+$ is a counterion, preferably selected from the group consisting of alkali metals, preferably lithium, sodium and potassium; alkaline earth metals, preferably calcium and magnesium; and transition metals, preferably, zinc, iron, nickel, copper, titanium, manganese, cadmium and tin.

(b) isolating a compound according to Formula VII, wherein, n is 1 or 2, and R is —(C$_1$-C$_6$)alkyl, from the reaction products;

(c) reacting the compound according to Formula VII, isolated in step (b), under conditions capable of hydrolyzing a carboxylic acid ester to the corresponding carboxylic acid, preferably in an aqueous base such as, for example, aqueous lithium hydroxide, aqueous sodium hydroxide or aqueous potassium hydroxide; and (d) isolating a compound according to Formula VII, wherein n is 1 or 2, from the reaction mixture.

The Formula VII compounds, wherein n is 0 and A is —S— or —O—, may be prepared, for example, by (a) reacting a compound according to Formula IX:

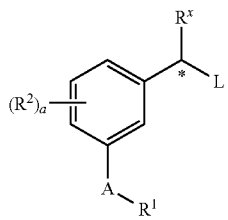

IX with a compound according to Formula VIII:

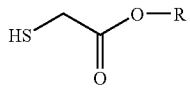

VIII wherein, R is —H or —(C$_1$-C$_6$)alkyl, or a salt thereof;

(b) isolating a compound according to Formula VII, wherein n is 0, from the reaction products;

(c) optionally, if R is —(C$_1$-C$_6$)alkyl, reacting the compound according to Formula VII isolated in step (b) under conditions capable of hydrolyzing a carboxylic acid ester to the corresponding carboxylic acid, preferably in an aqueous base such as, for example aqueous lithium hydroxide, aqueous sodium hydroxide or aqueous potassium hydroxide; and (d) isolating a compound according to Formula VII, wherein n is 0, from the reaction mixture.

Preferred compounds according to Formula IX include, for example: 5-(bromomethyl)-2-methoxyphenoxy(tert-butyl) dimethylsilane; 5-(chloromethyl)-2-methoxyphenoxy(tert-butyl)dimethylsilane; (5-(bromomethyl)-2-methoxyphenylthio)(tert-butyl)dimethylsilane; (5-(chloromethyl)-2-methoxyphenylthio)-(tert-butyl)dimethylsilane; 5-(bromomethyl)-2-methoxyphenyl dihydrogen phosphate; 5-(chloromethyl)-2-methoxyphenyl dihydrogen phosphate; 5-(bromomethyl)-2-methoxyphenyl dimethyl phosphate; 5-(chloromethyl)-2-methoxyphenyl dimethyl phosphate; 5-(bromomethyl)-2-methoxyphenyl diethyl phosphate; 5-(chloromethyl)-2-methoxyphenyl diethyl phosphate; 5-(chloromethyl)-2-methoxyphenyl dibenzyl phosphate; 5-(bromomethyl)-2-methoxyphenyl dibenzyl phosphate; S-5-(chloromethyl)-2-methoxyphenyl-O,O-dihydrogen phosphorothioate; S-5-(bromomethyl)-2-methoxyphenyl-O,O-dihydrogen phosphorothioate; O,O-dibenzyl-S-5-(chloromethyl)-2-methoxyphenyl phosphorothioate; O,O-dibenzyl-S-5-(bromomethyl)-2-methoxyphenyl phosphorothioate; O,O-dimethyl-S-5-(chloromethyl)-2-methoxyphenyl phosphorothioate; O,O-dimethyl-S-5-(bromomethyl)-2-methoxyphenyl phosphorothioate; O,O-diethyl-S-5-(chloromethyl)-2-methoxyphenyl phosphorothioate; O,O-diethyl-S-5-(bromomethyl)-2-methoxyphenyl phosphorothioate; and salts thereof.

Compounds according to Formula VIII include, for example, 2-mercaptoacetic acid, methyl 2-mercaptoacetate, and ethyl 2-mercaptoacetate.

B. Intermediates in the Preparation of Compounds of Formula IZ Wherein X is —C*R$^x$—Y—

The invention is also directed to synthetic intermediates, useful in the preparation of certain compounds of Formula IZ.

The synthetic intermediate compounds have the Formula XI:

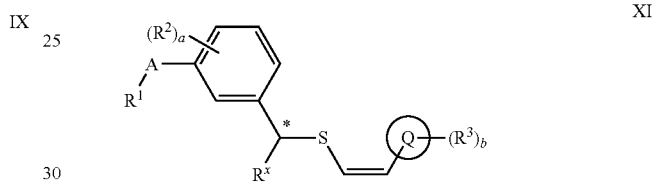

XI wherein R$^1$ R$^2$, R$^x$, A, a and * are as defined herein for compounds of Formula IX; and A is —O—.

According to one embodiment of compounds of Formula XI, R$^x$ is —H.

Compounds according to Formula XI include, for example, (Z)-5-((2,4,6-trimethoxystyrylthio)methyl)-2-methoxyphenol; (Z)-5-((2,4,6-trimethoxystyrylthio)-methyl)-2-methoxyphenyl dihydrogen phosphate; (Z)-5-((2,4,6-trimethoxystyrylthio)methyl)-2-methoxyphenyl dimethyl phosphate; (Z)-5-((2,4,6-trimethoxystyrylthio)methyl)-2-methoxyphenyl diethyl phosphate; (Z)-5-((2,4,6-trimethoxystyrylthio)methyl)-2-methoxyphenyl dibenzyl phosphate; and salts thereof.

The invention is also directed to synthetic intermediates, useful in the preparation of certain compounds of the invention.

The synthetic intermediate compounds have the Formula XII:

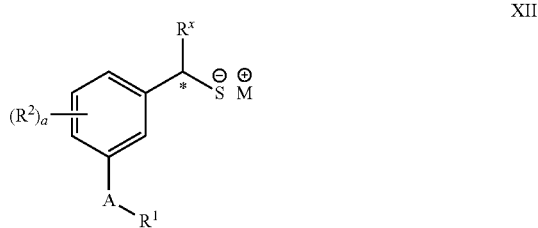

XII wherein:

R$^1$, R$^2$, R$^x$, A, a and * are as defined herein for compounds of Formula IX; and M$^+$ is a counterion, preferably selected from the group consisting of alkali metals, more preferably lithium, sodium and potassium; alkaline earth metals, more preferably calcium and magnesium; and transition metals, more preferably, zinc, iron, nickel, copper, titanium, manganese, cadmium and tin.

According to one embodiment of compounds of Formula XII, $R^x$ is —H.

Compounds according to Formula XII include, for example, alkali metal and alkaline earth metal salts of: (2-methoxy-5-mercaptomethylphenoxy)(tert-butyl)dimethylsilane; (3-(tert-butyldimethylsilyloxy)-4-methoxyphenyl)-methanethiol; (3-((tert-butyldimethylsilyl)sulfanyl)-4-methoxyphenyl)methanethiol; 2-methoxy-5-(mercaptomethyl) phenyl dimethyl phosphate; 2-methoxy-5-(mercaptomethyl) phenyl diethyl phosphate; 2-methoxy-5-(mercaptomethyl) phenyl dibenzyl phosphate; 2-methoxy-5-(mercaptomethyl)-phenyl dihydrogen phosphate; 5-(mercaptomethyl)-2-methoxyphenyl diethyl phosphate; 5-(mercaptomethyl)-2-methoxyphenyl dibenzyl phosphate; S-5-(mercaptomethyl)-2-methoxyphenyl-O,O-dimethyl phosphorothioate; S-5-(mercaptomethyl)-2-methoxyphenyl-O,O-diethyl phosphorothioate; S-5-(mercaptomethyl)-2-methoxyphenyl-O,O-dibenzyl phosphorothioate; and S-5-(mercaptomethyl)-2-methoxyphenyl-O,O-dihydrogen phosphorothioate.

C. Intermediates in the Preparation of Compounds of Formula IE Wherein X is —$NR^x$—Z—.

The invention is also directed to synthetic intermediates, useful in the preparation of certain sulfonamide and propenamide compounds of Formula IE, in particular, in the preparation of α,β-unsaturated sulfonamide and propenamide compounds of Formulae IIB, IIIB, IVB, VB and VIB.

The synthetic intermediate compounds have the Formula XIII:

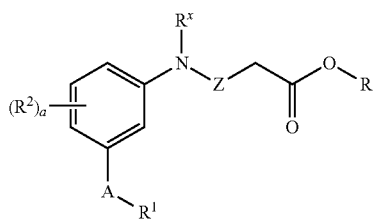

XIII wherein $R^1$, $R^2$, $R^x$, A, Z and a are as defined herein for compounds of Formula I, and R is —H or —($C_1$-$C_6$)alkyl; or a salt thereof.

According to one embodiment of compounds of Formula XIII, A is —O—.

According to another embodiment of compounds of Formula XIII, $R^x$ is —H.

A compound according to Formula XIII wherein R is —H, or a salt of such a compound, may be prepared by:

(a) reacting a corresponding compound according to Formula XIII, wherein R is —($C_1$-$C_6$)alkyl under conditions capable of hydrolyzing a carboxylic acid ester to the corresponding carboxylic acid, preferably in an aqueous base such as, for example aqueous lithium hydroxide, aqueous sodium hydroxide or aqueous potassium hydroxide; and (b) isolating from the reaction products a compound according to Formula XIII, wherein R is —H.

According to one embodiment of the compounds of Formula XII, there is provided a compound according to Formula XIIIA:

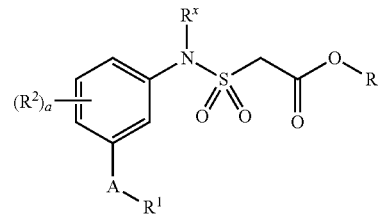

XIIIA wherein $R^1$, $R^2$, $R^x$, A, a and R are as hereinbefore defined for compounds of Formula XIII; or a salt of such a compound.

According to another embodiment of the compounds of Formula XII, there is provided a compound according to Formula XIIIB:

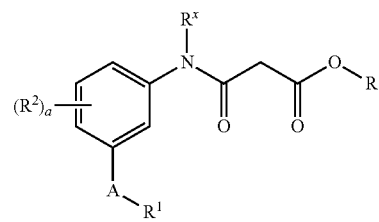

XIIIB wherein $R^1$, $R^2$, $R^x$, a, R and A are as hereinbefore defined for compounds of Formula XII; or a salt of such a compound.

Compounds according to Formula XIIIA include, for example: N-(3-hydroxy-4-methoxyphenyl)carboxymethylsulfonamide; N-(3-mercapto-4-methoxyphenyl)carboxymethylsulfonamide; N-(3-tert-butyldimethylsilyloxy-4-methoxyphenyl)carboxymethylsulfonamide; 3-((tert-butyldimethylsilyl)-sulfanyl)-4-methoxyphenylsulfamoylacetic acid; 2-(3-tert-butyldimethylsilyloxy-4-methoxyphenylsulfamoyl)acetic acid; 2-methoxy-5-(N-(carboxymethyl)sulfamoyl)phenyl phosphate; 2-methoxy-5-(N-(carboxymethyl)sulfamoyl) phenyl dimethyl phosphate; 2-methoxy-5-(N-(carboxymethyl)sulfamoyl)phenyl diethyl phosphate; 2-methoxy-5-(N-(carboxymethyl)sulfamoyl)phenyl dibenzyl phosphate; S-(2-methoxy-5-(N-(carboxymethyl)-sulfamoyl)phenyl) phosphorothioate; S-(2-methoxy-5-(N-(carboxymethyl)-sulfamoyl)phenyl)-O,O-dimethyl phosphorothioate; S-(2-methoxy-5-(N-(carboxymethyl)sulfamoyl)phenyl)-O,O-diethyl phosphorothioate; S-(2-methoxy-5-(N-(carboxymethyl)sulfamoyl)phenyl)-O,O-dibenzyl phosphorothioate; and salts thereof.

Compounds according to Formula XIIIB include, for example: 2-(3-mercapto-4-methoxyphenylcarbamoyl)acetic acid; 2-(3-hydroxy-4-methoxyphenylcarbamoyl)acetic acid; 3-((tert-butyldimethylsilyl)sulfanyl)-4-methoxyphenylcarbamoylacetic acid; 2-(3-tert-butyldimethylsilyloxy-4-methoxyphenylcarbamoyl)acetic acid; 5-N-(carboxymethyl)carbamoyl-2-methoxyphenyl phosphate; 5-N-(carboxymethyl)carbamoyl-2-methoxyphenyl dimethyl phosphate; 5-N-(carboxymethyl)carbamoyl-2-methoxyphenyl diethyl phosphate; 5-N-(carboxymethyl)carbamoyl-2-methoxyphenyl dibenzyl phosphate; S-5-N-(carboxymethyl)carbamoyl-2-methoxyphenyl phosphorothioate; S-5-N-(carboxymethyl) carbamoyl-2-methoxyphenyl dimethyl phosphorothioate; S-5-N-(carboxymethyl)carbamoyl-2-methoxyphenyl diethyl phosphorothioate; S-5-N-(carboxymethyl)carbamoyl-2-methoxyphenyl dibenzyl phosphorothioate; and salts thereof.

Formula XIII compounds and salts thereof, wherein R is —(C$_1$-C$_6$)alkyl, may be prepared, for example, by (a) reacting a compound according to Formula XIV:

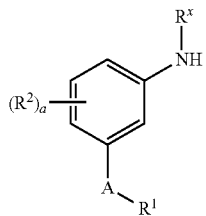

XIV wherein R$^1$ R$^2$, R$^x$, A and a are as defined herein for compounds of Formula XII; or a salt thereof; with a compound according to Formula XV:

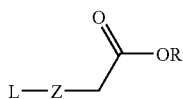

XV wherein Z is as herein defined for compounds of Formula I; R is —(C$_1$-C$_6$)alkyl; and L is a leaving group, preferably selected from halogen, more preferably chloro; and (b) isolating a compound according to Formula XIII, or a salt thereof, from the reaction mixture.

VIII. Processes of Preparing Compounds of Formula I

According to another aspect of the invention, processes for preparing compounds according to Formula I are provided.

A. Preparation of compounds of Formula IE, Wherein X is —CH*R$^x$—Y—

According to one embodiment, a compound according to Formula IE:

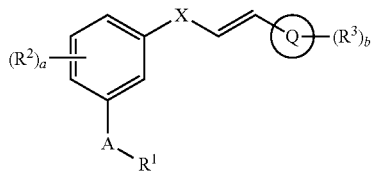

IE or a salt thereof,
wherein R$^1$, R$^2$, R$^3$, A, Q, a and b are as defined herein for compounds of Formula I, and X is —CH*R$^x$—Y—, may be prepared by:

(a) reacting a compound according to Formula VII:

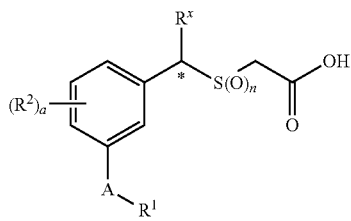

VII or a salt thereof, wherein n is 1 or 2, with a compound according to Formula XVI:

XVI (b) isolating a compound according to Formula IE, or a salt thereof, from the reaction products.

B. Preparation of compounds of Formula IZ, Wherein X is —CH*R$^x$—Y—

(i) Preparation of Compounds Wherein A is —O—

According to one embodiment of the invention, a compound according to Formula IZ:

IZ or a salt of such a compound;
wherein R$^1$, R$^2$, R$^3$, A, Q, a and b are as defined herein for Formula I compounds wherein X is —CH*R$^x$—Y—, Y is —S(=O)—; and A is —O—, may be prepared by:

(a) reacting a compound according to Formula XI:

XI or a salt thereof, with an oxidizing agent capable of oxidizing a sulfide to a sulfoxide; and (b) isolating a compound according to Formula IZ, or a salt thereof, from the reaction products.

According to another embodiment, a compound according to Formula IZ, or a salt thereof, wherein R$^1$, R$^2$, R$^3$, A, Q, a and b are as defined herein, X is —CH*R$^x$—Y—, Y is —SO$_2$—, and A is —O—, may be prepared by either:

(a) reacting a compound according to Formula XI, or a salt thereof, with an oxidizing agent capable of oxidizing a sulfide to a sulfone; and (b) isolating a compound according to Formula IZ, or a salt thereof, from the reaction products; or by (a) reacting a compound according to Formula IZ, or a salt thereof, wherein R$^1$, R$^2$, R$^3$, A, Q, a and b are as defined herein; X is —CH*R$^x$—Y—, Y is —S(=O)—, and A is —O—; with an oxidizing agent capable of oxidizing a sulfoxide to a sulfone; and (b) isolating a compound according to Formula IZ, or a salt thereof, from the reaction products.

The Formula XI compound may be prepared, for example, by:

(a) reacting a compound according to Formula XII:

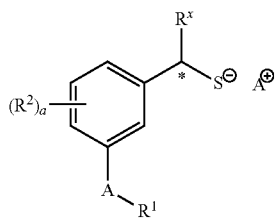

with a compound according to Formula XVII:

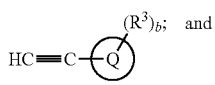

(b) isolating a compound according to Formula XI from the reaction products.

C. Preparation of Compounds of Formula IE, Wherein X is —NR$^x$—Z—.

According to another embodiment of the invention, a process for preparing a compound according to Formula IE, or a salt thereof, wherein X is —NR$^x$—Z—, is provided, comprising:

(a) reacting a compound according to formula XIV:

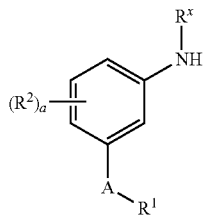

or a salt thereof, with a compound according to Formula XVIII:

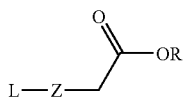

wherein, Z is as herein defined for compounds of Formula I, R is —(C$_1$-C$_6$)alkyl, and L is a leaving group selected from halogen, preferably chloro;

(b) isolating a compound according to Formula XIII, wherein R is —(C$_1$-C$_6$)alkyl;

(c) hydrolyzing the compound according to Formula XIII, isolated in step (b), to the corresponding carboxylic acid, preferably in an aqueous base such as, for example aqueous lithium hydroxide, aqueous sodium hydroxide or aqueous potassium hydroxide;

(d) isolating from the reaction products of step (c), a compound according to Formula XIII, or a salt thereof, wherein R is —H;

(e) optionally, if R$^1$ is a protecting group comprising —Si[(C$_1$-C$_6$)alkyl]$_3$, or —CH$_2$CH$_2$Si[(C$_1$-C$_6$)alkyl]$_3$, removing said protecting group, preferably with a reagent selected from the group consisting of tetrabutylammoniumfluoride (TBAF) and triethylamine trihydrofluoride;

(f) isolating from the reaction products of step (e) a compound according to Formula XIIIA, or a salt thereof:

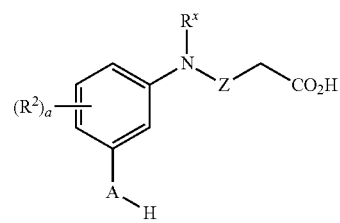

(g) coupling either the compound according to Formula XIII isolated in step (b), or the compound according to Formula XIIIA formed in step (f), with an aromatic aldehyde of formula XVI:

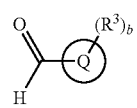

preferably, in an acidic solvent or acidic solvent mixture, more preferably, glacial acetic acid at elevated temperature; and (h) isolating a compound according to Formula IE, wherein X is —NR$^x$—Z—, or a salt of such a compound.

D. Preparation of Compounds of Formula IZ or IE, Wherein X is —NR$^x$—Z.

According to another embodiment of the invention, a process for preparing a compound according to Formula IZ or Formula IE, or a salt thereof, is provided comprising:

(1) derivatizing a carboxylic acid of Formula XVIII, or a salt thereof:

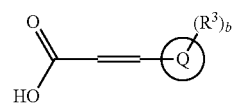

wherein, Q, R$^3$ and b are as defined for Formula I and the exocyclic carbon-carbon double bond may be in either the (E)- or (Z)-configuration; to form a carboxylic acid derivative of Formula XVIIIA:

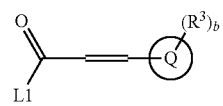

wherein L1 is a leaving group selected from halogen, preferably chloro and —OC(=O) (C$_1$-C$_6$)alkyl;

(2) coupling the carboxylic acid derivative of Formula XVIIIA to a compound according to Formula XIV:

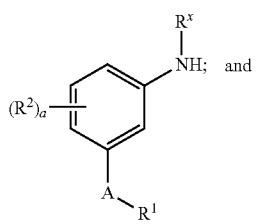

XIV (3) isolating from the reaction products, either:
(a) a compound according to Formula IE, if the exocyclic carbon-carbon double bond of Formula XVIII is in the (E)-configuration; or
(b) a compound according to Formula IZ, if the exocyclic carbon-carbon double bond of Formula XVIII is in the (Z)-configuration; or a salt of such a compound according to Formula IE or IZ.

IX. Conjugates of Compounds of the Invention

According to another embodiment of the invention, a conjugate of the Formula I-L-Ab is provided, wherein I is a compound according to Formula I; Ab is an antibody; and -L- is a single bond or a linking group covalently linking said compound according to Formula I to said antibody.

According to sub-embodiments of conjugates of the Formula I-L-Ab, the compound according to Formula I, forming the conjugate is a compound according to Formula IIA, IIB, IIIA, IIIB, IVA, IVB, VA, VB, VIA and VIB.

In a preferred sub-embodiment of the aforesaid conjugates, the antibody (Ab) is a monoclonal antibody or a monospecific polyclonal antibody.

In more preferred sub-embodiments of the aforesaid conjugates, the antibody (Ab) is a tumor-specific antibody.

X. Pharmaceutical Compositions

According to another embodiment of the invention, pharmaceutical compositions are provided, comprising a pharmaceutically acceptable carrier and a compound according to Formula I:

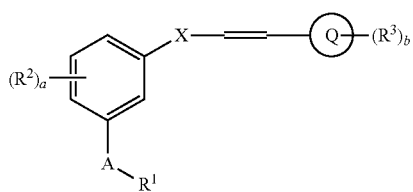

I wherein R$^1$, R$^2$, R$^3$, A, X, Q, a and b are as described above for Formula I; or a salt of such a compound.

Pharmaceutical compositions are also provided comprising a pharmaceutically acceptable carrier and at least one conjugate according to Formula I-L-Ab, wherein I, L and Ab are as defined herein.

XI. Methods of Treatment

According to another embodiment of the invention, there is provided a method of treating an individual for a proliferative disorder, particularly cancer, comprising administering to the individual an effective amount of at least one compound according to Formula I or at least one conjugate of Formula I-L-Ab, alone or in combination with a pharmaceutically acceptable carrier.

According to a further embodiment of the invention, a method of inducing apoptosis of tumor cells in an individual afflicted with cancer is provided, comprising administering to the individual an effective amount of at least one compound according to Formula I, or at least one conjugate of Formula I-L-Ab, either alone or in combination with a pharmaceutically acceptable carrier.

According to another embodiment of the invention, a method of inhibiting the growth of tumor cells in an individual afflicted with cancer is provided, comprising administering to the individual an effective amount of at least one compound according to Formula I, or at least one conjugate of the Formula I-L-Ab, alone or in combination with a pharmaceutically acceptable carrier.

According to another embodiment of the invention, a method of reducing or eliminating the effects of ionizing radiation on normal calls in an individual who has incurred or is at risk for incurring exposure to ionizing radiation, is provided. This method comprises administering to the individual either prior to, or after the exposure to ionizing radiation, at least one compound according to Formula I, alone or in combination with a pharmaceutically acceptable carrier.

According to another embodiment of the invention, there is provided a method of safely increasing the dosage of therapeutic ionizing radiation used in the treatment of cancer or another proliferative disorder, comprising administering an effective amount of at least one radioprotective compound according to Formula I, alone or in combination with a pharmaceutically acceptable carrier. Without wishing to be bound by any theory, the radioprotective compound is believed to induce a temporary radioresistant phenotype in the normal tissue of the individual.

According to another embodiment of the invention, there is provided a method for treating an individual who has incurred, or is at risk for incurring remediable radiation damage from exposure to ionizing radiation. This method comprises administering an effective amount of at least one radioprotective compound according to Formula I, alone or in combination with a pharmaceutically acceptable carrier, either prior to, or after the individual incurs remediable radiation damage from exposure to ionizing radiation.

According to another embodiment of the invention, there is provided a method of treating an individual for a proliferative disorder, particularly cancer, comprising:
(1) administering to the individual an effective amount of at least one radioprotective compound according to Formula I, or at least one conjugate of Formula I-L-Ab; and
(2) administering an effective amount of therapeutic ionizing radiation.

According to another embodiment of the invention, there is provided a method of reducing the number of malignant cells in the bone marrow of an individual, comprising:
(1) removing a portion of the individual's bone marrow;
(2) administering an effective amount of at least one radioprotective compound according to Formula I, to the removed bone marrow; and
(3) irradiating the removed bone marrow with an effective amount of ionizing radiation.

According to one sub-embodiment, there is provided the above method of reducing the number of malignant cells in the bone marrow of an individual, further comprising replacing the removed bone marrow with the irradiated bone marrow.

According to another embodiment of the invention, there is provided a method for protecting an individual from cytotoxic side effects of the administration of a cytotoxic agent, particularly a mitotic phase cell cycle inhibitor or a topoisomerase inhibitor, comprising administering to the individual, in advance of the administration of the cytotoxic agent, an effective amount of at least one cytoprotective compound according to Formula I; wherein the mitotic phase cell cycle inhibitor or topoisomerase inhibitor is not a compound according to Formula I.

According to another sub-embodiment thereof, there is provided the above described method wherein the cytotoxic agent is a topoisomerase inhibitor.

Topoisomerase inhibitors may be inhibitors of topoisomerase I, topoisomerase II or both. Topoisomerase I inhibitors include, but are not limited to, adriamycin and etoposide. Topoisomerase II inhibitors include, but are not limited to, camptothecin, irinotecan, topotecan and mitoxanthrone.

According to another embodiment of the invention, there is provided a method of treating an individual for a proliferative disorder, particularly cancer, comprising:

(1) administering to the individual an effective amount of at least one cytoprotective compound according to Formula I, or the at least one conjugate of Formula I-L-Ab; and (2) administering an effective amount of at least one mitotic cell phase inhibitor or topoisomerase inhibitor after administration of the at least one cytoprotective compound according to Formula I, or at least one conjugate of Formula I-L-Ab.

According to other embodiments of the invention, there is provided the use of at least one compound according to Formula I, or at least one conjugate according to Formula I-L-Ab, either alone or as a part of a pharmaceutical composition, for preparation of a medicament for:

(a) treating a proliferative disorder in an individual afflicted with a proliferative disorder;

(b) inhibiting the growth of tumor cells in an individual afflicted with cancer;

(c) inducing apoptosis of tumor cells in an individual afflicted with cancer;

(d) treating an individual who has incurred, or is at risk for incurring remediable radiation damage from exposure to ionizing radiation;

(e) reducing or eliminating the effects of ionizing radiation on normal calls in an individual who has incurred or is at risk for incurring exposure to ionizing radiation;

(f) safely increasing the dosage of therapeutic ionizing radiation used in the treatment of cancer or another proliferative disorder; or (g) protecting an individual from cytotoxic side effects of the administration of a cytotoxic agent.

BRIEF DESCRIPTION OF THE FIGURE

FIG. 1 shows the dose response curve for the compound (E)-5-((2,4,6-trimethoxystyrylsulfonyl)methyl)-2-methoxyphenol (Example 1) in six different cancer cell lines.

DETAILED DESCRIPTION OF THE INVENTION

I. Treatment of Proliferative Disorders

According to the present invention, compounds of Formula I and salts thereof, and conjugated according to Formula I-L-Ab, are believed to selectively inhibit proliferation of cancer cells, and kill various tumor cell types without killing (or with reduced killing of) normal cells. It is believed that cells are killed at concentrations where normal cells may be temporarily growth-arrested but not killed.

A. Treatment of Cancer

The compounds and conjugates of the invention may be administered to individuals (mammals, including animals and humans) afflicted with cancer.

The compounds and conjugates of the invention are believed to inhibit the proliferation of tumor cells and, for some compounds or conjugates, to induce cell death. Cell death is believed to result from the induction of apoptosis. The compounds and conjugates are believed effective against a broad range of tumor types, including but not limited to the following: ovarian cancer; cervical cancer; breast cancer; prostate cancer; testicular cancer, lung cancer, renal cancer; colorectal cancer; skin cancer; brain cancer; leukemia, including acute myeloid leukemia, chronic myeloid leukemia, acute lymphoid leukemia, and chronic lymphoid leukemia.

More particularly, cancers that may be treated by the compounds, conjugates, compositions and methods of the invention include, but are not limited to the following:

cardiac cancers, including, for example sarcoma, e.g., angiosarcoma, fibrosarcoma, rhabdomyosarcoma, and liposarcoma; myxoma; rhabdomyoma; fibroma; lipoma and teratoma;

lung cancers, including, for example, bronchogenic carcinoma, e.g., squamous cell, undifferentiated small cell, undifferentiated large cell, and adenocarcinoma; alveolar and bronchiolar carcinoma; bronchial adenoma; sarcoma; lymphoma; chondromatous hamartoma; and mesothelioma;

gastrointestinal cancer, including, for example, cancers of the esophagus, e.g., squamous cell carcinoma, adenocarcinoma, leiomyosarcoma, and lymphoma; cancers of the stomach, e.g., carcinoma, lymphoma, and leiomyosarcoma; cancers of the pancreas, e.g., ductal adenocarcinoma, insulinoma, glucagonoma, gastrinoma, carcinoid tumors, and vipoma; cancers of the small bowel, e.g., adenocarcinoma, lymphoma, carcinoid tumors, Karposi's sarcoma, leiomyoma, hemangioma, lipoma, neurofibroma, and fibroma; cancers of the large bowel, e.g., adenocarcinoma, tubular adenoma, villous adenoma, hamartoma, and leiomyoma;

genitourinary tract cancers, including, for example, cancers of the kidney, e.g., adenocarcinoma, Wilm's tumor (nephroblastoma), lymphoma, and leukemia; cancers of the bladder and urethra, e.g., squamous cell carcinoma, transitional cell carcinoma, and adenocarcinoma; cancers of the prostate, e.g., adenocarcinoma, and sarcoma; cancer of the testis, e.g., seminoma, teratoma, embryonal carcinoma, teratocarcinoma, choriocarcinoma, sarcoma, interstitial cell carcinoma, fibroma, fibroadenoma, adenomatoid tumors, and lipoma;

liver cancers including, for example, hepatoma, e.g., hepatocellular carcinoma; cholangiocarcinoma; hepatoblastoma; angiosarcoma; hepatocellular adenoma; and hemangioma;

bone cancer including, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors;

nervous system cancers including, for example, cancers of the skull, e.g., osteoma, hemangioma, granuloma, xanthoma, and osteitis deformans; cancers of the meninges, e.g., meningioma, meningiosarcoma, and gliomatosis; cancers of the brain, e.g., astrocytoma, medulloblastoma, glioma, ependymoma, germinoma (pinealoma), glioblastoma multiform, oligodendroglioma, schwannoma, retinoblastoma, and congenital tumors; and cancers of the spinal cord, e.g., neurofibroma, meningioma, glioma, and sarcoma;

gynecological cancers including, for example, cancers of the uterus, e.g., endometrial carcinoma; cancers of the cervix, e.g., cervical carcinoma, and pre-tumor cervical dysplasia; cancers of the ovaries, e.g., ovarian carcinoma, including serous cystadenocarcinoma, mucinous cystadenocarcinoma, unclassified carcinoma, granulosa-thecal cell tumors, Sertoli-Leydig cell tumors, dysgerminoma, and malignant teratoma; cancers of the vulva, e.g., squamous cell carcinoma, intraepithelial carcinoma, adenocarcinoma, fibrosarcoma, and melanoma; cancers of the vagina, e.g., clear cell carcinoma, squamous cell carcinoma, botryoid sarcoma, and embryonal rhabdomyosarcoma; and cancers of the fallopian tubes, e.g., carcinoma;

hematologic cancers including, for example, cancers of the blood, e.g., acute myeloid leukemia, chronic myeloid leukemia, acute lymphoblastic leukemia, chronic lymphocytic leukemia, myeloproliferative diseases, multiple myeloma, and myelodysplastic syndrome, Hodgkin's lymphoma, non-Hodgkin's lymphoma (malignant lymphoma) and Waldenström's macroglobulinemia;

skin cancers including, for example, malignant melanoma, basal cell carcinoma, squamous cell carcinoma, Karposi's sarcoma, moles dysplastic nevi, lipoma, angioma, dermatofibroma, keloids, psoriasis; and adrenal gland cancers including, for example, neuroblastoma. Cancers may be solid tumors that may or may not be metastatic.

Cancers may also occur, as in leukemia, as a diffuse tissue. Thus, the term "tumor cell" as provided herein, includes a cell afflicted by any one of the above identified disorders.

According to one embodiment of the methods of treatment according to the invention, the treated proliferative disorder is hepatoma. According to another embodiment of the methods of treatment according to the invention, the treated proliferative disorder is breast cancer.

B. Treatment of Non-Cancer Proliferative Disorders

The compounds and conjugates of the invention are also believed useful in the treatment of non-cancer proliferative disorders, that is, proliferative disorders which are characterized by benign indications. Such disorders may also be known as "cytoproliferative" or "hyperproliferative" in that cells are made by the body at an atypically elevated rate. Non-cancer proliferative disorders believed treatable by compounds and conjugates of the invention include, for example: hemangiomatosis in newborn, secondary progressive multiple sclerosis, atherosclerosis, chronic progressive myelodegenerative disease, neurofibromatosis, ganglioneuromatosis, keloid formation, Paget's disease of the bone, fibrocystic disease of the breast, uterine fibroids, Peyronie's fibrosis, Dupuytren's fibrosis, restenosis, benign proliferative breast disease, benign prostatic hyperplasia, X-linked lymphoproliferative disorder (Duncan disease), post-transplantation lymphoproliferative disorder (PTLD), macular degeneration, and retinopathies, such as diabetic retinopathies and proliferative vitreoretinopathy (PVR)

Other non-cancer proliferative disorders believed treatable by compounds and conjugates of the invention include the presence of pre-cancerous lymphoproliferative cells associated with an elevated risk of progression to a cancerous disorder. Many non-cancerous lymphoproliferative disorders are associated with latent viral infections such as Epstein-Barr virus (EBV) and Hepatitis C. These disorders often begin as a benign pathology and progress into lymphoid neoplasia as a function of time.

Treatment of tumor cells with the compounds and conjugates of the invention is believed to lead to inhibition of cell proliferation and induction of apoptotic cell death.

II. Radioprotective Treatment

The compounds of Formula I are also believed to protect normal cells and tissues from the effects of acute and chronic exposure to ionizing radiation.

Individuals may be exposed to ionizing radiation when undergoing therapeutic irradiation for the treatment of proliferative disorders. The compounds are believed effective in protecting normal cells during therapeutic irradiation of abnormal tissues. The compounds are also believed useful in protecting normal cells during radiation treatment for leukemia, especially in the purging of malignant cells from autologous bone marrow grafts with ionizing radiation.

According to the invention, therapeutic ionizing radiation may be administered to an individual on any schedule and in any dose consistent with the prescribed course of treatment, as long as the radioprotectant compound according to the invention is administered prior to the radiation. The course of treatment differs from individual to individual, and those of ordinary skill in the art can readily determine the appropriate dose and schedule of therapeutic radiation in a given clinical situation.

III. Chemoprotective Treatment

In addition, the compounds of Formula I are believed to protect normal cells and tissues from the effects of exposure to mitotic phase cell cycle inhibitors and topoisomerase inhibitors.

Mitotic cell phase inhibitors include, but are not limited to, vinca alkaloids, e.g., vincristine and vinblastine, particularly vincristine; estramustine; taxanes, e.g., paclitaxel and analogs of paclitaxel, particularly paclitaxel; naturally occurring macrolides, e.g., rhizoxin, maytansine, ansamitocin P-3, phomopsin A, dolastatin 10 and halichrondin B; colchicine and derivatives of colchicine.

Paclitaxel is an anti-mitotic drug which has been used as an initial treatment for ovarian, breast and lung cancer, with moderate success. Vincrisitin is a well-established anti-mitotic drug widely used for the treatment of breast cancer, Hodgkin's lymphoma and childhood cancers.

Topoisomerase inhibitors include compounds that inhibit topoisomerase I, compounds that inhibit topoisomerase II, and compounds that inhibit both topoisomerase I and II.

Inhibitors of topoisomerase I include, for example, adriamycin, etoposide, β-lapachone (Calbiochem No. 428022), AG-555 (Calbiochem No. 112270), 10-hydroxycamptothecin (Calbiochem No. 390238), AG-1387 (Calbiochem No. 658520), rebeccamycin (Calbiochem No. 553700), nogalamycin (Calbiochem No. 488200), and topotecan (Calbiochem No. 614800).

Inhibitors of topoisomerase II include, for example, camptothecin, irinotecan and topotecan, amsacrine (Calbiochem No. 171350), aurintricarboxylic acid (Calbiochem No.

189400), bruneomycin (Calbiochem No. 571120), ellipticine (Calbiochem No. 324688), epirubicin (Calbiochem No. 324905), etoposide (Calbiochem No. 341205), genistein (Calbiochem No. 345834), and merbarone (Calbiochem No. 445800).

Inhibitors of both topoisomerase I and II include, for example, aclarubicin (Calbiochem No. 112270), congocidine (Calbiochem No. 480676), daunomycin (Calbiochem No. 251800), ellagic acid (Calbiochem No. 324683), and suramin (Calbiochem No. 574625).

The compounds of the present invention are believed to not only protect normal cells, but are also to be operationally cytotoxic in tumor cells. In normal cells, the cytoprotective compounds of the invention are believed to induce a reversible resting state rendering the normal cells relatively refractory to the cytotoxic effect of mitotic phase cell cycle inhibitors and topoisomerase inhibitors.

IV. Compounds of Formula I

A. Ring Substitution

The pattern of substitution for ring hydrogens of the phenyl ring and aromatic ring Q of Formula I may comprise any pattern of substitution as long as the -A-$R^1$ functionality is positioned at the 3-position of the phenyl ring, relative to —X—. For example, when ring Q is phenyl, tri-substitution on Q may comprise substitution at positions 2, 3 and 4, positions 2, 4 and 5, positions 3, 4 and 5, positions 2, 5 an 6 or positions 2, 4 and 6. Di-substitution of a phenyl Q may comprise substitution, for example, at the 2 and 3 positions, the 2 and 4 positions, the 2 and 5 positions, the 2 and 6, positions, the 3 and 4 positions, the 3 and 5 positions, or the 3 and 6 positions.

The pattern of substitution on a five-membered heteroaryl Q ring must also account for the number of heteroatoms contained in the heteroaromatic ring and point of attachment of the heteroaryl ring. Substitution on a five membered heteroaromatic ring containing one heteroatom, wherein the heteroaryl ring is bonded via its 2-position serves to exemplify the variety of substitution patterns. Substitution on the aforesaid five-membered heteroaryl Q ring may be, for example, at the 3, 4 or 5 position for mono-substitution; and at the 3 and 4, the 3 and 5, or the 4 and 5 positions for di-substitution.

When b is 1 in Formula I, $R^3$ is preferably located at the ortho- or para-position. When b is 2, $R^3$ substituents are preferably located at ortho- and para-positions, or at both ortho-positions. When b is 3, $R^3$ substituents are preferably located at the para- and at least one ortho-position, more preferably, at the para- and at both ortho-positions.

When a is 1 in Formula I, $R^2$ is preferably positioned para- to —X or para- to -A-$R^1$; more preferably, para- to —X. When a is 2 or 3, $R^2$ substituents are preferably positioned para- to —X and para- to -A-$R^1$.

The terms "para-", "meta-" and "ortho-", substitution positions on a ring are also denoted by a numbering system. However numbering systems are often not consistent between different ring systems. In six-membered aromatic systems, the spatial arrangements are specified as described above by the common nomenclature "para-" for 1,4-substitution, "meta-" for 1,3-substitution and "ortho-" for 1,2-substitution as shown below in Scheme 3.

Scheme 3

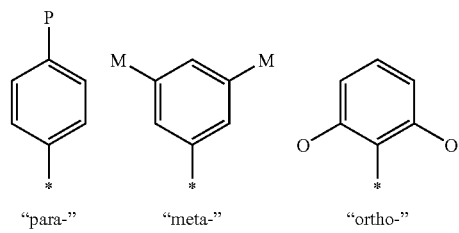

"para-"   "meta-"   "ortho-"

Since aromatic rings are essentially planar, ortho-, meta-, and para-designations essentially define geometric positions on a six-membered ring that correlate geometrically to planar angles. Thus, an ortho-substituent forms a planar angle of 60° with a reference substituent to which it is referred to as being ortho-. Likewise, a meta-substituent defines a 120° planar angle and a para-substituent defines a 180° angle.

Designation of substituent patterns as ortho-, meta-, and para nomenclature as 60, 120 and 180 angles is descriptive for six-membered monocycles. There is no substituent on a five-membered aromatic ring or a bicyclic ring which forms a 60, 120 or 180° angle. However, definition of a planar angle or a range of planar angles between two substituents is a convention which readily communicates a particular substitution pattern that is independent of the nature of the particular ring involved. A para-substituent in a six-membered aromatic ring is closely approximated in other planar mono- or bicyclic rings by any substituent which, with the reference substituent, forms a planar angle of between about 144° and about 180°. Likewise, a meta-substituent in a six-membered aromatic ring is approximated in other planar mono- or bicyclic rings by any substituent which, with the reference substituent, forms a planar angle of between about 90° and about 144°. Several examples of substituent patterns which could be communicated in this way are depicted in Scheme 4.

Scheme 4

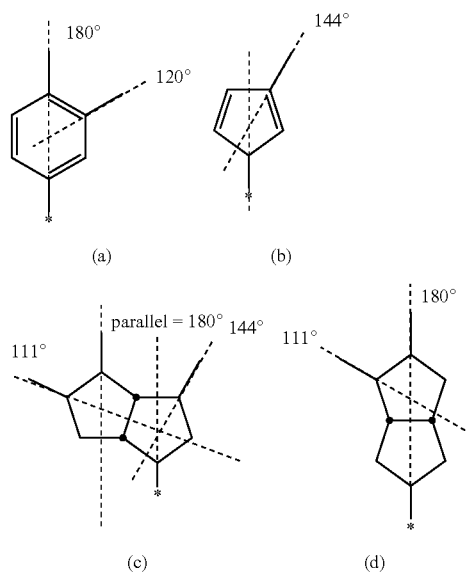

(a)   (b)

(c)   (d)

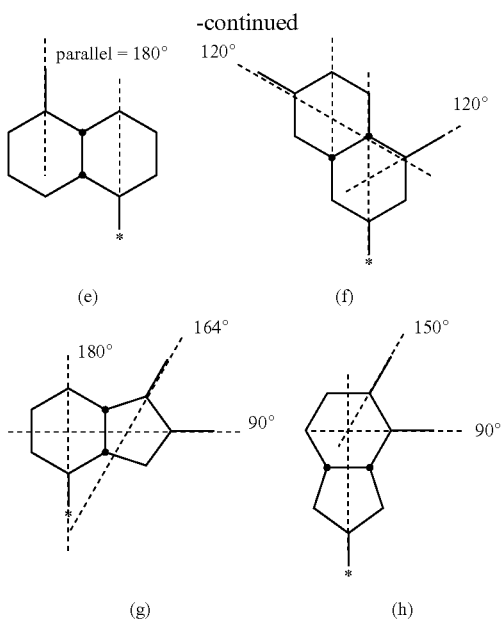

(e)  (f)  (g)  (h)

In some instances, a true angle is not formed between a substituent and a reference substituent. One example of this is a naphthalene system substituted at the 1- and 5-positions as shown in the (e) structure above. In the (e) structure there is no geometric intersection between the lines defined by the 1- and 5-position bonds. However, it is reasonable to regard these "parallel" bonds as defining a 180° angle and thus approximating the para-arrangement of a six-membered planar ring.

Thus, for the above described preferences for positions of $R^2$ and $R^3$ substituents, the preference of para-substitution corresponds to substituents that form a planar angle of between about 144° and about 180°, or the bonds are parallel as in structure (e) of Scheme 4. Likewise, preferences of meta-substitution correspond to substituents that form a planar angle of between about 90° and about 144°. Preferences of ortho-substitution always refer to a substituent at a position adjacent to the position used as a reference position.

B. E-/Z-Isomerism in Compounds of the Invention

The compounds of Formula I are characterized by isomerism resulting from the presence of an exocyclic carbon-carbon double bond. This isomerism is commonly referred to as cis-trans isomerism, but the more comprehensive naming convention employs E- and Z-designations. The compounds are named according to the Cahn-Ingold-Prelog system, the IUPAC 1974 Recommendations, Section E: Stereochemistry, in *Nomenclature of Organic Chemistry*, John Wiley & Sons, Inc., New York, N.Y., 4$^{th}$ ed., 1992, p. 127-138, the entire contents of which is incorporated herein by reference. Using this system of nomenclature, the four groups about a double bond are prioritized according to a series of rules. Then, that isomer with the two higher ranking groups on the same side of the double bond is designated Z (for the German word "zusammen", meaning together). The other isomer, in which the two higher-ranking groups are on opposite sides of the double bond, is designated E (for the German word "entgegen", which means "opposite"). Thus, if the four groups on a carbon-carbon double bond are ranked, A being the lowest rank and D being highest, A>B>C>D, the isomers would be named as in Scheme 5.

Scheme 5

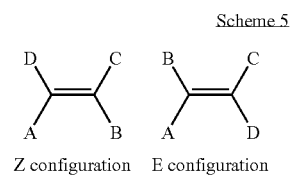

Z configuration    E configuration

Unless otherwise indicated, both configurations, as depicted below in Scheme 6, and mixtures thereof, are included in the scope of compounds of Formula I.

Scheme 6

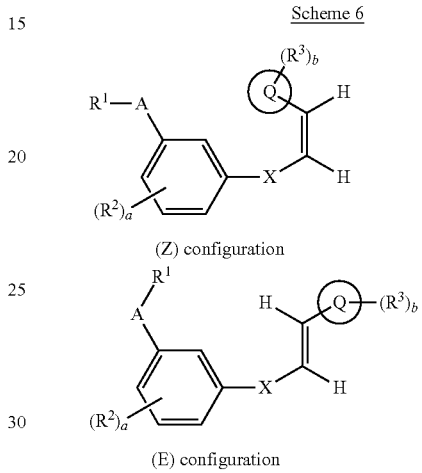

(Z) configuration (E) configuration

C. Optical Isomerism

The present invention is also directed to isolated optical isomers of compounds according to Formula I. The isomers resulting from the presence of a chiral center comprise a pair of non-superimposable isomers that are called "enantiomers." Single enantiomers of a pure compound are optically active, i.e., they are capable of rotating the plane of plane polarized light. Single enantiomers are designated according to the Cahn-Ingold-Prelog system. See March, Advanced Organic Chemistry, 4$^{th}$ Ed., (1992), p. 109. Once the priority ranking of the four groups is determined, the molecule is oriented so that the lowest ranking group is pointed away from the viewer. Then, if the descending rank order of the other groups proceeds clockwise, the molecule is designated (R) and if the descending rank of the other groups proceeds counterclockwise, the molecule is designated (S). In the example in Scheme 7, the Cahn-Ingold-Prelog ranking is A>B>C>D. The lowest ranking atom, D is oriented away from the viewer.

Scheme 7

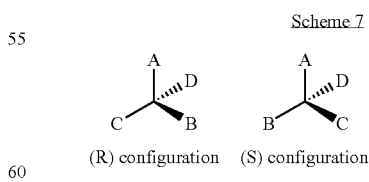

(R) configuration    (S) configuration

Sulfoxides of Formula I (e.g. sulfoxides of Formulae IIB, IIIB, IVB, VB and VIB) have at least one chiral center which is the sulfoxide sulfur atom. In addition, for compounds of Formula I, wherein X is —C*H(R$^x$)SO$_2$— or —C*H(R$^x$)SO—, and R$^x$ is other than hydrogen, the carbon atom (C*) to which R$^x$ is attached is a chiral center.

For the sulfoxide chiral center present in compounds of the present invention (Compounds of Formula I, wherein Y is —S(=O)—), the lowest priority (an empty orbital) and the highest priority (the sulfoxide oxygen) atoms about the chiral sulfur are fixed. Thus, the absolute configuration of compounds of the invention depends on the priority ranking of the two carbon atoms bonded to the sulfoxide group as shown in Scheme 8.

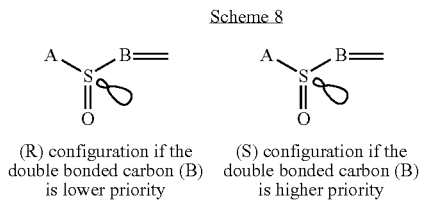

Scheme 8

(R) configuration if the double bonded carbon (B) is lower priority (S) configuration if the double bonded carbon (B) is higher priority Certain compounds of Formula I may have more than one chiral center, e.g., when X is —C*H($R^x$)$SO_2$— or —C*H($R^x$)SO—, and $R^x$ is other than —H. If a compound has more than one chiral center, diastereomeric isomerism results, as exemplified in Scheme 9 by the truncated structures of Formula I.

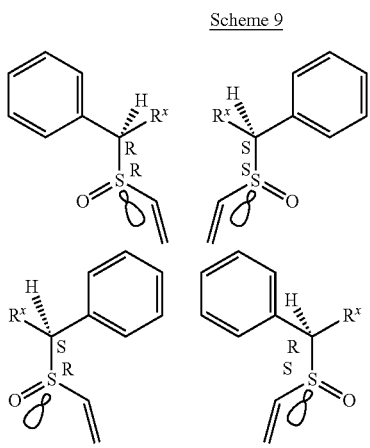

Scheme 9

The present invention is meant to encompass diastereomers as well as their racemic and resolved, diastereomerically and enantiomerically pure forms and salts thereof. Diastereomeric pairs may be resolved by known separation techniques including normal and reverse phase chromatography, and crystallization.

Isolated optical isomers may be purified from racemic mixtures by well-known chiral separation techniques. According to one such method, a racemic mixture of a compound having the structure of Formula I, or a chiral intermediate thereof, is separated into 99% wt. % pure optical isomers by HPLC using a suitable chiral column, such as a member of the series of DAICEL CHIRALPAK family of columns (Daicel Chemical Industries, Ltd., Tokyo, Japan). The column is operated according to the manufacturer's instructions.

V. Preparation of Compounds of the Invention

Compounds of Formula I may be prepared via synthetic organic chemistry methods within the capability of a chemist of ordinary skill. Compounds of Formula I wherein the exocyclic carbon-carbon double bond is (E)- and wherein the exocyclic carbon-carbon double bond is (Z)- are preferably prepared via procedures that are selective for the preparation of (E)- or (Z)-olefins respectively.

A. Preparation of α,β-Unsaturated Sulfoxides and Sulfones of Formula I (i) Preparation of Compounds of Formula IE One preferred preparation of (E)-compounds of Formula I wherein X is —C*H($R^x$)SO— or —C*H($R^x$)$SO_2$—, is by a Knoevenagel condensation of Q-aldehydes 8 with substituted phenyl-(CHR$^x$)$_n$-sulfinyl acetic acids 7b, or substituted phenyl-(CHR$^x$)$_n$-sulfonyl acetic acids 7a, respectively, according to the Scheme 10 below, wherein $R^1$, $R^2$, $R^3$, $R^x$, A, Q, a, b, n and * are as defined herein for Formula I.

Scheme 10

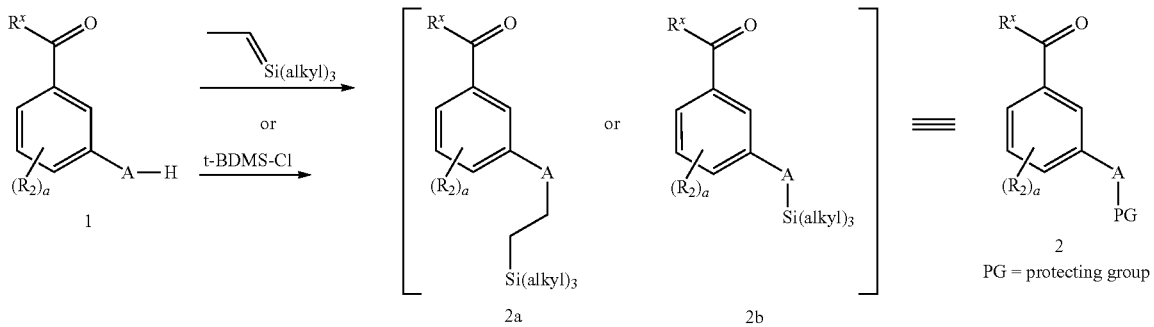

PG = protecting group

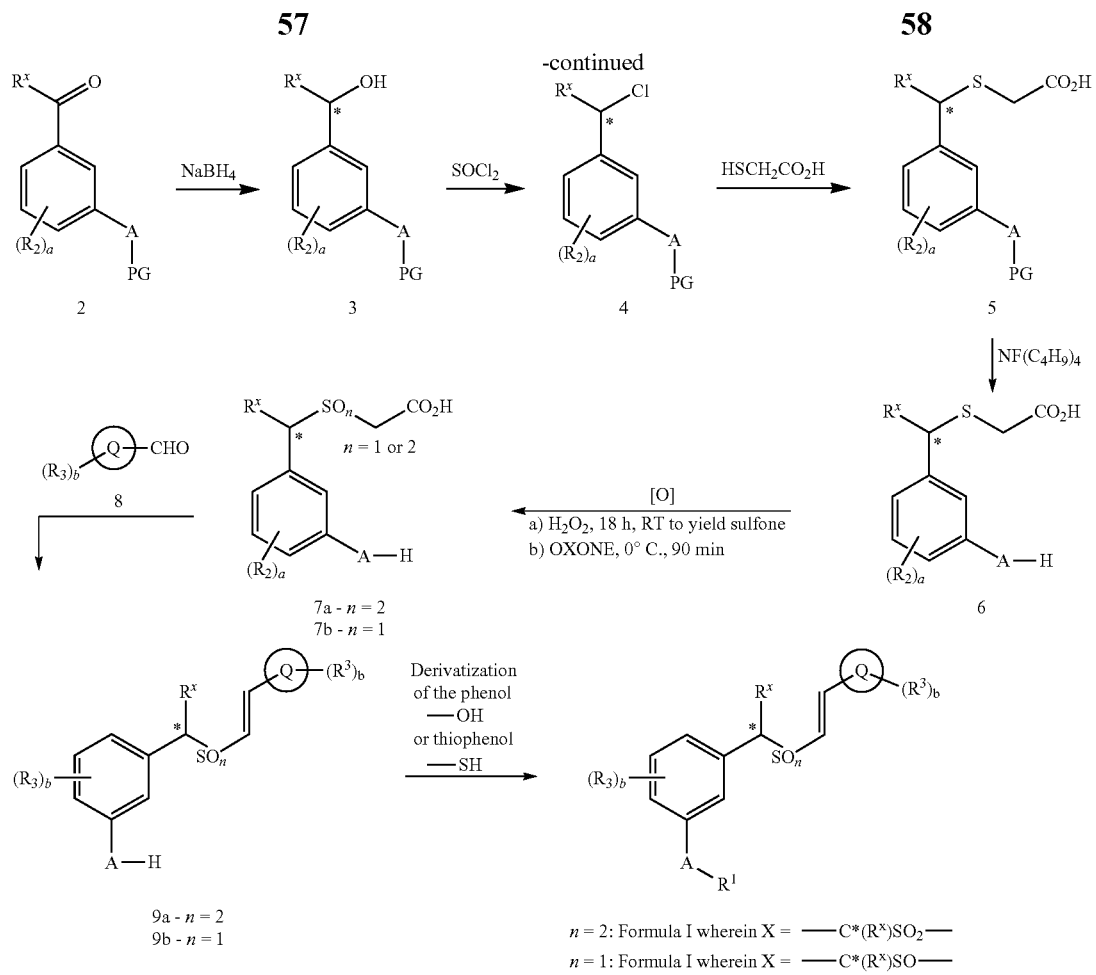

The synthesis route illustrated in Scheme 10 serves to produce compounds of Formulae 9a and 9b, which are themselves compounds of Formula I. In addition, compounds of Formulae 9a and 9b serve as advanced intermediates which may be further derivatized to provide additional novel compounds of Formula I via derivatization of the 3-hydroxy or 3-mercapto moiety.

According to Scheme 10, a starting phenol or thiophenol 1, is first derivatized to protect the phenol or thiophenol moiety. Phenol and thiophenol compounds, 1 are reacted with a trialkylsilyl halide, preferably tert-butyldimethylsilyl chloride (t-BDMS-Cl), or with a vinyltrialkylsilane, preferably vinyl tert-butyldimethylsilane or vinyl trimethylsilane, to produce the corresponding trialkylsilylethyl protected phenol or thiophenol, 2.

The protected compound, 2, is treated with a reducing agent capable of reducing a ketone or aldehyde to the corresponding alcohol. Suitable reducing agents include hydride reducing agents, e.g., $NaBH_4$ and $NaBH_3CN$. Preferably the reaction is performed in a solvent, e.g., tetrahydrofuran (THF). The reduction provides the benzyl alcohol derivative, 3.

The benzyl alcohol, 3, is reacted with a halogenating agent, e.g., thionyl chloride, to provide the benzyl halide derivative, 4.

According to Scheme 10, benzylmercaptoacetic acid compound 5 is formed by the reaction of mercaptoacetic acid (or a salt thereof) with 4, wherein $R^2$, $R^x$, and a are as defined herein for Formula I and L is a leaving group. Suitable mercaptoacetic acid salts include alkali metal salts such as sodium and potassium salts. Suitable leaving groups for 4 include, for example, halogen, tosyl, nosyl, trifyl, or mesyl. The reaction is preferably carried out in a polar solvent, more preferably a ($C_1$-$C_4$) alkyl alcohol, e.g., methanol. The reaction is preferably carried out at room temperature or higher, more preferably greater than 50° C., most preferably at the reflux temperature of the solvent.

The benzylmercaptoacetic acid compound 5 is then deprotected to remove the thiophenol or phenol protecting group, PG, to provide the 3-hydroxy or 3-mercapto benzylmercaptoacetic acid, 6. Suitable deprotection reagents include TBAF and triethylamine trihydrofluoride.

The deprotected compound 6, is then oxidized with a suitable oxidizing agent to give a corresponding sulfinyl acetic acid compound 7b, or sulfonyl acetic acid compound, 7a. A suitable oxidizing agent is any oxidant capable of selectively oxidizing a sulfide to a sulfoxide (e.g., 7a), or capable of selectively oxidizing a sulfide to a sulfone (e.g., 7b). Examples include 3-chloroperbenzoic acid (MCPBA) (Aldrich 27,303-1) and potassium peroxymonosulfate (Aldrich 22,803-6). The oxidation to form the sulfoxide, 7b is preferably performed at low temperature, preferably from −40° C. to 0° C. The oxidation to form the sulfone, 7a is preferably performed at room temperature or higher, more preferably from 30° C. to 50° C. The reaction is preferably carried out in a suitable solvent. Suitable solvents are preferably nonpolar organic solvents, more preferably halogenated solvents, e.g., dichloromethane (DCM).

Condensation of sulfoxide 7b or sulfone 7a with the Q-aldehydes 8 via a Knoevenagel reaction in the presence of benzylamine and glacial acetic acid yields the desired (E)-α,β-unsaturated sulfoxide 9b or the (E)-α,β-unsaturated sulfone, 9a, respectively.

Compounds 9b or 9a, are compounds of Formula I wherein $R^1$ is —H. Compounds 9b and 9a may be subsequently derivatized to provide additional compounds of Formula I as described herein.

(ii) Preparation of Compounds of Formula IZ

One preferred preparation of compounds of Formula IZ wherein X is —C*H($R^x$)SO— or —C*H($R^x$)$SO_2$—, is by oxidation of the corresponding sulfide compound to either the sulfoxide or to the sulfone. Q-acetylenes 10 are reacted with anions of benzyl mercaptans 11 according to the Scheme 11 below, wherein $R^1$, $R^2$, $R^3$, $R^x$, A, Q, a, b, n and * are as defined herein for Formula I.

capable of oxidizing a sulfide to a sulfoxide of Formula IZ. Suitable oxidizing agents for the reaction to produce sulfoxide or sulfone compounds of Formula IZ include meta-chloroperoxybenzoic acid (MCPBA) and potassium peroxymonosulfate. The oxidation to form the sulfoxide of Formula IZ is preferably performed at low temperature, preferably from –40° C. to 0° C. The oxidation to form the sulfone of Formula IZ is preferably performed at room temperature or higher, more preferably from 30° C. to 50° C. Because the sulfoxide is an intermediate oxidation state in the oxidation of the sulfide to the sulfone, the reaction to oxidize to the sulfoxide should be monitored and terminated prior to further oxidation to the sulfone. Likewise, for the oxidation to the sulfone, the reaction should be monitored to confirm that both all of the sulfide of Formula XVI is consumed and that the intermediate sulfoxide of Formula IZ is consumed. The reaction is preferably carried out in a suitable solvent. Suitable

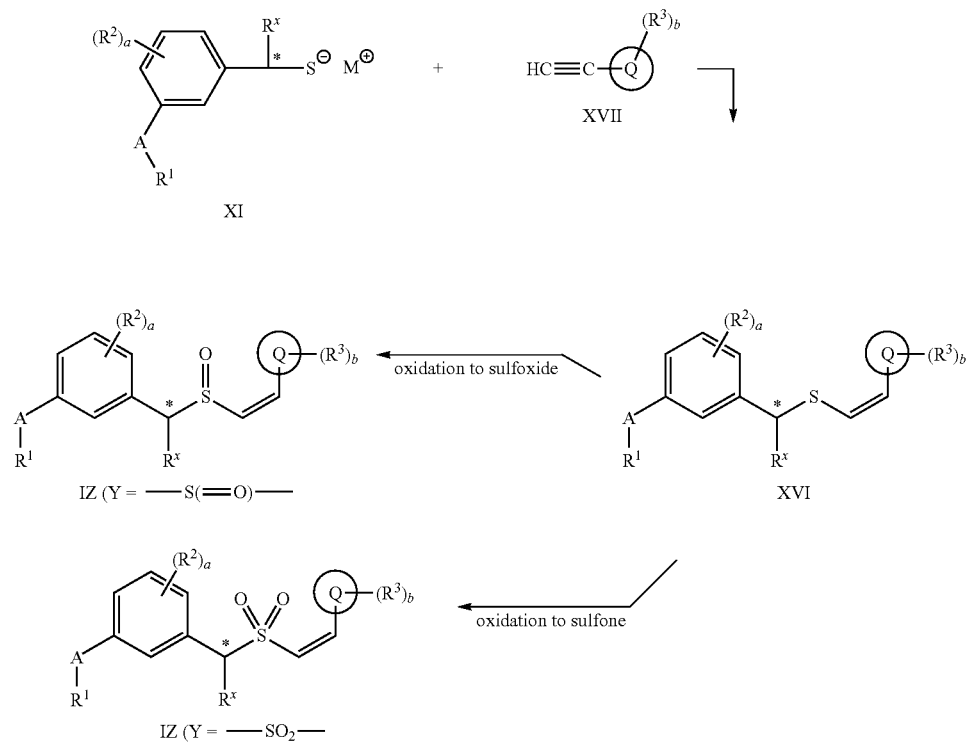

Scheme 11

According to Scheme 11, the α,β-unsaturated sulfoxides and α,β-unsaturated sulfones of Formula IZ are preferably prepared by a nucleophilic addition of an appropriate thiol salt of Formula XI to an optionally substituted aryl or heteroarylacetylene of Formula XVII. In Formula XVII, $R^1$, $R^2$, $R^3$, $R^x$, Q, a and b are defined as for compounds of Formula I, A is —S—, and $M^+$ is a counterion, preferably an alkali metal, e.g., sodium, lithium or potassium, an alkaline earth metal, e.g., calcium or magnesium, or a transition metal, e.g., zinc or copper. The synthesis depicted in Scheme 11 is analogous to the procedure described by Reddy et al., *Sulfur Letters* 13:83-90 (1991) for the production of (Z)-styryl benzylsulfoxides. The entire disclosure of Reddy et al. is incorporated herein by reference.

The sulfide intermediate XVI is then oxidized with a suitable oxidizing agent. A suitable oxidizing agent is one solvents are preferably nonpolar organic solvents, more preferably halogenated solvents, e.g., dichloromethane (DCM).

B. Preparation of α,β-Unsaturated Sulfonamides and Aryl Propenamides of Formula I (i) Preparation of Compounds of Formula IE One preferred preparation of compounds of Formula IE wherein X is —$NR^xC$(=O)— or —$NR^xSO_2$—, is by reaction of an appropriately substituted aniline compound to form either a sulfonamide or an arylpropenamide compound according to Formula XIX. The Formula XIX compound is then hydrolyzed, deprotected and reacted with an aryl or heteroaryl aldehyde of Formula XV to form a sulfonamide or an arylpropenamide compound according to Formula IE, as shown in Scheme 12.

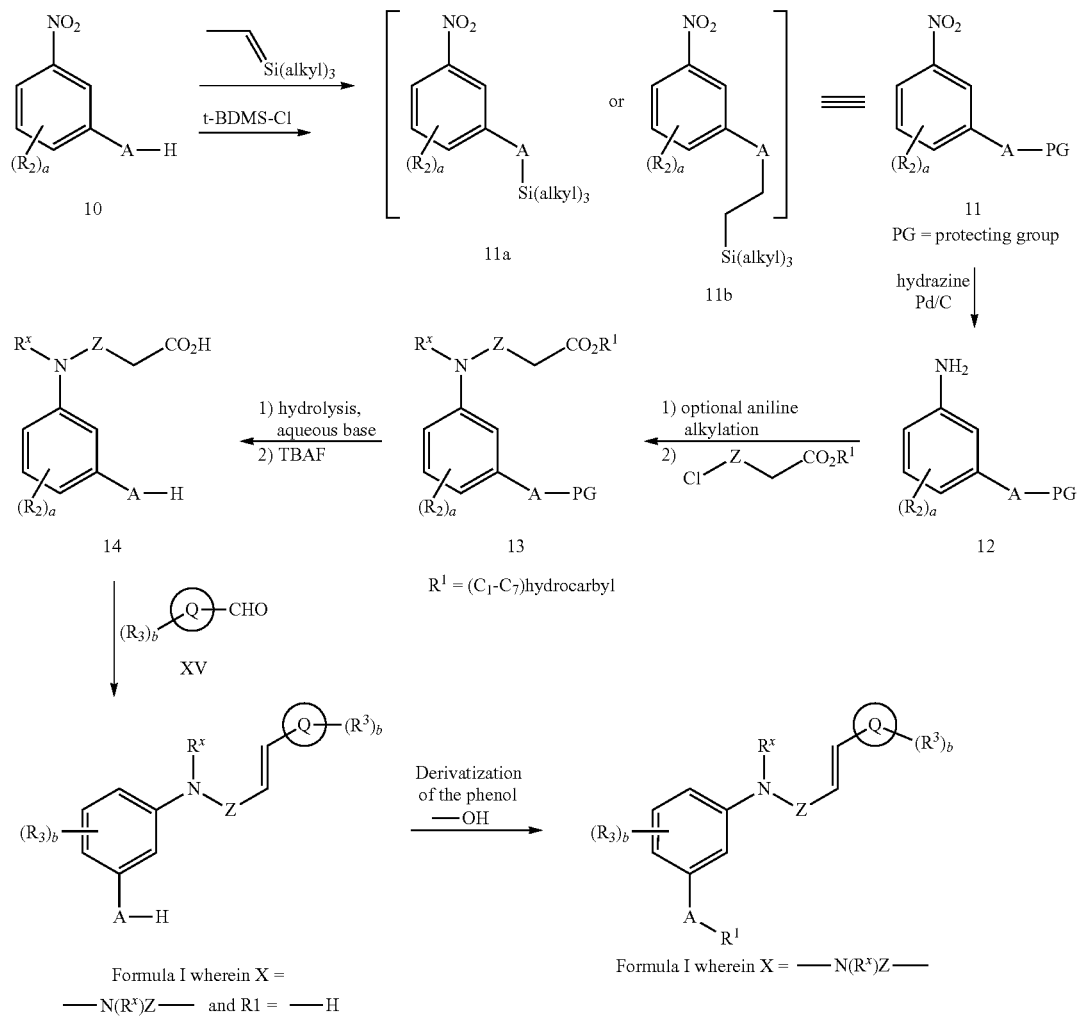

Scheme 12

According to Scheme 12, a starting 3-nitrophenol or 3-nitrothiophenol, 10, is first derivatized to protect the phenol or thiophenol moiety. Phenol and thiophenol compounds, 10 are reacted with a trialkylsilyl halide, preferably tert-butyldimethylsilylchloride (t-BDMS-Cl), or with a vinyltrialkylsilane, preferably vinyl tert-butyldimethylsilane or vinyl trimethylsilane, to produce the corresponding trialkylsilylethyl protected compound, 11b.

The protected compound, 11, is treated with a reducing agent capable of reducing an aromatic nitro group to the corresponding aromatic amino group. Suitable agents include noble metal catalyzes reducing agents, e.g., hydrazine and palladium metal. Preferably the reaction is performed in a solvent, e.g., THF or a lower alcohol such as, for example methanol or ethanol. The reduction provides the aniline derivative, 12.

The aniline derivative, 12, is optionally alkylated to provide an intermediate having a —R$^x$ substituent on the aniline nitrogen. Suitable alkylations of an aniline nitrogen include: (a) alkylation with an alkyl moiety having a leaving group, e.g., for example, an alkyl halide or an alkyl mesylate; and (b) reductive amination, i.e., reaction with an aldehyde or a ketone in the presence of a reducing agent capable of selectively reducing the imine formed by reaction of the aldehyde or ketone with the aniline. By "selective reduction" is meant that a suitable reducing agent will, under the reaction conditions, reduce the imine intermediate faster than it will reduce the starting aldehyde. Suitable reducing agents include, for example NaBH$_3$CN and sodium triacetoxy borohydride.

Alternatively, a reductive amination reaction may be performed directly on the aromatic nitro compound 11, wherein the nitro group is reduced and alkylated in a one-pot procedure.

The optionally-alkylated aniline is then reacted with a compound according to Formula XII wherein the leaving group is preferably chloro. Particular compounds of Formula XII include ethylmalonyl chloride (to form a compound according to Formula 13, wherein Z is —C(=O)—) and ethyl-2-chlorosulfonylacetate (to form a compound according to Formula 13, wherein Z is —SO$_2$—).

According to Scheme 12, carboxylic ester compound 13 is hydrolyzed to form the corresponding carboxylic acid compound solvent. Hydrolysis is preferably performed under basic conditions. Suitable bases include LiOH, NaOH and KOH. The hydrolysis is preferably performed in an aqueous solvent, which may be water or a mixture of water and a water-miscible organic solvent such as methanol, ethanol, THF or mixtures thereof.

The compound 13 is also deprotected to remove the thiophenol or phenol protecting group, PG, to provide the 3-hydroxy or 3-mercapto compound 14. Suitable deprotection reagents include TBAF and triethylamine trihydrofluoride.

The deprotected carboxylic acid compound 14, is then reacted with a suitable aryl or heteroaryl aldehyde in the presence of an amine, preferably piperidine, to produce a compound according to Formula I wherein $R^1$ is —H and X is —$NR^x$—Z—. The reaction is preferably performed in an organic solvent that forms an azeotrope with water. Such solvents include, for example, benzene, toluene and DCM. The reaction is preferably performed with some means of removing water as it is formed in the reaction. Suitable means of removing water include the use of a Dean-Stark trap or the use of a water-scavenging agent such as a molecular sieve. The compound, wherein $R^1$ is —H may subsequently be derivatized to provide additional compounds of Formula I as described herein.

(ii) Preparation of α,β-Unsaturated Sulfonamides and Propenamides of Formula IZ

Compounds of Formula IZ, wherein X is —$NR^xC(=O)$— or —$NR^xSO_2$—, may be prepared according to the method of Reddy et al., WO 03/072063, the entire disclosure of which is incorporated herein by reference. The synthesis comprises reaction of an appropriately substituted aniline with a compound according to Formula XXA wherein the exocyclic carbon-carbon double bond is in the (Z)-configuration, to form either a sulfonamide or an arylpropenamide compound according to Formula IZ. This procedure can also serve to produce compounds of Formula IE when the exocyclic carbon-carbon double bond of the intermediate compound according to Formula XXA is in the (E)-configuration. The synthesis is shown in Scheme 13.

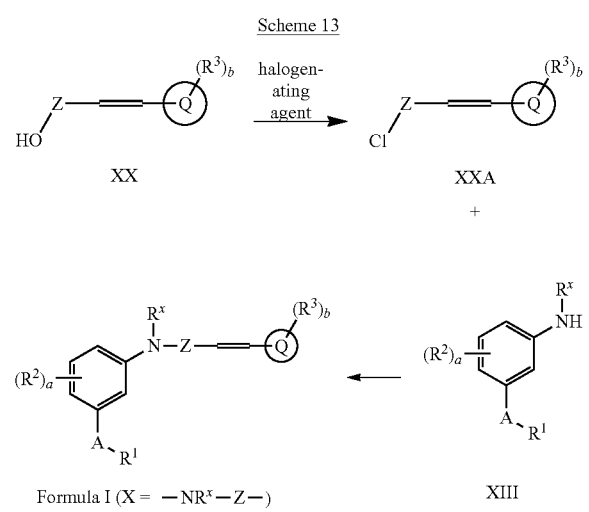

Scheme 13

Formula I (X = —$NR^x$—Z—)     XIII

According to Scheme 13, an intermediate (E)- or (Z)-aromatic acryloylhalide XXA or α,β-unsaturated sulfonyl halide XXA, may be prepared from the corresponding aromatic acrylic acid XX or α,β-unsaturated sulfonic acid XX. To do this, the sulfinic acid, XX is reacted with a halogenating agent such as, for example, thionyl chloride or phosphorous pentachloride, to form the intermediate XXA.

An aromatic amine of Formula XII is reacted with XXA. The reaction is preferably performed in the presence of an acid scavenger. Suitable acid scavengers include, for example, tertiary amines such as TEA, DIPEA, pyridine, or lutidine; inorganic bases such as sodium carbonate or potassium carbonate, or bases on a solid support, such as N,N-diisopropylethylaminomethylpolystyrene (PS-DIPEA). The reaction is preferably carried out in an organic solvent such as THF, toluene or DCM.

If $R^1$ is a thiophenol or phenol protecting group, such as, for example, a trialkylsilyl or a trialkylsilylethyl group, the product may be optionally deprotected and derivatized to produce additional compounds of formula I.

C. Preparation of Compounds of Formula I by Derivatization of Thiophenol or Phenol Compounds of Formula II.

Compounds of Formula II are derivatized by reacting the 3-hydroxy or 3-mercapto moiety of a compound according to Formula I wherein $R^1$ is —H, with various reagents to produce different compounds of Formula I.

Thus, according to a further embodiment of the invention, a process is provided for preparing a compound according to Formula I. or a salt thereof, via derivatization of a 3-hydroxy or 3-mercapto moiety of a compound such as, for example a compound according to Formula II:

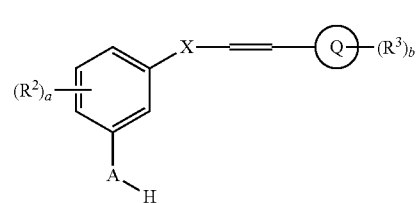

II comprising reacting the compound according to Formula II, or a salt thereof with an electrophilic compound according to Formula XXI:

$R^1$-L wherein $R^1$ is as herein defined for compounds of Formula I, provided $R^1$ is not —H; and L comprises a leaving group such that the reagent XXI will react with the phenol or thiophenol group of the compound according to Formula II, thereby derivatizing the thiophenol or phenol group thereof and forming a compound according to Formula I wherein $R^1$ is other than —H.

Compounds of Formula XXI include, for example:
(a) compounds wherein $R^1$ is alkyl functionalized by the leaving group L;
(b) compounds wherein $R^1$ is aryl or heteroaryl functionalized by the leaving group L, wherein L is other than acyl;
(c) compounds wherein $R^1$ is a carboxylic acid which is activated by the leaving group L;
(d) compounds wherein $R^1$ is a sulfonic acid which is activated by the leaving group L;
(e) compounds wherein $R^1$ is a carbamic acid which is activated by the leaving group, L;
(f) compounds wherein $R^1$ is a trialkyl silyl group which is activated by the leaving group L; or
(g) compounds wherein $R^1$ is a dihydrocarbylphosphityl group which is activated by the leaving group L.

Suitable leaving groups, L include, for example, halogen, mesyl, tosyl, nosyl, trifyl and acyl groups. Compounds of Formula XXI include, for example, silylhalides, such as t-BDMS-Cl; alkyl and arylalkyl halides such as alkyl bromides and benzyl bromides; acyl halides, such as acetyl chloride and other acid chlorides; sulfonyl halides, such as sulfonyl chlorides; acid anhydrides, sulfonic anhydrides; substituted alkanes having a sulfonate leaving group such as mesyl or tosyl; and phosphite esters, such as diethyl phosphites.

Representative examples of the types of derivatizations which may be employed to generate compounds of the invention, such as compounds according to Formulae III, IV, V and VI, are shown in Table 4.

TABLE 4

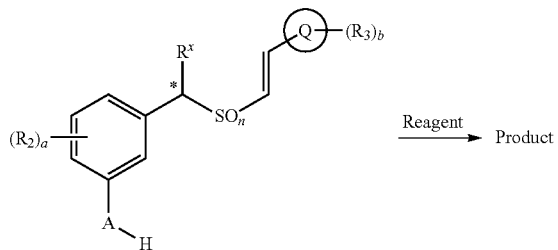

Reagent → Product

| Reagent | Product |
|---|---|
| A halo dialkyl phosphite, or a halodibenzyl phosphite produced in situ by reacting the dialkyl or dibenzyl phosphite with $CBr_4$ or $CCl_4$ in the presence of a base such as triethylamine. | 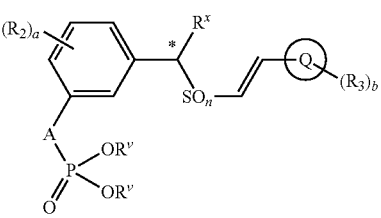 Phosphate compounds of Formula I, IIA and IIB. |
| Activated carboxylic acids, carbamic acids or carbonic acids; including carboxylic acids or amino acids in combination with amide coupling reagents. | 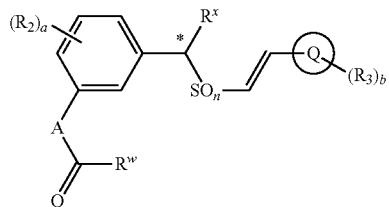 Ester, carbamate, carbonate compounds of Formula I, IIIA and IIIB |
| Activated sulfonic or sulfamic acids | 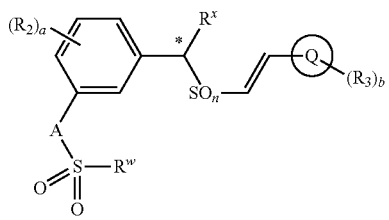 Sulfonate compounds of Formula I, IVA and IVB. |
| Alkyl compound activated with leaving group L. | 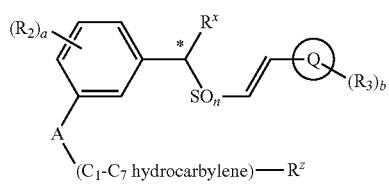 Ethers or thioethers of formula I, VA and VB. |

Accordingly there is provided a process for preparing a compound according to Formula III, or a salt thereof:

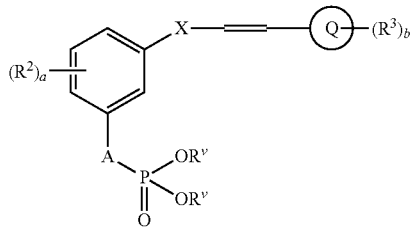

wherein $R^2$, $R^3$, X, A, Q, a and b are as defined herein for compounds of Formula I; and $R^v$ is —$(C_1$-$C_7)$hydrocarbyl. The method comprises the steps of:

(a) reacting a compound according to Formula II:

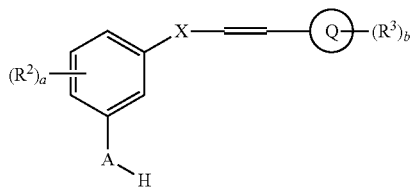

wherein, wherein $R^2$, $R^3$, X, A, Q, a and b are as defined herein for compounds of Formula I, with a dihydrocarbylphosphityl halide:

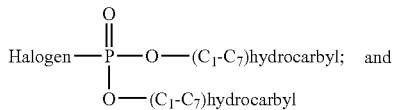

(b) isolating from the reaction products a compound of Formula III, or a salt thereof, wherein $R^v$ is —$(C_1$-$C_7)$hydrocarbyl.

There is further provided a process for preparing a compound according to Formula III, or a salt thereof, wherein $R^2$, $R^3$, X, A, Q, a and b are as defined herein for compounds of Formula I; and $R^v$ is —H. The method comprises the steps of:

(a) reacting a compound according to Formula III, wherein $R^v$ is —$(C_1$-$C_7)$hydrocarbyl, with a halotrialkyl silane:

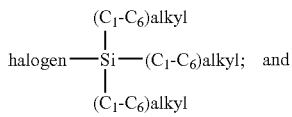

(b) isolating from the reaction products, a compound of Formula III, or a salt thereof, wherein $R^v$ is —H.

Preferably, the trihaloalkyl silane is selected from trialkyl silyl chlorides and trialkylsilyl bromides, more preferably trimethylsilylbromide.

VI. Conjugates of Formula I Compounds

Compounds according to Formula I may be reacted to form conjugates with an antibody (Ab). The antibody acts to deliver the therapeutically active drug molecule to the particular target cell population with which the antibody reacts.

A. Antibodies Suitable for Conjugation with Formula I Compounds

The antibody may be any antibody that binds to, complexes with or reacts with a receptor, antigen or ether receptive moiety associated with an abnormally proliferative cell population sought to be treated and, which possesses at least one chemically reactive moiety, preferably a free reactive sulfhydryl (—SH), amino (—$NH_2$) group or carboxyl (—$CO_2H$) group. Particularly preferred antibodies are those which can recognize a tumor-associated antigen.

The antibody may belong to any recognized class or subclass of immunoglobulins such as IgG, IgA, IgM, IgD, or IgE. The antibody can be derived from any species. Preferably, however, the antibody is of human, murine, or rabbit origin, most preferably of human origin. The antibody may be polyclonal or monoclonal, preferably monoclonal.

The invention also encompasses the use of antigen recognizing antibody fragments. Such fragments may include, for example, the Fab', F(ab')$_2$, $F_v$, or Fab fragments, or other antigen recognizing antibody fragments.

Such antibody fragments may be prepared, for example, by proteolytic enzyme digestion, for example, by pepsin or papain digestion, reductive alkylation, or recombinant techniques. Monoclonal antibodies (Mabs) may be advantageously cleaved by proteolytic enzymes to generate fragments retaining the antigen-binding site. For example, proteolytic treatment of IgG antibodies with papain at neutral pH generates two identical "Fab" fragments, each containing one intact light chain disulfide-bonded to a fragment of the heavy chain (Fd). Each Fab fragment contains one antigen-binding site. The remaining portion of the IgG molecule is a dimer known as "Fc". Similarly, pepsin cleavage at pH 4 results in a F(ab')2 fragment. The materials and methods for preparing such fragments are well-known to those skilled in the art. See generally, Parham, *J. Immunology*, 131, 2895 (1983); Lamoyi et al., *J. Immunological Methods*, 56, 235 (1983); Parham, Id., 53, 133 (1982); Goding, Monoclonal Antibodies Principles and Practice, Academic Press (1983), p. 119-123; and Matthew et al., Id., 50, 239 (1982).

The antibody may be a single chain antibody ("SCA"). These may consist of single chain Fv fragments ("scFv") in which the variable light ($V_L$) and variable heavy ($V_H$) domains are linked by a peptide bridge or by disulfide bonds. The antibody may consist of single $V_H$ domains (dAbs) which possess antigen-binding activity. See, e.g., G. Winter and C. Milstein, *Nature*, 349, 295 (1991); R. Glockshuber et al., *Biochemistry* 29, 1362 (1990); and E. S. Ward et al., *Nature* 341, 544 (1989), the entire disclosures of which are incorporated herein by reference.

Also, the antibody may be a "bifunctional" or "hybrid" antibody, i.e., an antibody which may have one arm having a specificity for one antigenic site, such as a tumor associated antigen while the other arm recognizes a different target, for example, a hapten which is, or to which is bound, an agent lethal to the antigen-bearing tumor cell. Alternatively, a bifunctional antibody may be one in which each arm has specificity for a different epitope of a tumor associated antigen of the abnormally proliferative cell to be treated.

Bifunctional antibodies are described, for example, in European Patent Publication, EP 0105360, the entire disclosure of which is incorporated herein by reference. Such hybrid or bifunctional antibodies may be derived, biologically, by cell fusion techniques, or chemically, particularly with cross-linking agents or disulfide bridge-forming reagents. Bifunctional antibodies may comprise whole antibodies and fragments thereof. Methods for obtaining such hybrid antibodies are disclosed, for example, in PCT application W083/03679, published Oct. 27, 1983, and published European Application EPA 0 217 577, published Apr. 8, 1987, the entire disclosures of which are incorporated herein by reference.

The antibody may be a chimeric antibody. Chimeric animal-human monoclonal antibodies may be prepared by conventional recombinant DNA and gene transfection techniques well known in the art. The variable region genes of a mouse antibody-producing myeloma cell line of known antigen-binding specificity are joined with human immunoglobulin constant region genes. When such gene constructs are transfected into mouse myeloma cells, antibodies are produced which are largely human but contain antigen-binding specificities generated in mice. As demonstrated by Morrison et al., *Proc. Natl. Acad. Sci. USA* 81, 6851-6855, 1984, both chimeric heavy chain V region exon (VH)-human heavy chain C region genes and chimeric mouse light chain V region exon (V*)-human * light chain gene constructs may be expressed when transfected into mouse myeloma cell lines. When both chimeric heavy and light chain genes are transfected into the same myeloma cell, an intact $H_2L_2$ chimeric antibody is produced. The methodology for producing such chimeric antibodies by combining genomic clones of V and C region genes is described in the above-mentioned paper of Morrison et al., and by Boulianne et al., *Nature* 312, 642-646, 1984. Also see Tan et al., *J. Immunol.* 135, 3564-3567, 1985 for a description of high level expression from a human heavy chain promoter of a human-mouse chimeric chain after transfection of mouse myeloma cells. As an alternative to combining genomic DNA, cDNA clones of the relevant V and C regions may be combined for production of chimeric antibodies, as described by Whitte et al., *Protein Eng.* 1, 499-505, 1987 and Liu et al., *Proc. Natl. Acad. Sci. USA* 84, 3439-3443, 1987.

For examples of the preparation of chimeric antibodies, see the following U.S. Pat. Nos. 5,292,867; 5,091,313; 5,204,244; 5,202,238; and 5,169,939. The entire disclosures of these patents, and the publications mentioned in the preceding paragraph, are incorporated herein by reference. The invention is not to be construed as limited in scope by any particular method of production of an antibody whether bifunctional, chimeric, bifunctional-chimeric, humanized, or an antigen-recognizing fragment or derivative thereof.

To further reduce the immunogenicity of murine antibodies, "humanized" antibodies have been constructed in which only the minimum necessary parts of a mouse antibody, the complementarity-determining regions (CDRs), are combined with human V region frameworks and human C regions (Jones et al., *Nature* 321, 522-525, 1986; Verhoeyen et al., *Science* 239, 1534-1536, 1988; Reichmann et al., 322, 323-327, 1988; Hale et al., *Lancet* 2, 1394-1399, 1988; Queen et al., *Proc. Natl. Acad. Sci. USA* 86, 10029-10033, 1989). The entire disclosures of the aforementioned papers are incorporated herein by reference. This technique results in the reduction of the xenogeneic elements in the humanized antibody to a minimum. Rodent antigen binding sites are built directly into human antibodies by transplanting only the antigen binding site, rather than the entire variable domain, from a rodent antibody. This technique is available for production of chimeric rodent/human antibodies of reduced human immunogenicity.

Representative antibodies and antigen-binding fragments thereof which target tumor antigens or tumor-associated antigens, and are commercially available, include: Satumomab Pendetide (by Cytogen, a murine Mab directed against TAG-72); Igovomab (by CIS Bio, a murine Mab fragment Fab2 directed against tumor-associated antigen CA 125); Arcitumomab (by Immunomedics, a murine Mab fragment Fab directed against human carcinoembryonic antigen CEA); Capromab Pentetate (by Cytogen, a murine Mab directed against tumor surface antigen PSMA); Tecnemab KI (by Sorin, murine Mab fragments (Fab/Fab2 mix) directed against HMW-MAA); Nofetumomab (by Boehringer Ingelheim/NeoRx, murine Mab fragments (Fab) directed against carcinoma-associated antigen); Rituximab (by Genentech/IDEC Pharmaceuticals, a chimeric Mab directed against CD20 antigen on the surface of B lymphocytes); Trastuzumab (by Genintech, a humanized antibody directed against human epidermal growth factor receptor 2 (HER 2)); Votumumab (by Organon Teknika, a human Mab directed against cytokeratin tumor-associated antigen); Ontak (by Seragen/Ligand Pharmaceuticals, an IL-2-diphtheria toxin fusion protein that targets cells displaying a surface IL-2 receptor); IMC-C225 (by Imclone, a chimerized monoclonal antibody that binds to EGFR); LCG-Mab (by Cytoclonal Pharmaceutics Monoclonal antibody directed against lung cancer gene LCG); ABX-EGF (by Abgenix, a fully human monoclonal antibody against the epidermal growth factor receptor (EGFr)); and Epratuzumab (by Immunomedics, a humanized, anti-CD22 monoclonal antibody).

According to one embodiment of the invention the antibody comprises a tumor-specific antibody, preferably a tumor-specific monoclonal antibody or a tumor-specific monospecific polyclonal antibody. Particularly preferred monoclonal antibodies for use in the present invention, which recognize tumor associated antigens, include, for example, those listed in Table 1. All references cited in Table 5 are incorporated herein in their entirety, by reference.

TABLE 5

| Antigen Site Recognized | Monoclonal Antibodies | Reference |
|---|---|---|
| Lung Tumors | KS1/4 | N. M. Varki, et al., Cancer Res., 44: 681, 1984 |
|  | 534, F8; 604A9 | F. Cuttitta, et al., in: G. L. Wright (ed) Monoclonal Antibodies and Cancer, Marcel Dekker, Inc., NY., p-161, 1984. |
| Squamous Lung | G1, LuCa2, LuCa3, LuCa4 | Kyoizumi et al., Cancer Res., 45: 3274, 1985. |
| Small Cell Lung | TFS-2 | Okabe et al., Cancer Res. Cancer, 45: 1930, 1985. |
| Colon Cancer | 11.285.14, 14.95.55 | G. Rowland, et al., Cancer, Immunol. Immunother., 19: 1, 1985 |
|  | NS-3a-22, NS-10, NS-19-9, NS-33a, NS-52a, 17-1A | Z. Steplewski, et al., Cancer, Res., 41: 2723, 1981. |
| Carcinoembryonic | MoAb 35 or ZCE025 | Acolla, R. S. et aL, Proc., Natl. Acad. Sci., (USA), 77: 563, 1980. |
| Melanoma | 9.2.27 | T. F. Bumol and R. A. Reisfeld, Proc. Natl. Acad. Sci., (USA), 79: 1245, 1982. |
| p97 | 96.5 | K. E. Hellstrom, et al., Monoclonal Antibodies and Cancer, loc. cit. p. 31. |
| Antigen T65 | T101 | Boehringer-Mannheim, P.O. Box 50816, Indianapolis, IN 46250 |
| Ferritin | Antiferrin | Boehringer-Mannheim, P.O. Box 50816, Indianapolis, IN 46250 |

TABLE 5-continued

| Antigen Site Recognized | Monoclonal Antibodies | Reference |
|---|---|---|
| | R24 | W. G. Dippold, et al., Proc. Natl. Acad. Sci. (USA), 77: 6114, 1980 |
| Neuroblastoma | P1 153/3 | R. H. Kennet and F. Gilbert, Science, 203: 1120, 1979. |
| | MIN 1 | J. T. Kemshead in Monoclonal, Antibodies and Cancer, loc. cit., p. 49. |
| | UJ13A | Goldman et al., Pediatrics, 105: 252, 1984. |
| Glioma | BF7, GE2, CG12 | N. de Tribolet, et al., in Monoclonal Antibodies and Cancer, loc. cit. p. 81. |
| Ganglioside | L6 | I. Hellstrom et al., Proc. Natl Acad. Sci. (U.S.A), 83: 7059 (1986); U.S. Pat. Nos. 4,906,562, and 4,935,495. |
| | Chimeric L6 | PCT Patent Publication, WO 88/03145 and U.S. Pat. No. 5,242,824 |
| Lewis Y | BR64 | U.S. Pat. No. 5,242,824 |
| Fucosylated Lewis Y | BR96, Chimeric BR96 | PCT Patent Publication, WO 91/00295. |
| Breast Cancer | B6.2, B72.3 | D. Colcher, et al., in Monoclonal Antibodies and Cancer, loc. cit. p. 121. |
| Osteogenic Sarcoma | 791T/48 791T/36 | M. J. Embleton, ibid, p. 181 |
| Leukemia | CALL 2 | C. T. Teng, et al, Lancet, 1: 01, 1982. |
| | anti-idiotype | R. A. Miller, et al., N. Eng. J. Med., 306: 517, 1982 |
| Ovarian Cancer | OC 125 | R. C. Bast, et al., J. Clin. Invest., 68: 1331, 1981. |
| Prostate Cancer | D83.21, P6.2, Turp-27 | J. J. Starling, et al., in Monoclonal Antibodies and Cancer, loc. cit., p. 253. |
| Renal Cancer | A6H, D5D | P. H. Lange, et al., Surgery, 98: 143, 1985. |

B. Linking a Formula I Compound to an Antibody (Ab)

An antibody may be covalently linked to a compound of Formula I, via a covalent linker (L) to form a conjugate of the Formula I-L-Ab. Structural components of substituents on the phenyl or Q rings of compounds of Formula I (e.g., —OH, —SH, and substituents comprising amino acid or peptidyl moieties) provide attachment points whereby an antibody may be attached to a compound of Formula I through a linking moiety L.

The compounds of Formula I can readily be covalently bonded to antibodies via a suitable bifunctional linker (-L-) to yield a conjugate of general Formula, I-L-Ab. In addition, compounds of Formulae IIA, IIB, IIIA, IIIB, IVA, IVB, VA, VB, VIA and VIB can be covalently bonded to antibodies (Ab) via a suitable bifunctional linker (-L-) to yield conjugates of general Formula, IIA-L-Ab, IIB-L-Ab, IIIA-L-Ab, IIIB-L-Ab, IVA-L-Ab, IVB-L-Ab, VA-L-Ab, VB-L-Ab, VIA-L-Ab, and VIB-L-Ab.

The covalent linker (L) provided between a compound according to Formula I and an antibody (Ab) to form a conjugate of the Formula I-L-Ab may, in its simplest form, comprise a single covalent bond connecting the compound according to Formula I to the antibody.

An example of a covalent bond formed as a linker between a compound according to Formula I and an antibody is a disulfide bond. A disulfide bond may be formed by the oxidation of an antibody and a compound according to Formula I, wherein a substituent on the phenyl ring or Q-ring of Formula I comprises a peptidyl moiety containing one or more cysteine amino acids. The cysteine residues can be oxidized to form disulfide links by dissolving 1 mg of the a suitable compound according to Formula I and 0.5 equivalents of the desired antibody in 1.5 mL of 0.1% (v/v) 17.5 mM acetic acid, pH 8.4, followed by flushing with nitrogen and then 0.01 M $K_2Fe(CN)_6$. After incubation for one hour at room temperature, the adduct peptide is purified, e.g., by HPLC.

Another example of a suitable covalent bond formed as a linker between a compound according to Formula I and an antibody is an amide bond. An amide bond may be formed by reacting an amino group on a compound of the invention with a carboxylic acid group which forms part of the primary structure of the antibody (Ab) (e.g., for example a glutamic or aspartic amino acid residue). Alternately, an amide bond may be formed if the reacting moieties were reversed, i.e., the compound according to Formula I contains a carboxylic acid functionality and reacts with an amino functionality within the Ab structure.

More commonly, the compound according to Formula I is attached to the antibody using a suitable bifunctional linking reagent. The term "bifunctional linking reagent" refers to a molecule that comprises two reactive moieties which are connected by a spacer element. The term "reactive moieties" in this context, refers to chemical functional groups capable of coupling with an antibody or a compound according to Formula I by reacting with functional groups on the antibody and the compound according to Formula I. Therefore, according to one embodiment of the invention, a compound according to Formula I, wherein a substituent on the phenyl ring or Q-ring of Formula I comprises an —OH, —$NH_2$, or —SH moiety, is coupled to an antibody using a bifunctional linking reagent. Procedures for preparation of immunoconjugates using these linkers is are detailed in Toxin-Targeted Design for Anticancer Therapy. II: Preparation and Biological Comparison of Different Chemically Linked Gelonin-Antibody Conjugates (Cattel, et al, *J. Pharm. Sci.*, 82:7, p 699-704, 1993), (the entire disclosure of which is incorporated herein by reference).

Conjugates according to the invention may be prepared by utilizing homo-bifunctional linking reagents (wherein the two reactive moieties on the bifunctional linking reagent are the same), such as, for example, disuccinimidyl tartrate, disuccinimidyl suberate, ethylene glycol-bis-(succinimidyl succinate), 1,5-difluoro-2,4-dinitrobenzene ("DFNB"), 4,4'-diisothiocyano-2,2'-disulfonic acid stilbene ("DIDS"), and bis-maleimidohexane ("BMH"). The linking reaction occurs randomly between the Ab and a compound according to Formula I having a peptidyl moiety as part of at least on substituent on the phenyl ring or the Q ring of Formula I.

Hetero-bifunctional linking reagents (wherein the two reactive moieties on the bi-functional linking reagent are different) may also be employed in preparing conjugates according to the invention. For hetero-bifunctional linking, a compound according to Formula I is derivatized with, for example, the N-hydroxysuccinimidyl portion of the bifunctional reagent, and the resulting derivatized Formula I compound is purified by chromatography. Next, a suitable antibody is reacted with the second functional group of the bifunctional linking reagent, assuring a directed sequence of reaction between the compound of Formula I, the linker and the antibody (Ab).

Typical hetero-bifunctional linking agents for forming conjugates between a compound and an antibody have an amino-reactive N-hydroxysuccinimide ester (NHS-ester) as one functional group and a sulfhydryl reactive group as the other functional group. First, amino groups of the Formula I compound are acylated with the NHS-ester group of the cross-linking agent. The antibody, possessing free sulfhydryl groups, is reacted with the sulfhydryl reactive group of the cross-linking agent to form a covalently cross-linked dimer. Common thiol reactive groups include for example, maleimides, pyridyl disulfides, and active halogens. For example, MBS contains a NHS-ester as the amino reactive group, and a maleimide moiety as the sulfhydryl reactive group.

Numerous bifunctional linkers, useful as linkers (-L-), exist which have been used specifically for coupling small molecules to monoclonal antibodies. Many of these linkers are commercially available. Examples include N-succinimidyl-3-(2-pyridyldithio)-propionate (SPDP), 2-iminothiolane (2-IT), 3-(4-carboxamidophenyldithio)propionthioimidate (CDPT), N-succinimidyl-acetylthioacetate (SATA), ethyl-5-acetyl-propionthioimidate (AMPT) and N-succinimidyl-3-(4-carboxamidophenyldithio)propionate (SCDP), sulfosuccinimidyl-2-(p-azidosalicylamido)ethyl-1-3'-dithiopropionate ("SASD", Pierce Chemical Company, Rockford, Ill.), N-maleimidobenzoyl-N-hydroxysuccinimidyl ester ("MBS"), m-maleimidobenzoylsulfosuccinimide ester ("sulfo-MBS"), N-succinimidyl(4-iodoacetyl)aminobenzoate ("SIAB"), succinimidyl 4-(N-maleimidomethyl)-cyclohexane-1-carboxylate ("SMCC"), succinimidyl-4-(p-maleimidophenyl)butyrate ("SMPB"), sulfosuccinimidyl(4-iodoacetyl)amino-benzoate ("sulfo-SIAB"), sulfosuccinimidyl 4-(N-maleimidomethyl)cyclohexane-1-carboxylate ("sulfo-SMCC"), sulfosuccinimidyl 4-(p-maleimidophenyl)-butyrate ("sulfo-SMPB"), bromoacetyl-p-aminobenzoyl-N-hydroxysuccinimidyl ester, and iodoacetyl-N-hydroxysuccinimidyl ester.

Photoactive hetero-bifunctional linking reagents, e.g., photoreactive phenyl azides, may also be employed. One such reagent, SASD, may be linked, via its NHS-ester group, to either an antibody or to a Formula I compound wherein at least one substituent on Q or the phenyl ring of Formula I comprises a peptidyl moiety. The conjugation reaction is carried out at pH 7 at room temperature for about 10 minutes. Molar ratios between about 1 and about 20 of the cross-linking agent to the compounds to be linked may be used.

Exemplary synthetic routes for preparing conjugates of the present invention of general Formula I-L-Ab are shown in Scheme 14. According to Scheme 14, a monoclonal antibody Mab, wherein A is —NH— or —S—, is derivatized by reaction with the linker reagent CDPT or SCDP. A compound according to Formula I, wherein A is —NH— or —S—, is derivatized by reaction with the linker reagent CDPT, SATA or AMPT. Coupling of the derivatized compound of Formula I with the derivatized monoclonal antibody produces a conjugate according to Formula I-L-Ab.

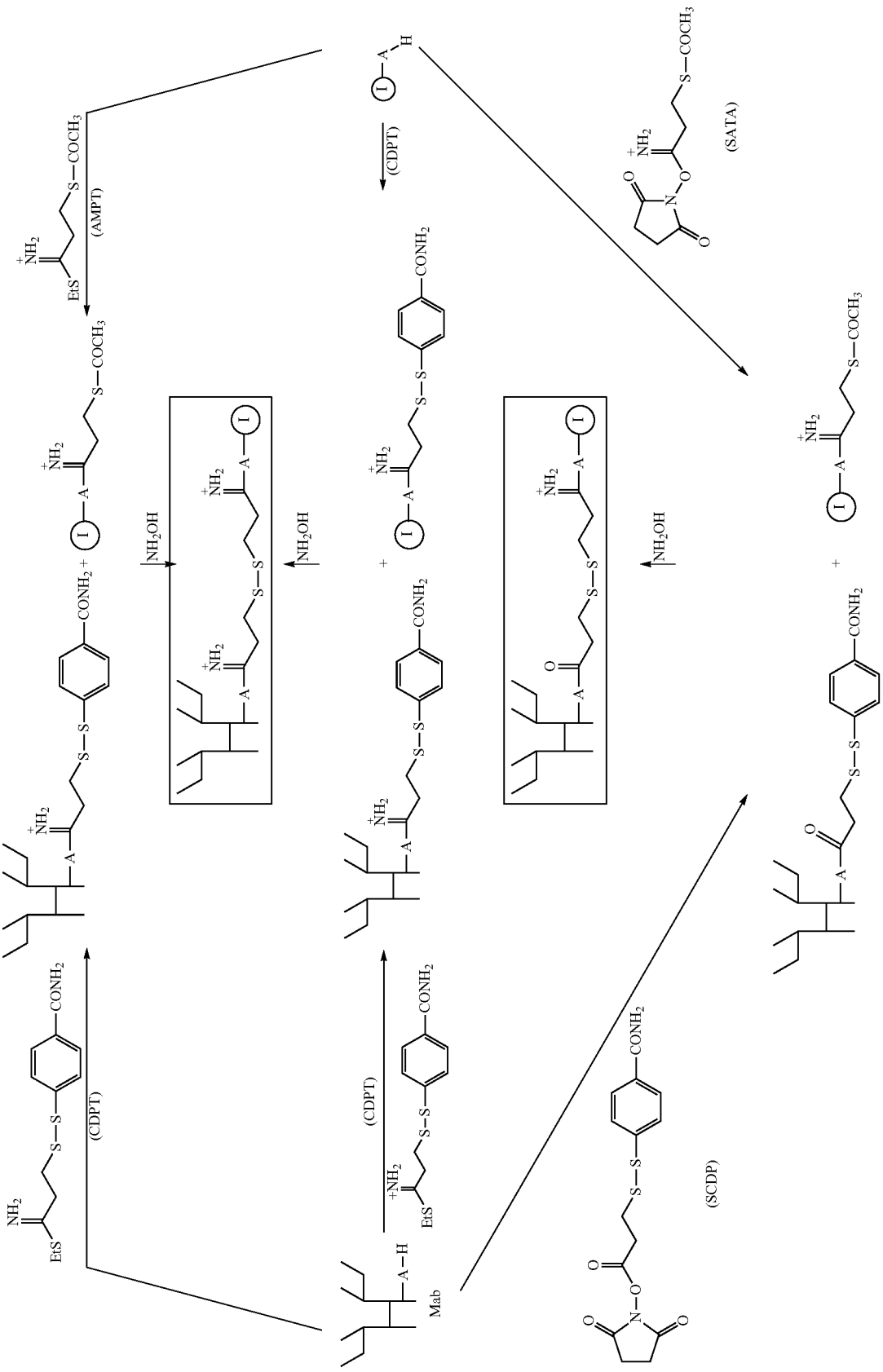

VII. Salts of Compounds of the Invention

The compounds of the present invention may take the form of salts. The term "salts", embraces salts commonly used to form alkali metal salts and to form addition salts of free acids or free bases. The term "pharmaceutically-acceptable salt" refers to salts which possess toxicity profiles within a range so as to have utility in pharmaceutical applications. Pharmaceutically unacceptable salts may nonetheless possess properties such as high crystallinity, which have utility in the practice of the present invention, such as for example utility in a synthetic process. Suitable pharmaceutically-acceptable acid addition salts may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, example of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, benzenesulfonic, pantothenic, 2-hydroxyethanesulfonic, toluenesulfonic, sulfanilic, cyclohexylaminosulfonic, stearic, alginic, B-hydroxybutyric, salicyclic, galactaric and galacturonic acid. Examples of pharmaceutically unacceptable acid addition salts include, for example, perchlorates and tetrafluoroborates.

Suitable pharmaceutically acceptable base addition salts of compounds of the invention include for example, metallic salts made from calcium, magnesium, potassium, sodium and zinc or organic salts made from N,N'-dibenzylethylenediamine, chloroprocaine, choline, diethanolamine, ethylenediamine, meglumine (N-methylglucamine) and procaine. Examples of pharmaceutically unacceptable salts include lithium salts and cyanate salts. All of these salts may be prepared by conventional means from the corresponding compound according to Formula I by reacting, for example, the appropriate acid or base with the compound according to Formula I.

VIII. Administration of Compounds and Conjugates of the Invention

The compounds and conjugates of the invention may be administered by any route, including oral and parenteral administration. Parenteral administration includes, for example, intravenous, intramuscular, intraarterial, intraperitoneal, intranasal, rectal, intravaginal, intravesical (e.g., to the bladder), intradermal, topical or subcutaneous administration. Also contemplated within the scope of the invention is the instillation of drug in the body of the patient in a controlled formulation, with systemic or local release of the drug to occur at a later time. For example, the drug may be localized in a depot for controlled release to the circulation, or for release to a local site of tumor growth.

One or more compounds or conjugates, useful in the practice of the present inventions, may be administered simultaneously, by the same or different routes, or at different times during treatment.

For parenteral administration, the active agent may be mixed with a suitable carrier or diluent such as water, an oil (particularly a vegetable oil), ethanol, saline solution, aqueous dextrose (glucose) and related sugar solutions, glycerol, or a glycol such as propylene glycol or polyethylene glycol. Solutions for parenteral administration preferably contain a water soluble salt of the active agent. Stabilizing agents, antioxidizing agents and preservatives may also be added. Suitable antioxidizing agents include sulfite, ascorbic acid, citric acid and its salts, and sodium EDTA. Suitable preservatives include benzalkonium chloride, methyl- or propylparaben, and chlorbutanol. The composition for parenteral administration may take the form of an aqueous or nonaqueous solution, dispersion, suspension or emulsion.

For oral administration, the active agent may be combined with one or more solid inactive ingredients for the preparation of tablets, capsules, pills, powders, granules or other suitable oral dosage forms. For example, the active agent may be combined with at least one excipient such as fillers, binders, humectants, disintegrating agents, solution retarders, absorption accelerators, wetting agents absorbents or lubricating agents. According to one tablet embodiment, the active agent may be combined with carboxymethylcellulose calcium, magnesium stearate, mannitol and starch, and then formed into tablets by conventional tableting methods.

The specific dose of a compound according to the invention to obtain therapeutic benefit for treatment of a proliferative disorder will, of course, be determined by the particular circumstances of the individual patient including, the size, weight, age and sex of the patient, the nature and stage of the proliferative disorder, the aggressiveness of the proliferative disorder, and the route of administration of the compound.

For example, a daily dosage of from about 0.05 to about 50 mg/kg/day may be utilized. Higher or lower doses are also contemplated.

A. Radioprotection

The specific dose of compound according to the invention to obtain therapeutic benefit for radioprotection will be determined by the particular circumstances of the individual patient including, the size, weight, age and sex of the patient, the type, dose and timing of the ionizing radiation, and the route of administration of the compound of the invention.

For example, a daily dosage of from about 0.05 to about 50 mg/kg/day may be utilized. Higher or lower doses are also contemplated.

Exposure to radiation by an individual may comprise therapeutic radiation administered to the individual or in some indications, to bone marrow removed from the individual.

An individual may also be exposed to ionizing radiation from occupation or environmental sources, as discussed in the Background of the Invention, above. For purposes of the invention, the source of the radiation is not as important as the type (i.e., acute or chronic) and dose level absorbed by the individual. It is understood that the following discussion encompasses ionizing radiation exposures from both occupational and environmental sources.

Individuals suffering from effects of acute or chronic exposure to ionizing radiation that are not immediately fatal are said to have remediable radiation damage. Such remediable radiation damage can be reduced or eliminated by the compounds and methods of the present invention.

An acute dose of ionizing radiation which may cause remediable radiation damage includes a localized or whole body dose, for example, between about 10,000 millirem (0.1 Gy) and about 1,000,000 millirem (10 Gy) in 24 hours or less, preferably between about 25,000 millirem (0.25 Gy) and about 200,000 (2 Gy) in 24 hours or less, and more preferably between about 100,000 millirem (1 Gy) and about 150,000 millirem (1.5 Gy) in 24 hours or less.

A chronic dose of ionizing radiation which may cause remediable radiation damage includes a whole body dose of about 100 millirem (0.001 Gy) to about 10,000 millirem (0.1 Gy), preferably a dose between about 1000 millirem (0.01

Gy) and about 5000 millirem (0.05 Gy) over a period greater than 24 hours, or a localized dose of 15,000 millirem (0.15 Gy) to 50,000 millirem (0.5 Gy) over a period greater than 24 hours.

(i) Radioprotection: Therapeutic Ionizing Radiation

For radioprotective administration to individuals receiving therapeutic ionizing radiation, the compounds of the invention should be administered far enough in advance of the therapeutic radiation such that the compound is able to reach the normal cells of the individual in sufficient concentration to exert a radioprotective effect on the normal cells. The pharmacokinetics of specific compounds may be determined by means known in the art and tissue levels of a compound in a particular individual may be determined by conventional analyses.

The compound may be administered as much as about 24 hours, preferably no more than about 18 hours, prior to administration of the radiation. In one embodiment, the therapy is administered at least about 1, 2, 3, 4, 5, 6, 7, 8, 9, 10, 11 or 12 hours before administration of the therapeutic radiation. Most preferably, the compound is administered once at about 18 hours and again at about 6 hours before the radiation exposure.

One or more compounds of Formula I may be administered simultaneously, or different compounds of Formula I may be administered at different times during the treatment.

Where the therapeutic radiation is administered in serial fashion, it is preferable to intercalate the administration of one or more radioprotective compounds within the schedule of radiation treatments. As above, different radioprotective compounds of the invention may be administered either simultaneously or at different times during the treatment. Preferably, an about 24-hour period separates administration of the radioprotective compound and the therapeutic radiation. More preferably, the administration of the radioprotective compound and the therapeutic radiation is separated by about 6 to 18 hours. This strategy will yield significant reduction of radiation-induced side effects without affecting the anticancer activity of the therapeutic radiation.

For example, therapeutic radiation at a dose of 0.1 Gy may be given daily for five consecutive days, with a two-day rest, for a total period of 6-8 weeks. One or more compounds of Formula I may be administered to the individual 18 hours previous to each round of radiation. It should be pointed out, however, that more aggressive treatment schedules, i.e., delivery of a higher dosage, is contemplated according to the present invention due to the protection of the normal cells afforded by the radioprotective compounds. Thus, the radioprotective effect of the compound increases the therapeutic index of the therapeutic radiation, and may permit the physician to safely increase the dosage of therapeutic radiation above presently recommended levels without risking increased damage to the surrounding normal cells and tissues.

(ii) Radioprotection: Radiation-Treated Bone Marrow

The radioprotective compounds of the invention are further useful in protecting normal bone marrow cells from radiologic treatments designed to destroy hematologic neoplastic cells or tumor cells which have metastasized into the bone marrow. Such cells include, for example, myeloid leukemia cells. The appearance of these cells in the bone marrow and elsewhere in the body is associated with various disease conditions, such as the French-American-British (FAB) subtypes of acute myelogenous leukemias (AML), chronic myeloid leukemia (CML), and acute lymphocytic leukemia (ALL).

CML, in particular, is characterized by abnormal proliferation of immature granulocytes (e.g., neutrophils, eosinophils, and basophils) in the blood, bone marrow, spleen, liver, and other tissues and accumulation of granulocytic precursors in these tissues. The individual who presents with such symptoms will typically have more than 20,000 white blood cells per microliter of blood, and the count may exceed 400,000. Virtually all CML patients will develop "blast crisis", the terminal stage of the disease during which immature blast cells rapidly proliferate, leading to death.

Other individuals suffer from metastatic tumors, and require treatment with total body irradiation (TBI). Because TBI will also kill the individual's hematopoietic cells, a portion of the individual's bone marrow is removed prior to irradiation for subsequent reimplantation. However, metastatic tumor cells are likely present in the bone marrow, and reimplantation often results in a relapse of the cancer within a short time.

Individuals presenting with neoplastic diseases of the bone marrow or metastatic tumors may be treated by removing a portion of the bone marrow (also called "harvesting"), purging the harvested bone marrow of malignant stem cells, and reimplanting the purged bone marrow. Preferably, the individual is treated with radiation or some other anti-cancer therapy before the autologous purged bone marrow is reimplanted.

Thus, the invention provides a method of seducing the number of malignant cells in bone marrow, comprising the steps of removing a portion of the individual's bone marrow, administering an effective amount of at least one radioprotective compound according to the present invention and irradiating the treated bone marrow with a sufficient dose of ionizing radiation such that malignant cells in the bone marrow are killed. As used herein, "malignant cell" means any uncontrollably proliferating cell, such a tumor cell or neoplastic cell. The radioprotective compounds protect the normal hematopoietic cells present in the bone marrow from the deleterious effects of the ionizing radiation. The compounds also exhibit a direct killing effect on the malignant cells. The number of malignant cells in the bone marrow is significantly reduced prior to reimplantation, thus minimizing the occurrence of a relapse.

Preferably, each compound according to Formula I is administered to the bone marrow in a concentration from about 0.25 to about 100 micromolar; more preferably, from about 1.0 to about 50 micromolar; in particular from about 2.0 to about 25 micromolar. Particularly preferred concentrations are 0.5, 1.0 and 2.5 micromolar and 5, 10 and 20 micromolar.

The radioprotective compounds may be added directly to the harvested bone marrow, but are preferably dissolved in an organic solvent such as DMSO. Pharmaceutical formulations of compounds of Formula I, such as are described in more detail below may also be used.

Preferably, the radioprotective compound is added to the harvested bone marrow about 20 hours prior to radiation exposure, preferably no more than about 24 hours prior to radiation exposure. In one embodiment, the radioprotective compound is administered to the harvested bone marrow at least about 6 hours before radiation exposure. One or more compounds may be administered simultaneously, or different compounds may be administered at different times. Other dosage regimens are also contemplated.

If the individual is to be treated with ionizing radiation prior to reimplantation of the purged bone marrow, the individual may be treated with one or more radioprotective compounds prior to receiving the ionizing radiation dose, as described above.

(iii) Radioprotection: Environmental or Occupational Radiation Exposure

The invention also provides a method for treating individuals who have incurred remediable radiation damage from acute or chronic exposure to ionizing radiation, comprising reducing or eliminating the cytotoxic effects of radiation exposure on normal cells and tissues by administering an effective amount of at least one radioprotective compound. The compound is preferably administered in as short a time as possible following radiation exposure, for example between 0-6 hours following exposure.

Remediable radiation damage may take the form of cytotoxic and genotoxic (i.e., adverse genetic) effects in the individual. In another embodiment, there is therefore provided a method of reducing or eliminating the cytotoxic and genotoxic effects of radiation exposure on normal cells and tissues, comprising administering an effective amount of at least one radioprotective compound prior to acute or chronic radiation exposure. The compound may be administered, for example about 24 hours prior to radiation exposure, preferably no more than about 18 hours prior to radiation exposure. In one embodiment, the compound is administered at least about 6 hours before radiation exposure. Most preferably, the compound is administered at about 18 and again at about 6 hours before the radiation exposure. One or more radioprotective compounds may be administered simultaneously, or different radioprotective compounds may be administered at different times.

When multiple acute exposures are anticipated, the radioprotective compounds of the invention may be administered multiple times. For example, if fire or rescue personnel must enter contaminated areas multiple times, radioprotective compounds of the invention may be administered prior to each exposure. Preferably, an about 24-hour period separates administration of the compound and the radiation exposure. More preferably, the administration of radioprotective compounds and the radiation exposure is separated by about 6 to 18 hours. It is also contemplated that a worker in a nuclear power plant may be administered an effective amount of a radioprotective compound of the invention prior to beginning each shift, to reduce or eliminate the effects of exposure to ionizing radiation.

If an individual is anticipating chronic exposure to ionizing radiation, the radioprotective compound may be administered periodically throughout the duration of anticipated exposure. For example, a nuclear power plant worker or a soldier operating in a forward area contaminated with radioactive fallout may be given the radioprotective compound every 24 hours, preferably every 6-18 hours, in order to mitigate the effects of radiation damage. Likewise, the radioprotective compound may be periodically administered to civilians living in areas contaminated by radioactive fallout until the area is decontaminated or the civilians are removed to a safer environment.

B. Chemoprotection

The specific dose of a compound according to the invention to obtain therapeutic benefit for chemoprotection will be determined by the particular circumstances of the individual patient including, the size, weight, age and sex of the patient, the type and dose of the administered chemotherapy, the nature and stage and cell damage, and the route of administration of the compound of the invention.

For example, a daily dosage of from about 0.05 to about 50 mg/kg/day may be utilized. Higher or lower doses are also contemplated.

For providing cytoprotection from cytotoxic effects of chemotherapeutic agents, the schedule of administration of the cytotoxic drug, i.e., mitotic phase cell cycle inhibitor or topoisomerase inhibitor, can be any schedule with the stipulation that the compound according to Formula I is administered prior to the cytotoxic drug. The cytoprotective compound should be administered far enough in advance of the cytotoxic drug such that the former is able to reach the normal cells of the patient in sufficient concentration to exert a cytoprotective effect on the normal cells. Again, individual drug pharmacokinetics and blood levels of a specific drug in a specific patient are factors that may be determined by methods known in the art.

The cytoprotective compound is administered at least about 1 hour, preferably, at least about 2 hours, and more preferably, at least about 4 hours, before administration of the cytotoxic drug. The compound may be administered as much as about 48 hours, preferably no more than about 36 hours, prior to administration of the cytotoxic drug. Most preferably, the compound is administered about 24 hours before the cytotoxic drug. The compound may be administered more or less than 24 hours before the cytotoxic effect, but the protective effect of the compounds is greatest when administered about 24 hours before the cytotoxic drug. One or more cytotoxic drugs may be administered. Similarly, one or more of the compounds of Formula I may be combined.

Where the cytotoxic drug or drugs is administered in serial fashion, it may prove practical to intercalate cytoprotective compounds of the invention within the schedule with the caveat that a 4-48 hour period, preferably a 12-36 hour period, most preferably a 24 hour period, separates administration of the two drug types. This strategy will yield partial to complete eradication of cytotoxic drug side effects without affecting anticancer activity.

For example, the mitotic inhibitor may be given daily, or every fourth day, or every twenty-first day. The compound according to Formula I may be given 24 hours previous to each round of inhibitor administration, both as a cytoprotective agent and as an antitumor agent.

The compounds of the invention may be administered for therapeutic effect by any route, for example enteral (e.g., oral, rectal, intranasal, etc.) and parenteral administration. Parenteral administration includes, for example, intravenous, intramuscular, intraarterial, intraperitoneal, intravaginal, intravesical (e.g., into the bladder), intradermal, topical, subcutaneous or sublingual administration. Also contemplated within the scope of the invention is the instillation of drug in the body of the patient in a controlled formulation, with systemic or local release of the drug to occur at a later time. For anticancer use, the drug may be localized in a depot for controlled release to the circulation, or local site of tumor growth. When more than one compound according to Formula I is administered, or when one or more compounds of Formula I are administered in addition to one or more cytotoxic drugs, the different compounds may be administered by the same or different routes.

IX. Pharmaceutical Compositions

The compounds and conjugates of the invention may be administered in the form of a pharmaceutical composition, in combination with a pharmaceutically acceptable carrier. The active ingredient in such formulations may comprise from 0.1 to 99.99 weight percent. By "pharmaceutically acceptable carrier" is meant any carrier, diluent or excipient which is compatible with the other ingredients of the formulation and not deleterious to the recipient.

The active agent is preferably administered with a pharmaceutically acceptable carrier selected on the basis of the selected route of administration and standard pharmaceutical practice. The active agent may be formulated into dosage forms according to standard practices in the field of pharmaceutical preparations. See Alphonso Gennaro, ed., *Remington's Pharmaceutical Sciences*, 18th Ed., (1990) Mack Publishing Co., Easton, Pa. Suitable dosage forms may comprise, for example, tablets, capsules, solutions, parenteral solutions, troches, suppositories, or suspensions.

For parenteral administration, the active agent may be mixed with a suitable carrier or diluent such as water, an oil (particularly a vegetable oil), ethanol, saline solution, aqueous dextrose (glucose) and related sugar solutions, glycerol, or a glycol such as propylene glycol or polyethylene glycol. Solutions for parenteral administration preferably contain a water-soluble salt of the active agent. Stabilizing agents, antioxidizing agents and preservatives may also be added. Suitable antioxidizing agents include sulfite, ascorbic acid, citric acid and its salts, and sodium EDTA. Suitable preservatives include benzalkonium chloride, methyl- or propyl-paraben, and chlorbutanol. The composition for parenteral administration may take the form of an aqueous or nonaqueous solution, dispersion, suspension or emulsion.

For oral administration, the active agent may be combined with one or more solid inactive ingredients for the preparation of tablets, capsules, pills, powders, granules or other suitable oral dosage forms. For example, the active agent may be combined with at least one excipient such as fillers, binders, humectants, disintegrating agents, solution retarders, absorption accelerators, wetting agents absorbents or lubricating agents. According to one tablet embodiment, the active agent may be combined with carboxymethylcellulose calcium, magnesium stearate, mannitol and starch, and then formed into tablets by conventional tableting methods.

The practice of the invention is illustrated by the following non-limiting examples.

EXAMPLES

Example 1

Synthesis of (E)-5-((2,4,6-trimethoxystyrylsulfonyl)
methyl)-2-methoxyphenol

A. 3-O-tert-Butyldimethyl silyloxy-4-methoxy benzaldehyde

To a cooled (0° C.) solution of 3-hydroxy-4-methoxy benzaldehyde (10 g, 65.7 mmol, 1 eq) in dry DMF (75 mL) was added DIPEA (16.99 g, 131.4 mmol, 2 eq). The mixture was stirred under nitrogen for 10 min. A 1.0 M solution of t-BDMS-Cl in THF (78.9 mL, 1.2 eq) was added dropwise over 30 min. The resulting mixture was stirred 12-16 h and monitored by thin layer chromatography (TLC). When the reaction was complete, water (75 mL) was (3×75 mL). The combined organic layer was washed with saturated aqueous sodium bicarbonate (75 mL) and water (75 mL) and dried ($Na_2SO_4$). Volatile components were removed in vacuo to yield the crude product. The crude product was purified by column chromatography on silica eluted with $CHCl_3$ to afford the product (Yield; 26.75 g), 3-O-tert-butyldimethyl silyloxy-4-methoxy benzaldehyde, as a yellow oil.

B. 3-O-tert-butyldimethylsilyloxy-4-methoxy benzyl alcohol

To a cooled (0° C.) solution of 3-O-tert-butyldimethyl silyloxy-4-methoxy benzaldehyde (13 g, 48.8 mmol, 1 eq) in methanol (100 mL) under nitrogen, was added sodium borohydride (1 eq). The resulting mixture was allowed to warm to room temperature and stirred (30 min) and monitored by TLC. When the reduction was complete, water-ice was added to the reaction mixture. The resulting mixture was extracted with ethyl acetate (3×50 mL). The combined organic extract was washed with water (50 mL) and dried ($Na_2SO_4$). Volatile components were removed in vacuo to afford a 73.5% yield of the desired product, 3-O-tert-butyldimethylsilyloxy-4-methoxy benzyl alcohol.

C. 3-O-tert-butyldimethylsilyloxy-4-methoxy benzyl chloride

To a cooled (0° C.) solution of 3-O-tert-butyldimethylsilyloxy-4-methoxy benzyl alcohol (9.5 g, 35.4 mmol, 1 eq) in benzene (50 mL) under nitrogen, was added thionyl chloride (6.32 g, 1.5 eq) dissolved in benzene (5 mL) dropwise over 10 min. The resulting mixture was stirred at 0° C. and monitored by TLC. When the reaction was complete, water ice (50 g) was added and the resulting mixture was extracted with ethyl acetate (3×50 mL). The combined organic extract was washed with saturated bicarbonate solution (50 mL) and water (50 mL) and dried ($Na_2SO_4$). Volatile components were removed in vacuo to afford a quantitative yield of the product 3-O-tert-butyldimethylsilyloxy-4-methoxy benzyl chloride as a yellow oil.

D. 2-((3-O-tert-butyldimethylsilyloxy-4-methoxybenzyl)sulfanyl)acetic acid

To a solution of sodium hydroxide (2.79 g, 69.7 mmol, 2 eq) in methanol (30 mL) was added mercaptoacetic acid (3.21 g, 34.9 mmol, 1 eq) dropwise over 10 min. 3-O-tert-Butyldimethylsilyloxy-4-methoxy benzyl chloride was added portionwise to the mercaptoacetic acid mixture and the resulting mixture was stirred at room temperature and monitored by TLC. When the reaction was complete, the reaction mixture was poured onto ice (100 mL) containing concentrated HCl (excess based on sodium hydroxide). The resulting mixture was extracted with ethyl acetate (3×50 mL). The combined organic extract was washed with water (30 mL) and dried ($Na_2SO_4$). Volatile components were removed in vacuo to afford a 75% yield of the desired product 2-((3-O-tert-butyldimethylsilyloxy-4-methoxybenzyl)sulfanyl)acetic acid as a solid having a melting point of 57-59° C.

E. 2-((3-hydroxy-4-methoxybenzyl)sulfanyl)acetic acid

To a cooled (0° C.) solution of 2-((3-O-tert-butyldimethylsilyloxy-4-methoxybenzyl)sulfanyl)acetic acid (8.75 g, 25.5 mmol, 1 eq.) in THF (40 mL) was added dropwise, TBAF (1 eq., 1M in THF). The resulting mixture was stirred under nitrogen at room temperature and monitored by TLC. When the reaction was complete, water (40 mL) was added to the reaction mixture. The resulting mixture was extracted with ethyl acetate (3×40 mL). The combined organic extract was washed with water (40 mL) and dried ($Na_2SO_4$). Volatile components were removed in vacuo to yield the crude product, which was purified by column chromatography to afford a 50% yield of the purified product, 2-((3-hydroxy-4-methoxybenzyl)sulfanyl)acetic acid.

F. 3-hydroxy-4-methoxy benzyl sulfoneacetic acid

To a solution of 2-((3-hydroxy-4-methoxybenzyl)sulfanyl) acetic acid (2.9 g) in glacial acetic acid (15 mL) was added hydrogen peroxide (6 mL, 30% solution). The resulting mixture was stirred overnight at room temperature and monitored by TLC. When the reaction was complete, the reaction mixture was poured into ice water (10 mL) and extracted with ethyl acetate (3×10 mL). The combined organic extract was washed with water (10 mL) and dried ($Na_2SO_4$). Volatile components were removed in vacuo to afford a 60% yield of the pure product 3-hydroxy-4-methoxy benzyl sulfoneacetic acid having a melting point of 164-165° C.

G. (E)-5-((2,4,6-trimethoxystyrylsulfonyl)methyl)-2-methoxyphenol

A mixture of the 3-hydroxy-4-methoxy benzyl sulfoneacetic acid (1.9 g, 7.3 mmol, 1 eq), 2,4,6-trimethoxybenzaldehyde (1.58 g, 8.0 mmol, 1.1 eq), benzoic acid (134 mg, 0.15 eq) and piperidine (81 mg, 0.13 eq) in toluene (50 mL) was heated at reflux temperature for 2-3 h with continuous removal of water using a Dean-Stark trap. When the reaction was complete by TLC analysis, the reaction mixture was cooled to room temperature. Water was added and the resulting mixture was extracted with ethyl acetate (3×50 mL). The combined organic extract was washed with saturated aqueous sodium bicarbonate solution (50 mL), dilute hydrochloric acid (50 mL), and water (50 mL) and dried ($Na_2SO_4$). Volatile components were removed in vacuo to yield the crude product, which was purified by recrystallization from isopropanol to yield (1.8 g, 62.5%) of the desired (E)-5-((2,4,6-trimethoxystyrylsulfonyl)methyl)-2-methoxyphenol.

Example 2

(E)-5-((2,4,6-trimethoxystyrylsulfinyl)methyl)-2-methoxyphenol

A. 2-((3-hydroxy-4-methoxy-benzyl)sulfinyl)acetic acid

To a cooled (−5° C.) solution of 2-((3-hydroxy-4-methoxy-benzyl)sulfanyl)acetic acid (2.9 g) in anhydrous DCM (15 mL) is added MCPBA (20 mmol, 50% concentration basis, Lancaster). The reaction mixture is stirred at −5° C. for 6 hours. The precipitated 3-chlorobenzoic acid is removed by filtration. The filtrate is washed with water, dried over magnesium sulfate and concentrated. After removal of the solvent, the product 2-((3-hydroxy-4-methoxy-benzyl)sulfinyl)acetic acid is purified either by crystallization or by silica gel chromatography.

B. (E)-5-((2,4,6-trimethoxystyrylsulfinyl)methyl)-2-methoxyphenol

A mixture of the 3-hydroxy-4-methoxy benzyl sulfoneacetic acid (7 mmol, 1 eq), 2,4,6-trimethoxybenzaldehyde (8.0 mmol, 1.1 eq), benzoic acid (0.15 eq) and piperidine (0.1 eq) in toluene (50 mL) is heated at reflux temperature for 2-3 h with continuous removal of water using a Dean-Stark trap. When the reaction is complete by TLC analysis, the reaction mixture is cooled to room temperature. Water is added and the resulting mixture is extracted with ethyl acetate (3×50 mL). The combined organic extract is washed with saturated aqueous sodium bicarbonate solution (50 mL), dilute hydrochloric acid (50 mL), and water (50 mL) and dried ($Na_2SO_4$). Volatile components are removed in vacuo to yield the crude product, (E)-5-((2,4,6-trimethoxystyrylsulfinyl)methyl)-2-methoxyphenol which is purified by recrystallization from isopropanol.

Example 3

(E)-5-((2,4,6-trimethoxystyrylsulfonyl)methyl)-2-methoxyphenyl dibenzyl phosphate To a stirred solution of 5-((2,4,6-trimethoxystyrylsulfonyl)methyl)-2-methoxy-phenol (1.9 g, 4.8 mmol) in acetonitrile (24 mL) at room temperature, was added carbon tetrabromide (1.94 g, 1.22 eq) and triethylamine (0.728 g, 1.5 eq). The resulting mixture was stirred for 10 minutes and than cooled to 0° C. in an ice-water bath. Dibenzyl phosphite (1.51 g, 1.2 eq) dissolved in acetonitrile (16 mL) was added dropwise to the cooled reaction mixture. The reaction mixture was stirred for 2 h and monitored by TLC. The reaction was terminated by dropwise addition of aqueous potassium dihydrogen phosphate (10 mL, 0.5 M). The resulting mixture was extracted with ethyl acetate (3×30 mL). The combined organic extract was dried ($Na_2SO_4$) and concentrated in vacuo to yield the desired product.

Example 4

(E)-5-((2,4,6-trimethoxystyrylsulfonyl)methyl)-2-methoxyphenyl dihydrogen phosphate To a stirred solution of 5-((2,4,6-trimethoxystyrylsulfonyl)methyl)-2-methoxy-phenyl dibenzyl phosphate (4.36 g, 6.7 mmol) in anhydrous DCM (40 mL) under nitrogen at 0° C. was added bromotrimethylsilane (2.14 g, 2.1 eq). The resulting mixture was stirred for 45 minutes and monitored by TLC. sodium When the reaction was complete, aqueous sodium thiosulfate (1%, 50 mL) was added and the resulting mixture was stirred for an additional 5 minutes. The organic phase was separated and the aqueous phase was extracted with ethyl acetate (3×25 mL). The combined organic extract was concentrated in vacuo to afford the crude 5-((2,4,6-trimethoxystyrylsulfonyl)methyl)-2-methoxyphenyl dihydrogen phosphate. The product was purified column chromatography on silica eluted with a methanol/chloroform gradient to yield 1.4 g of the purified product having a melting point of 202-205° C.

Example 5

(E)-5-((2,4,6-trimethoxystyrylsulfonyl)methyl)-2-methoxyphenyl dihydrogen phosphate, disodium salt To a stirred solution of 5-((2,4,6-trimethoxystyrylsulfonyl)methyl)-2-methoxyphenyl dihydrogen phosphate (1.35 g) in ethylene glycol dimethyl ether (125 mL) was added 2N sodium hydroxide (2.4 eq). The resulting mixture was stirred for 3 h, filtered, washed with acetone (2×25 mL) and dried under vacuum to yield the 1.45 g of the disodium salt having a melting point of 152-154° C.

Example 6

(E)-5-((2,4,6-trimethoxystyrylsulfonyl)methyl)-2-methoxyphenyl diethyl phosphate To a stirred solution of 5-((2,4,6-trimethoxystyrylsulfonyl)methyl)-2-methoxyphenyl dihydrogen phosphate (1.9 g, 4.8 mmol) in acetonitrile (24 mL) at room temperature, was added carbon tetrabromide (1.94 g, 1.22 eq) and triethylamine (0.728 g, 1.5 eq). The resulting mixture was stirred for 10 minutes and than cooled to 0° C. in an ice-water bath. Diethyl phosphite (1.51 g, 1.2 eq) dissolved in acetonitrile (16 mL) was added dropwise to the cooled reaction mixture. The reaction mixture was stirred for 2 h and monitored by TLC. The reaction was terminated by dropwise addition of aqueous potassium dihydrogen phosphate (10 mL, 0.5 M). The resulting mixture was extracted with ethyl acetate (3×30 mL). The combined organic extract was dried ($Na_2SO_4$) and concentrated in vacuo to yield the desired product.

Example 7

Effect of Compounds of Formula I on Tumor Cell Lines

The effect of Compounds of Formula I on tumor cells of prostate, colon, lung, pancreatic, brain, renal, gastrointestinal, epidermal, lymphocytic, ovary and breast origin was examined by utilizing a variety of cancer cell lines (listed in Table 6). Cells were plated at density levels of 1.0×10$^5$ cells per well in six-well plates. Cell cultures were maintained at 37° C. in a humidified atmosphere of 5% $CO_2$.

Cells of 36 different cell lines were treated with (E)-5-((2,4,6-trimethoxystyrylsulfonyl)methyl)-2-methoxyphenol (Example 1) or (E)-5-((2,4,6-trimethoxystyrylsulfonyl)methyl)-2-methoxy-phenyl dihydrogen phosphate disodium salt (Example 5) at doses ranging from 2 nM to 10 nM concentration, and cell viability was determined after 96 hours by the Trypan blue exclusion method. In addition, DU-145 cells were treated with three additional compounds of the invention: (E)-4-(3-(5-((2,4,6-trimethoxystyrylsulfonyl)methyl)-2-methoxyphenoxy)propyl)morpholine; (E)-5-((2,4,6-trimethoxystyrylsulfonyl)methyl)-2-methoxyphenyl 2-(dimethylamino)acetate; and (E)-5-((2,4,6-trimethoxystyrylsulfonyl)methyl)-2-methoxyphenyl 4-methylbenzenesulfonate, the structures of which are shown in Table 7.

The results are set forth in Table 6 and Table 7. Values are reported as the GI$_{50}$, i.e., the concentration (μM) required for 50% growth inhibition as compared to vehicle (DMSO) treated cells. The notations "ER+" and "ER−" designate breast cancer lines that are responsive and non-responsive to estrogen, respectively. The notations "AR+" and "AR−" designate prostate cancer lines that are responsive and non-responsive to androgens, respectively. The notation "NT" indicates that the compound was not tested in that particular cell line. For cell lines designated by "*", the dose response curve for the compound (E)-5-((2,4,6-trimethoxystyrylsulfonyl)methyl)-2-methoxyphenol (Example 1) is set forth in FIG. 1.

TABLE 6

| Cell Line | Tumor Type | Compound of Example 1 GI$_{50}$ (μM) | Compound of Example 5 GI$_{50}$ (μM) |
| --- | --- | --- | --- |
| BT20 | Breast (Er−) | 0.08 | 0.008 |
| T47D | Breast (Er+) | 0.01 | Not done |
| MCF-7 | Breast (Er+) | 0.01 | Not done |
| DU145 | Prostate (Ar−) | 0.005 | 0.005 |
| LNCAP | Prostate (Ar+) | 0.01 | Not done |
| PC-3 | Prostate (Ar+) | 0.005 | Not done |
| OV-CAR-3 | Ovarian | 0.03 | Not done |
| Sk-OV-3 * | Ovarian | 0.004 | Not done |
| MIA-PACA2 | Pancreatic | 0.003 | 0.004 |
| U87 | Glioblastoma | 0.007 | 0.009 |
| H157 | Nsclc | 0.007 | 0.012 |
| A549 | Nsclc | 0.01 | 0.02 |
| H187 * | Sclc | 0.003 | Not done |
| N417 | Sclc | 0.003 | 0.004 |
| AGS | Gastric | 0.005 | 0.009 |
| RF1 | Gastric | 0.003 | Not done |
| RF48 * | Gastric | 0.001 | Not done |
| CAKI-2 | Renal | 0.006 | Not done |
| COLO-320 | Colo-Rectal | 0.003 | Not done |
| DLD-1 | Colo-Rectal | 0.007 | 0.012 |
| HCT-116 | Colo-Rectal | 0.006 | Not done |
| HCT-15 | Colo-Rectal | 0.007 | 0.012 |
| SW480 * | Colo-Rectal | 0.005 | Not done |
| SK-MEL-28 | Melanoma | 0.007 | 0.012 |
| CEM * | Leukemic | 0.004 | Not done |
| K562 | Cml | 0.004 | Not done |
| MOLT-4 | T-Lymphoblastic: All | 0.003 | Not done |
| Namalwa * | Burkitt's Lymphoma (B-Cell) | 0.003 | Not done |
| Daudi | Burkitt's Lymphoma (B-Cell) | 0.003 | Not done |
| Raji | Burkitt's Lymphoma (B-Cell) | 0.001 | Not done |
| Mes-Sa | Sarcoma | 0.005 | Not done |
| Mes-Sa/Dx5 | Resistant Sarcoma | 0.005 | Not done |
| Cem | Leukemia | 0.004 | Not done |
| Cem/C2 | Resistant Leukemic | 0.003 | Not done |
| 2008 | Ovarian | 0.005 | Not done |
| 2008/17/4 | Resistant Ovarian | 0.006 | Not done |

TABLE 7

| Compound Name and Structure | DU-145 GI$_{50}$ (μM) |
| --- | --- |

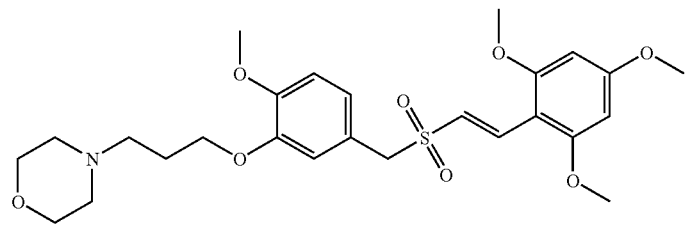

(E)-4-(3-(5-((2,4,6-trimethoxystyrylsulfonyl)methyl)-2-methoxyphenoxy)propyl)morpholine

>10

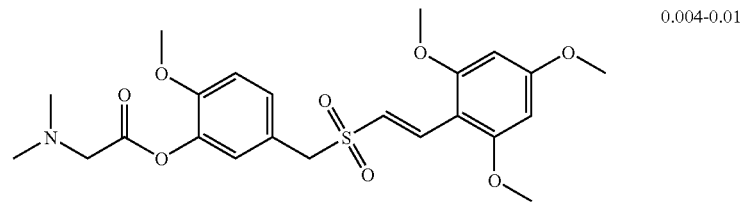

(E)-5-((2,4,6-trimethoxystyrylsulfonyl)methyl)-2-methoxyphenyl 2-(dimethylamino)acetate 0.004-0.01

TABLE 7-continued

| Compound Name and Structure | DU-145 GI$_{50}$ (μM) |
|---|---|
| 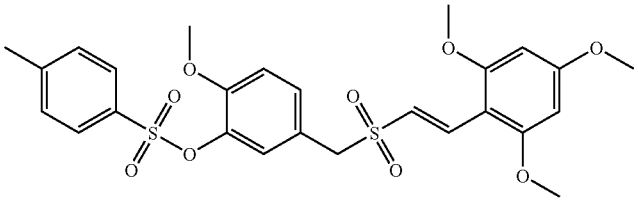<br>(E)-5-((2,4,6-trimethoxystyrylsulfonyl)methyl)-2-methoxyphenyl 4-methylbenzenesulfonate | >1 |

Example 8

Radioprotective Effect of Compounds of Formula I on Cultured Normal Human Cells The radioprotective effect of Formula I compounds on cultured normal cells is evaluated as follows.

HFL-1 cells are plated into 24 well dishes at a cell density of 3000 cells per 10 mm$^2$ in DMEM completed with 10% fetal bovine serum and antibiotics. A test compound according to Formula I is added to the cells 24 hours later at concentrations 0.25, 0.5, 1.0 and 2.0 micromolar, using DMSO as a solvent. Control cells are treated with DMSO alone. The cells are exposed to the test compound or DMSO for 24 hrs. The cells are then irradiated with either 10 Gy or 15 Gy of ionizing radiation (IR) using a J. L. Shepherd Mark I, Model 30-1 Irradiator equipped with cesium-137 as a source.

After irradiation, the medium on the test and control cells is removed and replaced with fresh growth medium without the test compounds or DMSO. The irradiated cells are incubated for 96 hours and duplicate wells are trypsinized and replated onto 100 mm$^2$ tissue culture dishes. The replated cells are grown under normal conditions with one change of fresh medium for 3 weeks. The number of colonies from each 100 mm$^2$ culture dish, which represents the number of surviving cells, is determined by staining the dishes as described below.

To visualize and count the colonies derived from the clonal outgrowth of individual radioprotected cells, the medium is removed and the plates are washed one time with ambient temperature phosphate buffered saline. The cells are stained with a 1:10 diluted Modified Giemsa staining solution (Sigma) for 20 minutes. The stain is removed, and the plates are washed with tap water. The plates are air-dried, the number of colonies from each plate is counted and the average from duplicate plates is determined.

Example 9

Effect of Exposure to Ionizing Radiation on Normal and Malignant Hematopoietic Progenitor Cell Growth after Pretreatment with Compounds of the Invention The effect of ionizing radiation on normal and malignant hematopoietic progenitor cells which are pretreated with compounds of the invention is determined by assessing cloning efficiency and development of the pretreated cells after irradiation.

To obtain hematopoietic progenitor cells, human bone marrow cells (BMC) or peripheral blood cells (PB) are obtained from normal healthy, or acute or chronic myelogenous leukemia (AML, CML), volunteers by Ficoll-Hypaque density gradient centrifugation, and are partially enriched for hematopoietic progenitor cells by positively selecting CD34$^+$ cells with immunomagnetic beads (Dynal A. S., Oslo, Norway). The CD34$^+$ cells are suspended in supplemented alpha medium and incubated with mouse anti-HPCA-I antibody in 1:20 dilution, 45 minutes, at 4° C. with gentle inverting of tubes. Cells are washed x 3 in supplemented alpha medium, and then incubated with beads coated with the Fc fragment of goat anti-mouse IgG$_1$ (75 μl of immunobeads/107 CD34$^+$ cells). After 45 minutes of incubation (4° C.), cells adherent to the beads are positively selected using a magnetic particle concentrator as directed by the manufacturer.

$2 \times 10^4$ CD34$^+$ cells are incubated in 5 mL polypropylene tubes (Fisher Scientific, Pittsburgh, Pa.) in a total volume of 0.4 mL of Iscove's modified Dulbecco's medium (IMDM) containing 2% human AB serum and 10 mM Hepes buffer. The test compounds of Formula I are added to the cells; in four different concentrations (0.25 μM, 0.5 μM, 1.0 μM and 2.0 μM). Control cells receive DMSO alone. The cells are incubated for 20-24 hours and irradiated with 5 Gy or 10 Gy of ionizing radiation.

Immediately after irradiation, the medium is removed and replaced with fresh medium without the test compound or DMSO. Twenty-four hours after irradiation, the treatment and control cells are prepared for plating in plasma clot or methylcellulose cultures. Cells ($1 \times 10^4$ CD34$^+$ cells per dish) are not washed before plating.

Assessment of the cloning efficiency and development of the treated hematopoietic progenitor cells are carried out essentially as reported in Gewirtz et al., *Science* 242, 1303-1306 (1988), the disclosure of which is incorporated herein by reference.

Example 10

Bone Marrow Purging with Ionizing Radiation after Pretreatment with Compounds of the Invention Bone marrow is harvested from the iliac bones of an individual under general anesthesia in an operating room using standard techniques. Multiple aspirations are taken into heparinized syringes. Sufficient marrow is withdrawn so that the individual will be able to receive about $4 \times 10^8$ to about $8 \times 10^8$ processed marrow cells per kg of body weight. Thus, about 750 to 1000 mL of marrow is withdrawn. The aspirated marrow is transferred immediately into a transport medium (TC-199, Gibco, Grand Island, N.Y.) containing 10,000 units of preservative-free heparin per 100 mL of medium. The aspirated marrow is filtered through three progressively finer meshes to obtain a cell suspension devoid of cellular aggregates, debris and bone particles. The filtered marrow is then processed further into an automated cell separator (e.g., Cobe 2991 Cell Processor) which prepares a "buffy coat" product, (i.e., leukocytes devoid of red cells and platelets). The buffy coat preparation is then placed in a transfer pack for further processing and storage. It may be stored until purging in liquid nitrogen using standard procedures. Alternatively, purging can be carried out immediately, then the purged marrow may be stored frozen in liquid nitrogen until it is ready for transplantation.

The purging procedure is carried out as follows. Cells in the buffy coat preparation are adjusted to a cell concentration of about $2 \times 10^7$/mL in TC-199 containing about 20% autologous plasma. Compounds of the invention, for example, at concentrations of from 0.25 μM to 2.0 μM are added to the transfer packs containing the cell suspension and incubated in a 37° C. waterbath for 20-24 hours with gentle shaking. The transfer packs are then exposed to 5-10 Gy ionizing radiation. Recombinant human hematopoietic growth factors, e.g., rH IL-3 or rH GM-CSF, may be added to the suspension to stimulate growth of hematopoietic neoplasms and thereby increase their sensitivity to ionizing radiation.

The cells may then either be frozen in liquid nitrogen or washed once at 4° C. in TC-199 containing about 20% autologous plasma. Washed cells are then infused into the individual. Care must be taken to work under sterile conditions wherever possible and to maintain scrupulous aseptic techniques at all times.

Example 11

Protection of Normal Human Fibroblasts from Paclitaxel Cytotoxicity by Compounds of Formula I HFL-1 cells are plated at a cell density of $1.0 \times 10^5$ per well 24 hours prior to drug addition. Cells are pretreated with a compound according to Formula I (2.0 μM) for 8 hours and then exposed to paclitaxel (250 μM). Other cells are treated with paclitaxel alone, or both agents simultaneously. Cells are enumerated by Trypan blue exclusion using a hematocytometer 96 hours after exposure to paclitaxel. Cytoprotective activity may be compared by comparing the number of viable cells following treatment with a compound according to Formula I and paclitaxel, divided by the number of viable cells remaining after treatment with paclitaxel alone.

Example 12

Protection of Normal Human Fibroblasts from Anticancer Agent Cytotoxicity

HFL-1 cells are plated at a cell density of $1.0 \times 10^5$ in 1 ml of medium. Twenty-four hours following plating, 2.0 μM of a compound according to Formula I is added to the medium. Following a 24-hour preincubation with the compound according to Formula I, the various cytotoxic agents selected from the list in Table 8 are added to the cells.

The number of viable cells is determined by Trypan blue exclusion using a hematocytometer 96 hours after exposure to cytotoxic agent. The "Protection Ratio" is the number of viable cells following treatment with a compound according to Formula I and the selected cytotoxic agent, divided by the number of viable cells remaining after treatment with cytotoxic agent alone. A protection ratio of 2 or more is considered highly significant, while a protection ratio of 1.5-2 is considered less significant.

TABLE 8

| Drug | Therapeutic concentration (μM) | Mechanism of Action |
| --- | --- | --- |
| paclitaxel | 0.25 | antimitotic |
| vincristine | 0.25 | antimitotic |
| camptothecin | 0.5 | topoisomerase I inhibitor |
| etoposide | 3.0 | topoisomerase II inhibitor |
| mitoxantrone | 0.3 | topoisomerase II inhibitor |
| doxorubicin | 0.4 | topoisomerase II inhibitor |
| 5-fluorouracil | 20 | DNA antimetabolite |
| cisplatin | 5.0 | alkylating agent |

Example 13

Protection of Normal Human Fibroblasts from Vincristine Cytotoxicity by Compounds of Formula I HFL-1 cells are treated with 0-250 μM vincristine and, optionally, a 2.0 μM preparation of a compound according to Formula I, either 24 hours before or after vincristine treatment, or simultaneously with vincristine treatment. Cell viability is assessed 96 hours after the addition of vincristine.

Example 14

Protection of Mice from Paclitaxel Toxicity Using Compounds of Formula I

ICR female mice age 10-12 weeks (Taconic) are divided into the following treatment groups and receive intraperitoneal injections of 50 mg/Kg a compound according to Formula I, dissolved in DMSO and/or 150 mg/kg paclitaxel (Taxol, Sigma Chemical Co.) dissolved in DMSO. The compound according to Formula I is given 24 hours before paclitaxel, 4 hours before paclitaxel, or simultaneously with paclitaxel. Control animals receive paclitaxel alone or a compound according to Formula I alone. Mortality is assessed 48 and 144 hours after paclitaxel injection.

All references cited herein are incorporated by reference. The present invention may be embodied in other specific forms without departing from the spirit or essential attributes thereof and, accordingly, reference should be made to the appended claims, rather than to the foregoing specification, as indication the scope of the invention.

What is claimed is:

1. A compound according to Formula I:

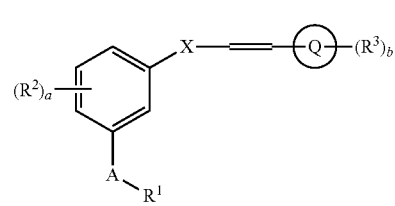

wherein:

A is —S— or —O—;

$R^1$ is selected from the group consisting of halo($C_1$-$C_6$) alkyl, —C(=O)$R^w$, —S(=O)$R^w$, —SO$_2$$R^w$, —(($C_1$-$C_6$)hydrocarbylene)$R^z$, —P(=O)(O$R^v$)$_2$, —C($R^a$)

(R$^v$)—C(=O)—R'', substituted and unsubstituted aryl, substituted and unsubstituted heteroaryl, —Si[(C$_1$-C$_6$)alkyl]$_3$, and —CH$_2$CH$_2$Si[(C$_1$-C$_6$)alkyl]$_3$;

each R$^v$ is independently selected from the group consisting of —H and —(C$_1$-C$_7$)hydrocarbyl;

R$^w$ is selected from the group consisting of NR$^v$$_2$, —OR$^v$, halo(C$_1$-C$_3$)alkyl, —NR$^v$CR$^v$R$^a$—C(=O)—R'', —CR$^v$R$^a$—N(R$^v$)—R$^c$, substituted and unsubstituted aryl, substituted and unsubstituted aryl(C$_1$-C$_3$)alkyl, substituted and unsubstituted heteroaryl, substituted and unsubstituted heteroaryl(C$_1$-C$_3$)alkyl, substituted and unsubstituted heterocyclyl, substituted and unsubstituted heterocyclyl(C$_1$-C$_3$)alkyl, —((C$_1$-C$_3$)alkylene)P(=O)(OR$^v$)$_2$, —(C$_1$-C$_3$)perfluoroalkylene-N(CH$_3$)$_2$, —(C$_1$-C$_3$)alkylene-N((C$_1$-C$_3$)alkyl)$_2$, —(C$_1$-C$_3$)alkylene-N$^+$((C$_1$-C$_3$)alkyl)$_3$, —(C$_1$-C$_3$)alkylene-N$^+$(CH$_2$CH$_2$OH)$_3$, —((C$_1$-C$_4$)alkylene)-C(=O)-halogen, —(C$_1$-C$_4$)perfluoroalkylene-CO$_2$R$^v$, —((C$_1$-C$_3$)alkylene)C(=O)OR$^v$, and —((C$_1$-C$_3$)alkylene)OC(=O)—((C$_1$-C$_3$)alkylene)C(=O)R$^y$;

R$^y$ is selected from the group consisting of —OR$^v$, —NR$^v$$_2$ and —(C$_1$-C$_6$)alkyl;

R$^z$ is selected from the group consisting of —C(=O)R$^y$, —NR$^v$CR$^v$R$^a$—C(=O)—R'', —OR$^v$, substituted and unsubstituted aryl, substituted and unsubstituted heteroaryl, substituted and unsubstituted heterocyclyl(C$_1$-C$_3$)alkyl, and —C(=O)(C$_1$-C$_3$)alkyl;

each R$^a$ is independently selected from the group consisting of —H, —(C$_1$-C$_6$)alkyl, —(C$_1$-C$_6$)heteroalkyl, —(CH$_2$)$_3$—NH—C(NH$_2$)(=NH), —CH$_2$C(=O)NH$_2$, —CH$_2$COOH, —(CH$_2$)$_2$COOH, substituted and unsubstituted aryl, substituted and unsubstituted aryl(C$_1$-C$_3$)alkyl, substituted and unsubstituted heterocyclyl, and substituted and unsubstituted heterocyclyl(C$_1$-C$_3$)alkyl;

each R'' is independently selected from the group consisting of —OR$^v$, —NR$^v$$_2$, and an N-terminally linked peptidyl residue containing from 1 to 3 amino acids in which the terminal carboxyl group of the peptidyl residue is present as a functional group selected from the group consisting of —CO$_2$R$^v$ and —C(=O)NR$^v$$_2$;

each R$^c$ is independently selected from the group consisting of —H and a carboxy terminally linked peptidyl residue containing from 1 to 3 amino acids in which the terminal amino group of the peptidyl residue is present as a functional group selected from the group consisting of —NH$_2$, —NHC(=O)(C$_1$-C$_6$)alkyl, —NH(C$_1$-C$_6$)alkyl, —NH((C$_1$-C$_6$)alkyl)$_2$ and —NHC(=O)O(C$_1$-C$_7$)hydrocarbyl;

Q is aryl or heteroaryl;

each R$^2$ and R$^3$ is independently selected from the group consisting of halogen, —(C$_1$-C$_7$)hydrocarbyl, —C(=O)R$^v$, —NR$^v$$_2$, —NHC(=O)R$^v$, —NHSO$_2$R$^v$, —NHR$^a$, —NHCR$^v$R$^a$C(=O)R'', —NHSO$_2$R$^v$, —C(=O)OR$^v$, —C(=O)NHR$^v$, —NO$_2$, —CN, —OR$^v$, —P(=O)(OR$^v$)$_2$, —C(=NH)NH$_2$, dimethylamino(C$_2$-C$_6$)alkoxy, —NHC(=NR$^v$)NHR$^v$, —(C$_1$-C$_6$)haloalkyl, and —(C$_1$-C$_6$)haloalkoxy;

the two R$^v$ groups on —P(=O)(OR$^v$)$_2$ and —NR$^v$$_2$ may optionally form a five- or six-membered heterocyclic ring, which may further optionally be fused to an aryl or carbocyclic ring;

a is 0, 1, 2 or 3;

b is 0, 1, 2 or 3;

the configuration of the substituents on the exocyclic carbon-carbon double bond is either E- or Z-;

X is —C*H(R$^x$)Y—;

Y is —S(=O)— or —SO$_2$—;

R$^x$ is selected from the group consisting of —H, —(C$_1$-C$_6$)alkyl, and —C(=O)(C$_1$-C$_6$)alkyl; and

* indicates that, when R$^x$ is other than —H, the configuration of the substituents on the designated carbon atom is (R)-, (S)- or any mixture of (R)- and (S)-, or a salt of such a compound;

provided that:

when A is —O—:
  R$^1$ is other than halo(C$_1$-C$_6$)alkyl; and
  R$^Z$ is other than unsubstituted aryl.

2. A compound according to claim 1, or a salt of such a compound, wherein:

R$^w$ is selected from the group consisting of NR$^v$$_2$, —OR$^v$, halo(C$_1$-C$_3$)alkyl, —NR$^v$CR$^v$R$^a$—C(=O)—R'', —CR$^v$R$^a$—N(R$^v$)—R$^c$, substituted and unsubstituted aryl, substituted and unsubstituted aryl(C$_1$-C$_3$)alkyl, substituted and unsubstituted heteroaryl, substituted and unsubstituted heteroaryl(C$_1$-C$_3$)alkyl, substituted and unsubstituted heterocyclyl, substituted and unsubstituted heterocyclyl(C$_1$-C$_3$)alkyl, —((C$_1$-C$_3$)alkylene)P(=O)(OR$^v$)$_2$, —(C$_1$-C$_3$)perfluoroalkylene-N(CH$_3$)$_2$, —(C$_1$-C$_3$)alkylene-N$^+$((C$_1$-C$_3$)alkyl)$_3$, —(C$_1$-C$_3$)alkylene-N$^+$(CH$_2$CH$_2$OH)$_3$, —((C$_1$-C$_4$)alkylene)-C(=O)-halogen, —(C$_1$-C$_4$)perfluoroalkylene-CO$_2$R$^v$, —((C$_1$-C$_3$)alkylene)C(=O)OR$^v$, and —((C$_1$-C$_3$)alkylene)OC(=O)—((C$_1$-C$_3$)alkylene)C(=O)R$^y$; and R$^z$ is selected from the group consisting of —C(=O)R$^y$, —NR$^v$CR$^v$R$^a$—C(=O)—R'', OR$^v$, substituted and unsubstituted aryl, substituted and unsubstituted heteroaryl and —C(=O)(C$_1$-C$_3$)alkyl.

3. A compound according to claim 1, or a salt thereof, wherein Q is aryl.

4. A compound according to claim 1, or a salt thereof, wherein Q is heteroaryl.

5. A compound according to claim 1, of Formula IE:

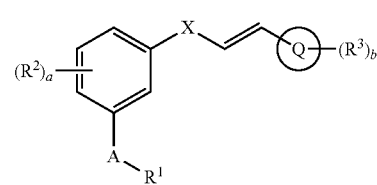

IE wherein the exocyclic carbon-carbon double bond is in the (E)-configuration; and R$^1$, R$^2$, R$^3$, A, a, b, X and Q are as defined as in claim 1, or a salt of such a compound.

6. A compound according to claim 1, of Formula IZ:

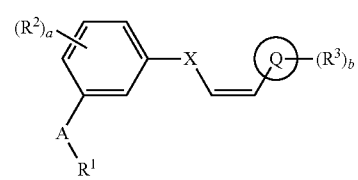

IZ wherein the exocyclic carbon-carbon double bond is in the (Z)-configuration; and R$^1$, R$^2$, R$^3$, A, a, b, X and Q are as defined as in claim 1, or a salt of such a compound.

7. A compound according to claim 1, or a salt thereof, wherein the sum of a and b is at least 2.

8. A compound according to claim 1, of Formula IA:

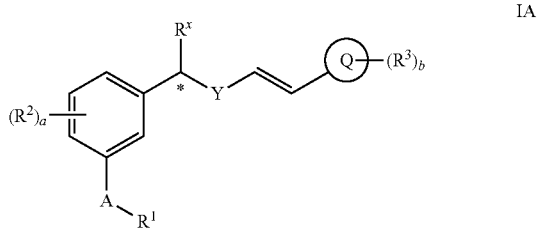

wherein $R^2$, $R^3$, A, a, b, Q, Y and $R^x$ are as defined as in claim 1;

$R^1$ is selected from the group consisting of —P(═O)(OR$^v$)$_2$, —C(═O)R$^w$—SO$_2$R$^w$, and —((C$_1$-C$_6$)hydrocarbylene)R$^z$; and

* indicates that, when $R^x$ is other than —H, the configuration of the substituents on the designated carbon atom is (R)-, (S)- or any mixture of (R)- and (S)-;

or a salt of such a compound.

9. A compound according to claim 8, or a salt thereof, wherein $R^1$ is —P(═O)(OR$^v$)$_2$.

10. A compound according to claim 9, or a salt thereof, wherein $R^x$ is —H.

11. A compound according to claim 8, or a salt thereof, wherein $R^1$ is —C(═O)R$^w$.

12. A compound according to claim 11, or a salt thereof, wherein $R^x$ is —H.

13. A compound according to claim 8, or a salt thereof, wherein $R^1$ is —SO$_2$R$^w$.

14. A compound according to claim 13, or a salt thereof, wherein $R^x$ is —H.

15. A compound according to claim 8, or a salt thereof, wherein $R^1$ is —((C$_1$-C$_6$)hydrocarbylene)R$^z$.

16. A compound according to claim 15, or a salt thereof, wherein $R^x$ is —H.

17. A compound according to claim 1, selected from the group consisting of (E)-5-((2,4,6-trimethoxystyrylsulfonyl)methyl)-2-methoxyphenyl dimethyl phosphate; (E)-5-((2,4,6-trimethoxystyrylsulfonyl)methyl)-2-methoxyphenyl diethyl phosphate; (E)-5-((2,4,6-trimethoxystyrylsulfonyl)methyl)-2-methoxyphenyl dibenzyl phosphate; (E)-S-5-((2,4,6-trimethoxystyrylsulfonyemethyl)-2-methoxyphenyl-O,O-dihydrogen phosphorothioate; (E)-S-5-((2,4,6-trimethoxystyrylsulfonyemethyl)-2-methoxyphenyl-O,O-dimethyl phosphorothioate; (E)-S-5-((2,4,6-trimethoxystyrylsulfonyl)methyl)-2-methoxy-phenyl-O,O-diethyl phosphorothioate; (E)-S-5-((2,4,6-trimethoxystyrylsulfonyl)methyl)-2-methoxyphenyl-O,O-dibenzyl, phosphorothioate; (E)-5-((2,4,6-trimethoxystyrylsulfinyl)methyl)-2-methoxyphenyl dimethyl phosphate; (E)-5-((2,4,6-trimethoxystyrylsulfinyl)methyl)-2-methoxyphenyl diethyl phosphate; (E)-5-((2,4,6-trimethoxystyrylsulfinyl)methyl)-2-methoxyphenyl dibenzyl phosphate; (E)-S-5-((2,4,6-trimethoxystyryl-sulfinyl)methyl)-2-methoxyphenyl-O,O-dihydrogen phosphorothioate; (E)-S-5-((2,4,6-trimethoxystyrylsulfinyl)methyl)-2-methoxyphenyl-O,O-dimethyl phosphorothioate; (E)-S-5-((2,4,6-trimethoxy-styrylsulfinyl)methyl)-2-methoxyphenyl-O,O-diethyl phosphorothioate; (E)-S-5-((2,4,6-trimethoxy-styrylsulfinyl)methyl)-2-methoxyphenyl-O,O-dibenzyl phosphorothioate; (E)-2-((5-((2,4,6-trimethoxystyrylsulfonyl)methyl)-2-methoxyphenoxy)-carbonyl)acetic acid; (E)-5-((2,4,6-trimethoxystyrylsulfonyl)methyl)-2-methoxyphenyl-3,5-dinitrobenzoate; (E)-5-((2,4,6-trimethoxystyrylsulfonyl)-methyl)-2-methoxyphenyl-3,5-diaminobenzoate; (E)-5-((2,4,6-trimethoxystyryl-sulfonyl)methyl)-2-methoxyphenyl-2-chloroacetate; (E)-5-((2,4,6-trimethoxy-styrylsulfonyl)methyl)-2-methoxyphenyl-2-(4-methylpiperazin-1-yl)acetate; (E)-5-((2,4,6-trimethoxystyrylsulfonyl)methyl)-2-methoxyphenyl benzoate; (E)-5-((2,4,6-trimethoxystyrylsulfonyl)methyl)-2-methoxyphenyl-4-nitrobenzoate; (E)-5-((2,4,6-trimethoxystyrylsulfonyl)methyl)-2-methoxyphenyl-4-aminobenzoate; (E)-(R)-5-((2,4,6-trimethoxystyrylsulfonyl)methyl)-2-methoxyphenyl-2,6-diaminohexanoate; (E)-(R)-5-((2,4,6-trimethoxystyrylsulfonyl)methyl)-2-methoxyphenyl-2-amino-3-hydroxypropanoate; (E)-(S)-5-((2,4,6-trimethoxystyrylsulfonyl)methyl)-2-methoxyphenyl-2-amino-3-hydroxypropanoate; (E)-5-((2,4,6-trimethoxystyrylsulfonyl)methyl)-2-methoxy-phenyl carbamate; (E)-5-((2,4,6-trimethoxystyrylsulfonyl)methyl)-2-methoxy-phenyl-2-(di-methylamino)acetate; (E)-5-((2,4,6-trimethoxystyryl-sulfonyl)methyl)-2-methoxyphenyl-4-(4-methylpiperazin-1-yl)benzoate; (E)-5-((2,4,6-trimethoxystyrylsulfonyl)methyl)-2-methoxyphenyl-2-(pyridinium-1-yl)acetate; (E)-5-((2,4,6-trimethoxystyrylsulfonyl)methyl)-2-methoxyphenyl-2-(triethylammonium)-acetate; (E)-5-((2,4,6-trimethoxystyrylsulfonyl)methyl)-2-methoxyphenyl-2-(tris(2-hydroxyethyl)ammonium)acetate; (E)-5-((2,4,6-trimethoxystyrylsulfonyl)methyl)-2-methoxy-phenyl-2,2,2-trifluoroacetate; (E)-3-((5-((2,4,6-trimethoxystyrylsulfonyl)-methyl)-2-methoxyphenoxy)-carbonyl)propanoic acid; (E)-5-((2,4,6-trimethoxystyrylsulfonyl)methyl)-2-methoxyphenyl-3-(chlorocarbonyl)-propanoate; (E)-4-((5-((2,4,6-trimethoxystyrylsulfonyl)-methyl)-2-methoxyphenoxy)-carbonyl)butanoic acid; (E)-5-((2,4,6-trimethoxystyrylsulfonyl)methyl)-2-methoxyphenyl methyl carbonate; (E)-5-((2,4,6-trimethoxy-styrylsulfonyl)methyl)-2-methoxyphenyl methyl succinate; (E)-5-((2,4,6-trimethoxystyrylsulfonyl)methyl)-2-methoxyphenyl ethyl malonate; (E)-5-((2,4,6-trimethoxy-styrylsulfonyl)methyl)-2-methoxyphenyl-2,2,3,3,3-pentafluoropropanoate; (E)-5-((2,4,6-trimethoxystyrylsulfonyl)methyl)-2-methoxyphenyl)-3-methyl-2,2-difluoromalonate; (E)-3-((5-((2,4,6-trimethoxystyrylsulfonyl)methyl)-2-methoxyphenoxy)-carbonyl)-2,2,3,3-tetrafluoro-propanoic acid; (E)-5-((2,4,6-trimethoxystyrylsulfonyl)methyl)-2-methoxyphenyl 2-aminoacetate; (E)-2-((5-((2,4,6-trimethoxystyrylsulfonyl)-methyl)-2-methoxyphenoxy)carbonyl)-2,2-difluoro-acetic acid; (E)-5-((2,4,6-trimethoxystyrylsulfonyl)-methyl)-2-methoxyphenyl-2-(dimethylamino)-2,2-difluoroacetate; (E)-5-((2,4,6-trimethoxystyrylsulfonyl)methyl)-2-methoxyphenyl-2-(dimethylamino)acetate; (E)-2-((5-((2,4,6-trimethoxystyrylsulfinyl)methyl)-2-methoxyphenoxy)carbonyl)acetic acid; (E)-5-((2,4,6-trimethoxystyrylsulfinyl)-methyl)-2-methoxyphenyl-3,5-dinitrobenzoate; (E)-5-((2,4,6-trimethoxystyryl-sulfinyl)methyl)-2-methoxyphenyl-3,5-diaminobenzoate; (E)-5-((2,4,6-trimethoxystyrylsulfinyl)methyl)-2-methoxyphenyl-2-chloroacetate; (E)-5-((2,4,6-trimethoxystyrylsulfinyl)methyl)-2-methoxyphenyl-2-(4-methylpiperazin-1-yl)acetate; (E)-5-((2,4,6-trimethoxystyrylsulfinyl)methyl)-2-methoxyphenyl benzoate; (E)-5-((2,4,6-trimethoxystyrylsulfinyl)methyl)-2-methoxyphenyl-4-nitrobenzoate; (E)-5-((2,4,6-trimethoxy-styrylsulfinyl)methyl)-2-methoxyphenyl-4-aminobenzoate; (E)-(R)-5-((2,4,6-trimethoxystyrylsulfinyl)-methyl)-2-methoxyphenyl 2,6-diaminohexanoate; (E)-(R)-5-((2,4,6-trimethoxy-styrylsulfinyl)methyl)-2-methoxyphenyl 2-amino-3-hydroxypropanoate; (E)-(S)-5-((2,4,6-trimethoxystyrylsulfinyl)methyl)-2-methoxyphenyl-2-amino-3-hydroxypropanoate; (E)-5-((2,4,6-trimethoxystyrylsulfinyl)methyl)-2-methoxy-phenyl carbamate; (E)-5-((2,4,6-trimethoxystyrylsulfinyl)methyl)-2-methoxy-phenyl 2-(di-methylamino)acetate; (E)-5-((2,4,6-trimethoxystyrylsulfinyl)-methyl)-2-methoxyphenyl 4-(4-methylpiperazin-1-yl)benzoate; (E)-5-((2,4,6-trimethoxystyrylsulfinyl)methyl)-2-methoxyphenyl-2-(pyridinium-1-yl)-acetate; ((2,4,6-trimethoxystyrylsulfinyl)-methyl)-2-methoxyphenyl-2-(triethylammonium)acetate; (E)-5-((2,4,6-trimethoxystyrylsulfinyl)methyl)-2-methoxyphenyl 2-(tris(2-hydroxyethyl)-ammonium)acetate; (E)-5-((2,4,6-trimethoxystyrylsulfinyl)methyl)-2-methoxyphenyl-2,2,2-trifluoroacetate; (E)-3-((5-((2,4,6-trimethoxystyrylsulfinyl)methyl)-2-methoxyphenoxy)-carbonyl)-propanoic acid; (E)-5-((2,4,6-trimethoxystyrylsulfinyl)methyl)-2-methoxy-phenyl-3-(chlorocarbonyl)propanoate; (E)-4-((5-((2,4,6-trimethoxystyrylsulfinyl)methyl)-2-methoxyphenoxy)-carbonyl)butanoic acid; (E)-5-((2,4,6-trimethoxystyrylsulfinyl)methyl)-2-methoxyphenyl methyl carbonate; (E)-5-((2,4,6-trimethoxystyryl-sulfinyl)methyl)-2-methoxyphenyl methyl succinate; (E)-5-((2,4,6-tri-methoxystyrylsulfinyl)methyl)-2-methoxyphenyl ethyl malonate; (E)-5-((2,4,6-trimethoxystyrylsulfinyl)methyl)-2-methoxyphenyl-2,2,3,3,3-pentafluoropropanoate; (E)-1-(5-((2,4,6-trimethoxystyrylsulfinyl)methyl)-2-methoxyphenyl)-3-methyl-2,2-difluoromalonate; (E)-3-((5-((2,4,6-trimethoxystyrylsulfinyl)methyl)-2-methoxyphenoxy)-carbonyl)-2,2,3,3-tetrafluoro-propanoic acid; (E)-5-((2,4,6-trimethoxystyrylsulfinyl)methyl)-2-methoxyphenyl-2-amino-acetate; (E)-2-((5-((2,4,6-tri-methoxystyrylsulfinyl)-methyl)-2-methoxyphenoxy)-carbonyl)-2,2-difluoroacetic acid; (E)-5-((2,4,6-trimethoxystyrylsulfinyl)methyl)-2-methoxyphenyl-2-(dimethylamino)-2,2-difluoroacetate; 5-((2,4,6-trimethoxystyrylsulfinyl)methyl)-2-methoxyphenyl-2-(dimethylamino)acetate; (E)-5-((2,4,6-trimethoxystyrylsulfonyl)methyl)-2-methoxyphenyl carboxymethanesulfonate; (E)-5-((2,4,6-trimethoxystyryl-sulfonyl)methyl)-2-methoxyphenyl-2,4-dinitrobenzene-sulfonate; (E)-5-((2,4,6-trimethoxystyryl-sulfonyl)methyl)-2-methoxyphenyl-2,4-diaminobenzene-sulfonate; (E)-5-((2,4,6-trimethoxystyrylsulfonyl)methyl)-2-methoxyphenyl trifluoromethanesulfonate; (E)-5-((2,4,6-trimethoxystyryl-sulfonyl)methyl)-2-methoxyphenyl-4-methoxy-benzene-sulfonate; (E)-5-((2,4,6-trimethoxystyrylsulfinyl)methyl)-2-methoxy-phenyl carboxymethanesulfonate; (E)-5-((2,4,6-trimethoxystyrylsulfinyl)methyl)-2-methoxyphenyl-2,4-dinitrobenzenesulfonate; (E)-5-((2,4,6-trimethoxystyrylsulfinyl)methyl)-2-methoxyphenyl-2,4-diaminobenzene-sulfonate; (E)-5-((2,4,6-trimethoxystyrylsulfinyl)methyl)-2-methoxyphenyl trifluoromethanesulfonate; (E)-5-((2,4,6-trimethoxystyryl-sulfinyl)methyl)-2-methoxyphenyl-4-methoxybenzene-sulfonate; (E)-5-((2,4,6-trimethoxystyrylsulfonyl)methyl)-2-methoxyphenyl-4-methylbenzenesulfonate; (E)-5-((2,4,6-trimethoxystyrylsulfinyl)methyl)-2-methoxyphenyl-4-methylbenzenesulfonate; (E)-2-(5-((2,4,6-trimethoxystyrylsulfonyl)methyl)-2-methoxyphenoxy)-acetic acid; (E)-2-(5-((2,4,6-trimethoxystyrylsulfonyl)methyl)-2-methoxyphenoxy)-propanoic acid; (E)-4-(5-((2,4,6-trimethoxystyrylsulfonyl)methyl)-2-methoxyphenoxy)-butanoic acid; (E)-3-(5-((2,4,6-trimethoxystyryl-sulfonyl)methyl)-2-methoxyphenoxy)-propanoic acid; (E)-2-(5-((2,4,6-trimethoxystyrylsulfinyl)methyl)-2-methoxyphenoxy)-acetic acid; (E)-2-(5-((2,4,6-trimethoxystyrylsulfinyl)methyl)-2-methoxyphenoxy)-propanoic acid; (E)-4-(5-((2,4,6-trimethoxystyrylsulfinyl)methyl)-2-methoxyphenoxy)-butanoic acid; (E)-3-(5-((2,4,6-trimethoxystyrylsulfinyl)methyl)-2-methoxyphenoxy)-propanoic acid; (E)-4-(2-(5-((2,4,6-trimethoxystyrylsulfonyl)methyl)-2-methoxyphenoxy)ethyl)morpholine; (E)-4-(2-(5-((2,4,6-trimethoxystyrylsulfinyl)methyl)-2-methoxyphenoxy)ethyl)morpholine; (E)-4-(3-(5-((2,4,6-trimethoxystyrylsulfonyl)methyl)-2-methoxyphenoxy)propyl)morpholine; and salts thereof.

18. A process for preparing a compound according claim 5 of Formula IE:

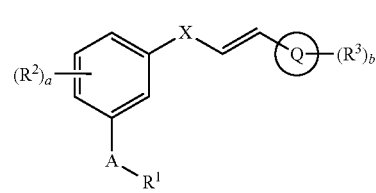

wherein $R^1$, $R^2$, $R^3$, A, a, b, X and Q are as defined as in claim 5;

or a salt of such a compound; comprising the steps of:
(a) reacting a compound according to Formula VII:

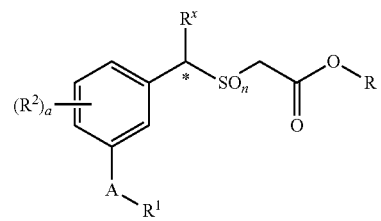

wherein:
n is 1 or 2;
R is —H;
A is —S— or —O—;
$R^1$ is selected from the group consisting of —C(=O)$R^w$, —S(=O)$R^w$, —SO$_2$$R^w$, —(($C_1$-$C_6$)hydrocarbylene)$R^z$, —P(=O)(O$R^v$)$_2$, —C($R^a$)($R^v$)—C(=O)—$R^n$, substituted and unsubstituted aryl, substituted and unsubstituted heteroaryl, —Si[($C_1$-$C_6$)alkyl]$_3$, and —CH$_2$CH$_2$Si[($C_1$-$C_6$)alkyl]$_3$;
each $R^v$ is independently selected from the group consisting of —H and —($C_1$-$C_7$)hydrocarbyl;
$R^w$ is selected from the group consisting of —N$R^v$$_2$, halo ($C_1$-$C_3$ alkyl), —N$R^v$C$R^v$$R^a$—C(=O)—$R^n$, —C$R^v$$R^a$—N($R^v$)—$R^c$, substituted and unsubstituted aryl, substituted and unsubstituted aryl($C_1$-$C_3$)alkyl, substituted and unsubstituted heteroaryl, substituted and unsubstituted heteroaryl($C_1$-$C_3$)alkyl, substituted and unsubstituted heterocyclyl, substituted and unsubstituted heterocyclyl($C_1$-$C_3$)alkyl, —(($C_1$-$C_3$)alkylene)P(=O)(O$R^v$)$_2$, —($C_1$-$C_3$)perfluoroalkylene-N(CH$_3$)$_2$, —($C_1$-$C_3$)alkylene-N$^+$(($C_1$-$C_3$)alkyl)$_3$, —($C_1$-$C_3$)alkylene-N$^+$(CH$_2$CH$_2$OH)$_3$, —(($C_1$-$C_4$)alkylene)-C(=O)-halogen, —($C_1$-$C_4$)perfluoroalkylene-CO$_2$$R^v$, —(($C_1$-$C_3$)alkylene)C(=O)O$R^v$, and —(($C_1$-$C_3$)alkylene)OC(=O)—(($C_1$-$C_3$)alkylene)C(=O)$R^v$;

$R^y$ is selected from the group consisting of —$OR^v$, —$NR^v_2$ and —($C_1$-$C_6$)alkyl;

$R^z$ is selected from the group consisting of —C(=O)$R^y$, —$NR^vCR^vR^a$—C(=O)—$R^v$, —$OR^v$, substituted aryl, substituted and unsubstituted heteroaryl and —C(=O)($C_1$-$C_3$)alkyl;

each $R^a$ is independently selected from the group consisting of —H, —($C_1$-$C_6$)alkyl, —($C_1$-$C_6$)heteroalkyl, —($CH_2$)$_3$—NH—C($NH_2$)(=NH), —$CH_2$C(=O)$NH_2$, —$CH_2$COOH, —($CH_2$)$_2$COOH, substituted and unsubstituted aryl, substituted and unsubstituted aryl($C_1$-$C_3$)alkyl, substituted and unsubstituted heterocyclyl, and substituted and unsubstituted heterocyclyl($C_1$-$C_3$)alkyl;

each $R^n$ is independently selected from the group consisting of —$OR^v$, —$NR^v_2$, and an N-terminally linked peptidyl residue containing from 1 to 3 amino acids in which the terminal carboxyl group of the peptidyl residue is present as a functional group selected from the group consisting of —$CO_2R^v$ and —C(=O)$NR^v_2$;

each $R^c$ is independently selected from the group consisting of —H and a carboxy terminally linked peptidyl residue containing from 1 to 3 amino acids in which the terminal amino group of the peptidyl residue is present as a functional group selected from the group consisting of —$NH_2$, —NHC(=O)($C_1$-$C_6$)alkyl, —NH($C_1$-$C_6$)alkyl, —NH(($C_1$-$C_6$)alkyl)$_2$ and —NHC(=O)O($C_1$-$C_7$)hydrocarbyl;

each $R^2$ is independently selected from the group consisting of halogen, —($C_1$-$C_7$)hydrocarbyl, —C(=O)$R^v$, —$NR^v_2$, —NHC(=O)$R^v$, —NHSO$_2$$R^v$, —$NHR^a$, —$NHCR^vR^aC$(=O)$R^n$, —NHSO$_2$$R^{v'}$, —C(=O)$OR^v$, —C(=O)$NHR^v$, —$NO_2$, —CN, —P(=O)(OR$^v$)$_2$, —C(=NH)$NH_2$, dimethylamino($C_2$-$C_6$)alkoxy, —NHC(=NR$^v$)$NHR^v$, —($C_1$-$C_6$)haloalkyl, and —($C_1$-$C_6$)haloalkoxy;

the two $R^v$ groups on —P(=O)(OR$^v$)$_2$ and —$NR^v_2$ may optionally form a five- or six-membered heterocyclic ring, which may further optionally be fused to an aryl or carbocyclic ring;

a is 0, 1, 2 or 3;

$R^x$ is selected from the group consisting of —H, —($C_1$-$C_6$)alkyl and —C(=O)($C_1$-$C_6$)alkyl; and

* indicates that, when $R^x$ is other than —H, the configuration of the substituents on the designated carbon atom is R-, S- or any mixture of R- and S-, or a salt of such a compound;

with a compound according to Formula XVI:

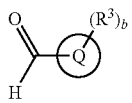

wherein:
Q is aryl or heteroaryl;

each $R^3$ is independently selected from the group consisting of halogen, —($C_1$-$C_7$)hydrocarbyl, —C(=O)$R^v$, $NR^v_2$, —NHC(=O)$R^v$, —NHSO$_2$$R^v$, —$NHCR^vR^aC$(=O)$R^n$, —NHSO$_2$$R^v$, —C(=O)$OR^v$, —C(=O)$NHR^v$, —$NO_2$, —CN, —$OR^v$, —P(=O)(OR$^v$)$_2$, —C(=NH)$NH_2$, dimethylamino($C_2$-$C_6$)alkoxy, —NHC(=NR$^v$)$NHR^v$, —($C_1$-$C_6$)haloalkyl, and —($C_1$-$C_6$)haloalkoxy; and b is 0, 1, 2 or 3; and (b) isolating a compound according to Formula IE, or a salt thereof, from the reaction products.

19. A process for preparing a compound according to claim 6 of the Formula IZ:

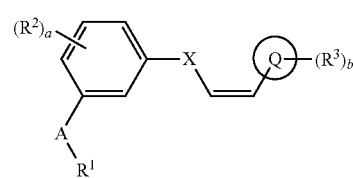

wherein $R^1$, $R^2$, $R^3$, a, b, X and Q are as defined as in claim 6;

A is —O—;

or a salt of such a compound;

comprising the steps of:

(a) reacting a compound according to Formula XI:

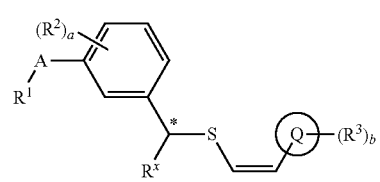

wherein:

A is —O—;

$R^1$ is selected from the group consisting of —C(=O)$R^w$, —S(=O)$R^w$, —SO$_2$$R^w$, —(($C_1$-$C_6$)hydrocarbylene)$R^z$, —P(=O)(OR$^v$)$_2$, —C($R^a$)($R^v$)—C(=O)—$R^n$, substituted and unsubstituted aryl, substituted and unsubstituted heteroaryl, —Si[($C_1$-$C_6$)alkyl]$_3$, and —$CH_2CH_2$Si[($C_1$-$C_6$)alkyl]$_3$;

each $R^v$ is independently selected from the group consisting of —H and —($C_1$-$C_7$)hydrocarbyl;

$R^w$ is selected from the group consisting of —$NR^v_2$, —$OR^v$, halo($C_1$-$C_3$ alkyl), —$NR^vCR^vR^a$—C(=O)—$R^n$, —$CR^vR^a$—N($R^v$)—$R^c$, substituted and unsubstituted aryl, substituted and unsubstituted aryl($C_1$-$C_3$)alkyl, substituted and unsubstituted heteroaryl, substituted and unsubstituted heteroaryl($C_1$-$C_3$)alkyl, substituted and unsubstituted heterocyclyl, substituted and unsubstituted heterocyclyl($C_1$-$C_3$)alkyl, —(($C_1$-$C_3$)alkylene)P(=O)(OR$^v$)$_2$, —($C_1$-$C_3$)perfluoroalkylene-N(CH$_3$)$_2$, —($C_1$-$C_3$)alkylene-N$^+$(($C_1$-$C_3$)alkyl)$_3$, —($C_1$-$C_3$)alkylene-N$^+$(CH$_2$CH$_2$OH)$_3$, —(($C_1$-$C_4$)alkylene)-C(=O)-halogen, —($C_1$-$C_4$)perfluoroalkylene-CO$_2$$R^v$, —(($C_1$-$C_3$)alkylene)C(=O)$OR^v$, and —(($C_1$-$C_3$)alkylene)OC(=O)—(($C_1$-$C_3$)alkylene)C(=O)$R^y$;

$R^y$ is selected from the group consisting of —$OR^v$, —$NR^v_2$ and —($C_1$-$C_6$)alkyl;

$R^z$ is selected from the group consisting of —C(=O)$R^y$, —$NR^vCR^vR^a$—C(=O)—$R^a$, substituted aryl, substituted and unsubstituted heteroaryl and —C(=O)($C_1$-$C_3$)alkyl;

each $R^a$ is independently selected from the group consisting of —H, —($C_1$-$C_6$)alkyl, —($C_1$-$C_6$)heteroalkyl, —($CH_2$)$_3$—NH—C($NH_2$)(=NH), —$CH_2$C(=O)$NH_2$, —$CH_2$COOH, —($CH_2$)$_2$COOH, substituted and unsubstituted aryl, substituted and unsubstituted aryl($C_1$-$C_3$)

alkyl, substituted and unsubstituted heterocyclyl, and substituted and unsubstituted heterocyclyl($C_1$-$C_3$)alkyl;

each $R''$ is independently selected from the group consisting of —$OR^v$, —$NR^v_2$, and an N-terminally linked peptidyl residue containing from 1 to 3 amino acids in which the terminal carboxyl group of the peptidyl residue is present as a functional group selected from the group consisting of —$CO_2R^v$ and —$C(=O)NR^v_2$;

each $R^c$ is independently selected from the group consisting of —H and a carboxy terminally linked peptidyl residue containing from 1 to 3 amino acids in which the terminal amino group of the peptidyl residue is present as a functional group selected from the group consisting of —$NH_2$, —$NHC(=O)(C_1$-$C_6)$alkyl, —$NH(C_1$-$C_6)$alkyl, —$NH((C_1$-$C_6)$alkyl$)_2$ and —$NHC(=O)O(C_1$-$C_7)$hydrocarbyl;

Q is aryl or heteroaryl;

each $R^2$ and $R^3$ is independently selected from the group consisting of halogen, —($C_1$-$C_7$)hydrocarbyl, —$C(=O)R^v$, —$NR^v_2$, —$NHC(=O)R^v$, —$NHSO_2R^v$, —$NHR^a$, —$NHCR^vR^aC(=O)R^n$, —$NHSO_2R^v$, —$C(=O)OR^v$, —$C(=O)NHR^v$, —$NO_2$, —CN, —$P(=O)(OR^v)_2$, —$C(=NH)NH_2$, dimethylamino($C_2$-$C_6$)alkoxy, —$NHC(=NR^v)NHR^v$, —($C_1$-$C_6$)haloalkyl, and —($C_1$-$C_6$)haloalkoxy;

the two $R^v$ groups on —$P(=O)(OR^v)_2$ and —$NR^v_2$ may optionally form a five- or six-membered heterocyclic ring, which may further optionally be fused to an aryl or carbocyclic ring;

a is 0, 1, 2 or 3;

b is 0, 1, 2 or 3;

the configuration of the exocyclic carbon-carbon double bond is Z-;

$R^x$ is selected from the group consisting of —H, —($C_1$-$C_6$) alkyl, and —$C(=O)(C_1$-$C_6)$alkyl; and

* indicates that, when $R^x$ is other than —H, the configuration of the substituents on the designated carbon atom is (R)-, (S)- or any mixture of (R)- and (S)-, or a salt of such a compound;

with an oxidizing agent capable of oxidizing a sulfide to a sulfoxide or a sulfone; and (b) isolating a compound according to Formula IZ, or a salt thereof, from the reaction products.

20. A process for preparing a compound according to Formula I:

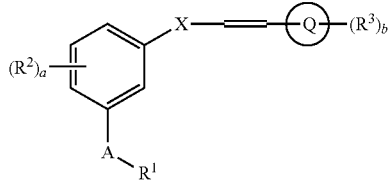

I or a salt of such a compound, wherein:

A is —S— or —O—;

$R^1$ is —$P(=O)(OR^v)_2$ wherein $R^v$ is —($C_1$-$C_7$)hydrocarbyl;

each $R^v$ is independently selected from the group consisting of —H and —($C_1$-$C_7$)hydrocarbyl;

each $R^a$ is independently selected from the group consisting of —H, —($C_1$-$C_6$)alkyl, —($C_1$-$C_6$)heteroalkyl, —($CH_2)_3$—NH—$C(NH_2)(=NH)$, —$CH_2C(=O)NH_2$, —$CH_2COOH$, —$(CH_2)_2COOH$, substituted and unsubstituted aryl, substituted and unsubstituted aryl($C_1$-$C_3$) alkyl, substituted and unsubstituted heterocyclyl, and substituted and unsubstituted heterocyclyl($C_1$-$C_3$)alkyl;

each $R''$ is independently selected from the group consisting of —$OR^v$, —$NR^v_2$, and an N-terminally linked peptidyl residue containing from 1 to 3 amino acids in which the terminal carboxyl group of the peptidyl residue is present as a functional group selected from the group consisting of —$CO_2R^v$ and —$C(=O)NR^v_2$;

Q is aryl or heteroaryl;

each $R^2$ and $R^3$ is independently selected from the group consisting of halogen, —($C_1$-$C_7$)hydrocarbyl, —$C(=O)R^v$, —$NR^v_2$, —$NHC(=O)R^v$, —$NHSO_2R^v$, —$NHCR^vR^aC(=O)R^n$, —$NHSO_2R^v$, —$C(=O)OR^v$, —$C(=O)NHR^v$, —$NO_2$, —CN, —$OR^v$, —$P(=O)(OR^v)_2$, —$C(=NH)NH_2$, dimethylamino($C_2$-$C_6$)alkoxy, —$NHC(=NR^v)NHR^v$, —($C_1$-$C_6$)haloalkyl, and —($C_1$-$C_6$)haloalkoxy;

the two $R^v$ groups on —$P(=O)(OR^v)_2$ and —$NR^v_2$ may optionally form a five- or six-membered heterocyclic ring, which may further optionally be fused to an aryl or carbocyclic ring;

a is 0, 1, 2 or 3;

b is 0, 1, 2 or 3;

the configuration of the substituents on the exocyclic carbon-carbon double bond is either E- or Z-;

X is —$C*H(R^x)Y$—;

Y is —$S(=O)$— or —$SO_2$—;

$R^x$ is selected from the group consisting of —H, —($C_1$-$C_6$) alkyl, and —$C(=O)(C_1$-$C_6)$alkyl; and

* indicates that, when $R^x$ is other than —H, the configuration of the substituents on the designated carbon atom is (R)-, (S)- or any mixture of (R)- and (S)-, or a salt of such a compound;

comprising the steps of:

(a) reacting a compound according to Formula II:

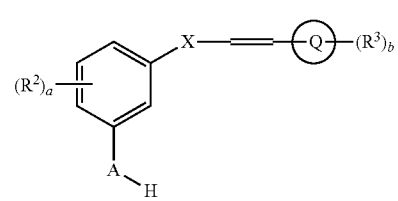

II wherein $R^2$, $R^3$, X, A, Q, a and b are as defined as for Formula;

with a dihydrocarbylphosphityl halide of the Formula:

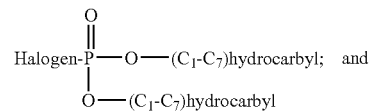

(b) isolating from the reaction products a compound of Formula I, or a salt of such a compound; wherein $R^1$ is —$P(=O)(OR^v)_2$; and $R^v$ is —($C_1$-$C_7$)hydrocarbyl.

21. A process for preparing a compound of Formula I:

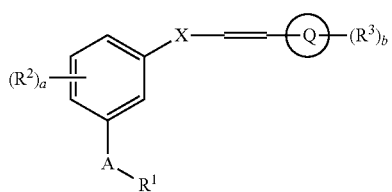

I or a salt of such a compound, wherein $R^2$, $R^3$, X, A, Q, a and b are as defined as in claim 1; $R^1$ is —P(=O)(OR$^v$)$_2$; and R$^v$ is H;
comprising the steps of:
(a) reacting a compound according to Formula I, wherein $R^1$ is —P(=O)(OR$^v$)$_2$; and R$^v$ is —(C$_1$-C$_7$)hydrocarbyl, with a halotrialkyl silane of the Formula:

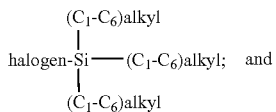

(b) isolating from the reaction products a compound of Formula I, or a salt of such a compound, wherein $R^2$, $R^3$, X, A, Q, a and b are as defined as in claim 1; $R^1$ is —P(=O)(OR$^v$)$_2$; and R$^v$ is H.

22. A pharmaceutical composition comprising a pharmaceutically acceptable carrier and a compound according to claim 1, or a pharmaceutically acceptable salt of such a compound.

23. A compound according to claim 1 which is (E)-5-((2,4,6-trimethoxystyrylsulfonyl)methyl)-2-methoxyphenyl dihydrogen phosphate or a salt thereof.

24. A compound according to claim 23 which is (E)-5-((2,4,6-trimethoxystyrylsulfonyl)methyl)-2-methoxyphenyl dihydrogen phosphate, disodium salt.

25. A compound according to claim 1 which is (E)-5-((2,4,6-trimethoxystyrylsulfinyl)methyl)-2-methoxyphenyl dihydrogen phosphate or a salt thereof.

26. A compound according to claim 25 which is (E)-5-((2,4,6-trimethoxystyrylsulfinyl)methyl)-2-methoxyphenyl dihydrogen phosphate, disodium salt.

* * * * *